US008921529B2

(12) United States Patent
Shone et al.

(10) Patent No.: US 8,921,529 B2
(45) Date of Patent: Dec. 30, 2014

(54) THERAPIES FOR PREVENTING OR SUPPRESSING *CLOSTRIDIUM DIFFICILE* INFECTION

(75) Inventors: Clifford Shone, Salisbury (GB); April Roberts, Salisbury (GB); John Landon, Newcastle Emlyn (GB)

(73) Assignee: Health Protection Agency, Salisbury (GB)

( * ) Notice: Subject to any disclaimer, the term of this patent is extended or adjusted under 35 U.S.C. 154(b) by 0 days.

(21) Appl. No.: 13/513,555

(22) PCT Filed: Dec. 6, 2010

(86) PCT No.: PCT/GB2010/052035
§ 371 (c)(1),
(2), (4) Date: Sep. 10, 2012

(87) PCT Pub. No.: WO2011/067616
PCT Pub. Date: Jun. 9, 2011

(65) Prior Publication Data
US 2013/0004561 A1 Jan. 3, 2013

(30) Foreign Application Priority Data

Dec. 4, 2009 (GB) .................................. 0921288.7
Feb. 19, 2010 (WO) ................ PCT/GB2010/050288

(51) Int. Cl.
*C07K 16/00* (2006.01)
*C07K 16/12* (2006.01)
*A61K 39/00* (2006.01)

(52) U.S. Cl.
CPC ....... *C07K 16/1282* (2013.01); *A61K 2039/505* (2013.01); *A61K 2039/542* (2013.01); *C07K 2317/20* (2013.01)
USPC ..................................... 530/389.5; 424/167.1

(58) Field of Classification Search
None
See application file for complete search history.

(56) References Cited

U.S. PATENT DOCUMENTS

| 4,755,383 | A | | 7/1988 | Fujii et al. |
| 5,601,823 | A | * | 2/1997 | Williams et al. ........... 424/167.1 |
| 5,773,000 | A | | 6/1998 | Bostwick et al. |
| 6,096,310 | A | | 8/2000 | Bier |
| 8,709,428 | B2 | | 4/2014 | Shone et al. |
| 2004/0028705 | A1 | | 2/2004 | Ballard et al. |
| 2004/0126383 | A1 | | 7/2004 | Thomas, Jr. et al. |
| 2007/0071763 | A1 | | 3/2007 | Burnie et al. |
| 2008/0145370 | A1 | | 6/2008 | Simon |

FOREIGN PATENT DOCUMENTS

| CN | 101014620 | 8/2007 |
| CN | 101363867 | 2/2009 |
| GB | 0902851.5 | 6/2009 |
| GB | 0916153.0 | 1/2010 |
| GB | 0921288.7 | 4/2010 |
| WO | WO 98/59053 | 12/1998 |
| WO | WO 99/20304 | 4/1999 |
| WO | WO 99/45903 | 9/1999 |
| WO | WO 00/44402 | 8/2000 |
| WO | WO 02/43767 | 6/2002 |
| WO | WO 03/074555 | 9/2003 |
| WO | WO 2004/041857 | 5/2004 |
| WO | WO 2006/071877 | 7/2006 |
| WO | WO 2006/121422 | 11/2006 |
| WO | PCT/GB2010/050288 | 5/2010 |
| WO | PCT/GB2010/050288 | 3/2011 |
| WO | PCT/GB2010/052035 | 3/2011 |
| WO | PCT/GB2010/050288 | 5/2011 |
| WO | WO 2011/067616 | 6/2011 |
| WO | PCT/GB2010/052035 | 12/2011 |
| WO | PCT/GB2010/052035 | 3/2012 |

OTHER PUBLICATIONS

Dart RC, (2001. Ann. Emerg. Med. 37:181-188).*
O'Brien J. (2007. Infect. Control Hosp. Epidemiol. 28:1219-1227).*
Schaeffer et al (J. Am. Osteopath. Assoc. 110:587-592).*
http://en.wikipedia.org/wiki/Polyclonal_antibodies.2013.*
Rahman et al (Vet Med. Czech. 2001. 46(9-10: 241-243.*
Aslam, S. et al., "Treatment of *Clostridium difficile*-associated disease: old therapies and new strategies", The Lancet Infectious Diseases, vol. 5, issue 9, pp. 549-557, (2005).
Kink, J.A. et al., "Antibodies to recombinant *Clostridium difficile* toxins A and B are an effective treatment and prevent relapse of *C. difficile*-associated disease in a hamster model of infection", Infection and Immunity, vol. 66, No. 5, pp. 2018-2025, (1998).
McPherson, S. et al., "Intravenous immunoglobulin for the treatment of severe, refractory, and recurrent *Clostridium difficile* diarrhea", Diseases of the Colon & Rectum, vol. 49, No. 5, pp. 640-645, (2006).
Baldacini, O. et al., "Comparative study of immunological properties and cytotoxic effects of *Clostridium difficile* toxin B and *Clostridium sordellii* toxin L", Toxicon, vol. 30, No. 2, pp. 129-140, (1992).
Leffler, D.A. et al., "Treatment of *Clostridium difficile*-associated disease", Gastroenterology, vol. 136, No. 6, pp. 1899-1912, (2009).
Ehrich, M. et al., "Production of *Clostridium difficile* antitoxin", Infection and Immunity, vol. 28, No. 3, pp. 1041-1043, (1980).
Nguiyen, V.K. et al., "Enzyme immunoassay (ELISA) for detection of *Clostridium difficile* toxin B in specimens of faeces", Journal of Medical Microbiology, vol. 31, pp. 251-257, (1990).
Taylor, C.P. et al., "Open-label, dose escalation phase 1 study in healthy volunteers to evaluate the safety and pharmacokinetics of a human monoclonal antibody to *Clostridium difficile* toxin A", Vaccine, vol. 26, No. 26-27, pp. 3404-3409, (2008).
Young, K.W.H. et al., "The safety of whey protein concentrate derived from the milk of cows immunized against *Clostridium difficile*", Regulatory Toxicology and Pharmacology, vol. 47, pp. 317-326, (2007).

(Continued)

*Primary Examiner* — Jennifer Graser
(74) *Attorney, Agent, or Firm* — Evan Law Group LLC

(57) ABSTRACT

The present invention provides an antibody composition comprising ovine antibodies, for use in the prevention or treatment of *C. difficile* infection wherein the antibodies bind to a *C. difficile* toxin, and wherein said prevention or treatment is by oral delivery of the antibody composition. Also provided is a pharmaceutical composition of ovine antibodies for oral delivery, which further comprises one or more means for protecting the antibodies from trypsin and/or chymotrypsin and/or stomach acid.

16 Claims, 5 Drawing Sheets

(56) References Cited

OTHER PUBLICATIONS

Figure 1:
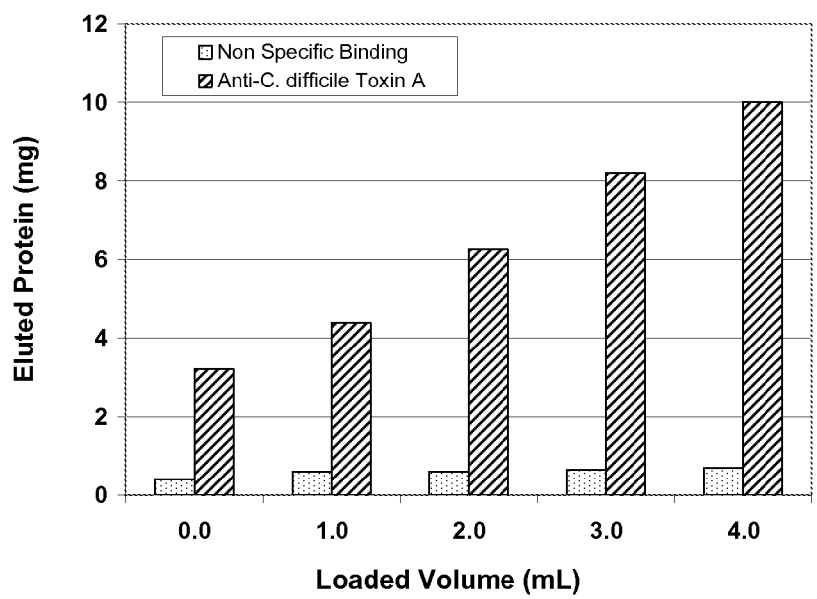

Redwan, E-R. M. et al., "Production and purification of ovine anti-tetanus antibody", Comparative Immunology Microbiology & Infectious Diseases, vol. 28, pp. 167-176, (2005).
International Search Report dated May 10, 2010 for PCT application No. PCT/GB2010/050288.
GB Search Report dated Jun. 3, 2009 for GB application No. GB0902851.5.
GB Search Report dated Jan. 15, 2010 for GB application No. GB0916153.0.
International Preliminary Examining Authority Written Opinion of the International Preliminary Examining Authority dated Mar. 8, 2011 for PCT application No. PCT/GB2010/050288.
Smith, T.F. et al., "Comparison of biosequences", Advances in Applied Mathematics, vol. 2, issue 4, pp. 482-489, (1981).
Needleman, S.B. et al., "A general method applicable to the search for similarities in the amino acid sequence of two proteins", Journal of Molecular Biology, vol. 48, issue 3, pp. 443-453, (1970).
Pearson, W.R. et al., "Improved tools for biological sequence comparison", Proceedings of the National Academy of Science, vol. 85, pp. 2444-2448, (1988).
Altschul, S.F. et al., "Basic local alignment search tool", Journal of Molecular Biology, vol. 215, issue 3, pp. 403-410, (1990).
Chothia, C. et al., "Canonical structures for the hypervariable regions of immunoglobulins}", Journal of Molecular Biology, vol. 196, pp. 901-917, (1987).
Ward, E.S. et al., "Binding activities of a repertoire of single immunoglobulin variable domains secreted from *Escherichia coli*", Nature, vol. 341, pp. 544-546, (1989).
Bird, R.E. et al., "Single-chain antigen-binding proteins", Science, vol. 242, issue 4877, pp. 423-426, (1988).
Huston, J.S. et al., "Protein engineering of antibody binding sites: Recovery of specific activity in an anti-digoxin single-chain Fv analogue produced in *Escherichia coli*", Proceedings of the National Academy of Science, vol. 85, pp. 5879-5883, (1988).
Roberts, A.K. et al., "Modification of surface hiswtiding residues abolishes the cytotoxic activity of *Clostridium difficile* toxin A", Toxicon, vol. 39, issues 2-3, pp. 325-333, (2001).
Rupnik, M. et al., "A novel tosinotyping scheme and correlation of toxinotypes with serogroups of *Clostridium difficile* isolates", Journal of Clinical Microbiology, vol. 36, No. 8, pp. 2240-2247, (1998).
Rupnik, M. et al., "Comparison of toxinotyping and PCR ribotyping of *Clostridium difficile* strains and description of novel toxinotypes", Microbiology, vol. 147, pp. 439-447, (2001).
Sambrook et al., "Molecular Cloning a Laboratory Manual", Second Edition, Cold Spring Harbor Laboratory Press, Cold spring harbor, New York (1989).
Li, M. et al., "In vitro protein refolding by chromatographic procedures", Protein Expression & Purification, vol. 33, pp. 1-10, (2004).
Yang et al., "Expression of recombinant *Clostridium difficile* toxin A and B in *Bacillus megaterium*", BMC Microbiology, vol. 8, No. 192, 13 pages, (2008).
Curd, J. et al., "The isolation of digoxin-specific antibody and its use in reversing the effects of digoxin", Proceedings of the National Academy of Science, vol. 68, No. 10, pp. 2401-2406, (1971).
Allen, G. "The affinity of binding of digoxin to ovine anti-digoxin fab (DIGIBIND™)* preparations", Biologicals, vol. 24, pp. 19-24, (1996).
Lambkin, I. et al., "Targeting approaches to oral drug delivery", Expert Opinion Biol. Therapy, vol. 2, No. 1, pp. 67-73, (2002).
Bernkop-Schnurch, A., "The use of inhibitory agents to overcome the enzymatic barrier to perorally administered therapeutic peptides and proteins", Journal of Controlled Release, vol. 52, pp. 1-16, (1998).
Nguyen, V.K. et al., "Enzyme immunoassay (ELISA) for detection of *Clostridium difficile* toxin B in specimens of faeces", Journal of Medical Microbiology, vol. 31, pp. 251-257, (1990).
Warny, M. et al., "Bovine immunoglobulin concentrate—*Clostridium difficile* retains *C difficile* toxin neutralising activity after passage through the human stomach and small intestine", Gut, vol. 44, pp. 212-217, (1999).

GB Search Report dated Apr. 1, 2010 for GB application No. GB0921288.7.
International Search Report dated Mar. 18, 2011 for PCT application No. PCT/GB2010/052035.
Guha, M.K. et al., "Purification and characterization of chymotrypsin inhibitors from marine turtle egg white", Journal of Biosciences, vol. 6, No. 2, pp. 155-163, (1984).
Rummel, A. et al., "Two carbohydrate binding sites in the $H_{cc}$-domain of tetanus neurotoxin are required for toxicity", Journal of Molecular Biology, vol. 326, issue 3, pp. 835-847, (2003).
Greco, A. et al., "Carbohydrate recognition by *Clostridium difficile* toxin A", Nature Structural & Molecular Biology, vol. 13, pp. 460-461, (2006).
Ho, J.G.S. et al., "Crystal structure of receptor-binding C-terminal repeats from *Clostridium difficile* toxin A", Proceedings of the National Academy of Science, vol. 102, No. 51, pp. 18373-18378, (2005).
Greenwald, R.B. et al., "Effective drug delivery by PEGylated drug conjugates", Advanced Drug Delivery Reviews, vol. 55, issue 2, pp. 217-250, (2003).
Sundriyal, A. et al., "Expression, purification and cell cytotoxicity of actin-modifying binary toxin from *Clostridium difficile*", Protein Expression and Purification, vol. 74, issue 1, pp. 42-48, (2010).
Lineweaver, H. et al., "Identification of the trypsin inhibitor of egg white with ovomucoid", Journal of Biological Chemistry, vol. 171, No. 2, pp. 565-581, (1947).
Kakade, M.L. et al., "Determination of trypsin inhibitor activity of soy products: a collaborative analysis of an improved procedure", USDA.gov, (1974).
Esquisabel, A. et al., "Production of BCG alginate-PLL microcapsules by emulsification/internal gelation", Journal of Microencapsulation, vol. 14, No. 5, pp. 627-638, (1997).
Munjeri, O. et al., "In vivo behavior of hydrogel beads based on amidated pectins", Drug Delivery, vol. 5, No. 4, pp. 239-241, (1998).
Giannasca, P.J. et al., "Serum antitoxin antibodies mediate systemic and mucosal protection from *Clostridium difficile* disease in hamsters", Infection and Immunity, vol. 67, No. 2, pp. 527-538, (1999).
Libby, J.M. et al., "Production of antitoxins to two toxins of *Clostridium difficile* and immunological comparison of the toxins by cross-neutralization studies", Infection and Immunity, vol. 35, No. 1, pp. 374-376, (1982).
van Dissel, J.T. et al., "Bovine antibody-enriched whey to aid in the prevention of a relapse of *Clostridium difficile*-associated diarrhoea: preclinical and preliminary clinical data", Journal of Medical Microbiology, vol. 54, pp. 197-205, (2005).
Kelly, C.P. et al., "Anti-*Clostridium difficile* bovine immunoglobulin concentrate inhibits cytotoxicity and enterotoxicity of *C. difficile* toxins", Antimicrobial Agents and Chemotherapy, vol. 40, No. 2, pp. 373-379, (1996).
Lyerly, D.M. et al., "Passive immunization of hamsters against disease caused by *Clostridium difficile* by use of bovine immunoglobulin G. concentrate", Infection and Immunity, vol. 59, No. 6, pp. 2215-2218, (1991).
Torres, J.F. et al., "Evaluation of formalin-inactivated *Clostridium difficile* vaccines administered by parenteral and mucosal routes of immunization in hamsters"Infection and Immunity, vol. 63, No. 12, pp. 4619-4627, (1995).
Greenspan, N.S. et al., "Defining epitopes: It's not as easy as it seems", Nature Biotechnology, vol. 17, pp. 936-937, (1999).
Barbut, F. et al., "Clinical features of *Clostridium difficile*-associated diarrhoea due to binary toxin (actin-specific ADP-ribosyltransferase)-producing strains", Journal of Medical Microbiology, vol. 54, pp. 181-185, (2005).
Wang, X. et al., "Enzyme-linked immunosorbent assay for detection and quantitation of *Clostridium difficile* toxin A", Progress in Microbiology and Immunology, vol. 24, No. 4, pp. 7-11, (1996).
Liu, Y. et al., "Latest advances on the study of *Clostridium difficile* associated diarrhea", Chinese Journal of Infection and Chemotherapy, vol. 6, No. 4, pp. 280-283, (2006).
Translation of Peoples Republic of China Search Report obtained on Oct. 18, 2013 for CN application No. 2010/80053778.9.
Jul. 19, 2013, 201080053778.9, CN.
U.S. Appl. No. 13/202,557, filed Dec. 5, 2013.

(56) References Cited

OTHER PUBLICATIONS

U.S. Appl. No. 13/202,557, filed Aug. 21, 2013.
U.S. Appl. No. 13/202,557, filed Apr. 2, 2014.
U.S. Appl. No. 13/202,557, filed Oct. 5, 2012.
U.S. Appl. No. 13/202,557, filed Feb. 20, 2013.
Feb. 28, 2013, 201080008673.1, CN.

* cited by examiner

SEQUENCE LISTING

<160> NUMBER OF SEQ ID NOS: 9

<210> SEQ ID NO 1
<211> LENGTH: 2710
<212> TYPE: PRT
<213> ORGANISM: Clostridium difficile

<400> SEQUENCE: 1

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Glu Asn Lys Tyr Leu Gln Leu
                35                  40                  45

Lys Lys Leu Asn Glu Ser Ile Asp Val Phe Met Asn Lys Tyr Lys Thr
50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365
```

```
Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
```

```
            785                 790                 795                 800
        Ser Ile Ser Glu Asp Ile Lys Thr Leu Leu Asp Ala Ser Val Ser
                        805                 810                 815
        Pro Asp Thr Lys Phe Ile Leu Asn Asn Leu Lys Leu Asn Ile Glu Ser
                        820                 825                 830
        Ser Ile Gly Asp Tyr Ile Tyr Tyr Glu Lys Leu Glu Pro Val Lys Asn
                        835                 840                 845
        Ile Ile His Asn Ser Ile Asp Asp Leu Ile Asp Glu Phe Asn Leu Leu
                        850                 855                 860
        Glu Asn Val Ser Asp Glu Leu Tyr Glu Leu Lys Lys Leu Asn Asn Leu
        865                 870                 875                 880
        Asp Glu Lys Tyr Leu Ile Ser Phe Glu Asp Ile Ser Lys Asn Asn Ser
                        885                 890                 895
        Thr Tyr Ser Val Arg Phe Ile Asn Lys Ser Asn Gly Glu Ser Val Tyr
                        900                 905                 910
        Val Glu Thr Glu Lys Glu Ile Phe Ser Lys Tyr Ser Glu His Ile Thr
                        915                 920                 925
        Lys Glu Ile Ser Thr Ile Lys Asn Ser Ile Ile Thr Asp Val Asn Gly
                        930                 935                 940
        Asn Leu Leu Asp Asn Ile Gln Leu Asp His Thr Ser Gln Val Asn Thr
        945                 950                 955                 960
        Leu Asn Ala Ala Phe Phe Ile Gln Ser Leu Ile Asp Tyr Ser Ser Asn
                        965                 970                 975
        Lys Asp Val Leu Asn Asp Leu Ser Thr Ser Val Lys Val Gln Leu Tyr
                        980                 985                 990
        Ala Gln Leu Phe Ser Thr Gly Leu Asn Thr Ile Tyr Asp Ser Ile Gln
                        995                 1000                1005
        Leu Val Asn Leu Ile Ser Asn  Ala Val Asn Asp Thr  Ile Asn Val
                1010                1015                1020
        Leu Pro Thr Ile Thr Glu Gly  Ile Pro Ile Val Ser  Thr Ile Leu
                1025                1030                1035
        Asp Gly Ile Asn Leu Gly Ala  Ala Ile Lys Glu Leu  Leu Asp Glu
                1040                1045                1050
        His Asp Pro Leu Leu Lys Lys  Glu Leu Glu Ala Lys  Val Gly Val
                1055                1060                1065
        Leu Ala Ile Asn Met Ser Leu  Ser Ile Ala Ala Thr  Val Ala Ser
                1070                1075                1080
        Ile Val Gly Ile Gly Ala Glu  Val Thr Ile Phe Leu  Leu Pro Ile
                1085                1090                1095
        Ala Gly Ile Ser Ala Gly Ile  Pro Ser Leu Val Asn  Asn Glu Leu
                1100                1105                1110
        Ile Leu His Asp Lys Ala Thr  Ser Val Val Asn Tyr  Phe Asn His
                1115                1120                1125
        Leu Ser Glu Ser Lys Lys Tyr  Gly Pro Leu Lys Thr  Glu Asp Asp
                1130                1135                1140
        Lys Ile Leu Val Pro Ile Asp  Asp Leu Val Ile Ser  Glu Ile Asp
                1145                1150                1155
        Phe Asn Asn Asn Ser Ile Lys  Leu Gly Thr Cys Asn  Ile Leu Ala
                1160                1165                1170
        Met Glu Gly Gly Ser Gly His  Thr Val Thr Gly Asn  Ile Asp His
                1175                1180                1185
        Phe Phe Ser Ser Pro Ser Ile  Ser Ser His Ile Pro  Ser Leu Ser
                1190                1195                1200
```

-continued

```
Ile Tyr Ser Ala Ile Gly Ile Glu Thr Glu Asn Leu Asp Phe Ser
1205                1210                1215

Lys Lys Ile Met Met Leu Pro Asn Ala Pro Ser Arg Val Phe Trp
1220                1225                1230

Trp Glu Thr Gly Ala Val Pro Gly Leu Arg Ser Leu Glu Asn Asp
1235                1240                1245

Gly Thr Arg Leu Leu Asp Ser Ile Arg Asp Leu Tyr Pro Gly Lys
1250                1255                1260

Phe Tyr Trp Arg Phe Tyr Ala Phe Phe Asp Tyr Ala Ile Thr Thr
1265                1270                1275

Leu Lys Pro Val Tyr Glu Asp Thr Asn Ile Lys Ile Lys Leu Asp
1280                1285                1290

Lys Asp Thr Arg Asn Phe Ile Met Pro Thr Ile Thr Thr Asn Glu
1295                1300                1305

Ile Arg Asn Lys Leu Ser Tyr Ser Phe Asp Gly Ala Gly Gly Thr
1310                1315                1320

Tyr Ser Leu Leu Leu Ser Ser Tyr Pro Ile Ser Thr Asn Ile Asn
1325                1330                1335

Leu Ser Lys Asp Asp Leu Trp Ile Phe Asn Ile Asp Asn Glu Val
1340                1345                1350

Arg Glu Ile Ser Ile Glu Asn Gly Thr Ile Lys Lys Gly Lys Leu
1355                1360                1365

Ile Lys Asp Val Leu Ser Lys Ile Asp Ile Asn Lys Asn Lys Leu
1370                1375                1380

Ile Ile Gly Asn Gln Thr Ile Asp Phe Ser Gly Asp Ile Asp Asn
1385                1390                1395

Lys Asp Arg Tyr Ile Phe Leu Thr Cys Glu Leu Asp Asp Lys Ile
1400                1405                1410

Ser Leu Ile Ile Glu Ile Asn Leu Val Ala Lys Ser Tyr Ser Leu
1415                1420                1425

Leu Leu Ser Gly Asp Lys Asn Tyr Leu Ile Ser Asn Leu Ser Asn
1430                1435                1440

Thr Ile Glu Lys Ile Asn Thr Leu Gly Leu Asp Ser Lys Asn Ile
1445                1450                1455

Ala Tyr Asn Tyr Thr Asp Glu Ser Asn Asn Lys Tyr Phe Gly Ala
1460                1465                1470

Ile Ser Lys Thr Ser Gln Lys Ser Ile Ile His Tyr Lys Lys Asp
1475                1480                1485

Ser Lys Asn Ile Leu Glu Phe Tyr Asn Asp Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asp Asn Ile Ser Phe Trp Lys
1580                1585                1590
```

```
Leu Phe Gly Phe Glu Asn Ile Asn Phe Val Ile Asp Lys Tyr Phe
    1595                1600                1605

Thr Leu Val Gly Lys Thr Asn Leu Gly Tyr Val Glu Phe Ile Cys
    1610                1615                1620

Asp Asn Asn Lys Asn Ile Asp Ile Tyr Phe Gly Glu Trp Lys Thr
    1625                1630                1635

Ser Ser Ser Lys Ser Thr Ile Phe Ser Gly Asn Gly Arg Asn Val
    1640                1645                1650

Val Val Glu Pro Ile Tyr Asn Pro Asp Thr Gly Glu Asp Ile Ser
    1655                1660                1665

Thr Ser Leu Asp Phe Ser Tyr Glu Pro Leu Tyr Gly Ile Asp Arg
    1670                1675                1680

Tyr Ile Asn Lys Val Leu Ile Ala Pro Asp Leu Tyr Thr Ser Leu
    1685                1690                1695

Ile Asn Ile Asn Thr Asn Tyr Tyr Ser Asn Glu Tyr Tyr Pro Glu
    1700                1705                1710

Ile Ile Val Leu Asn Pro Asn Thr Phe His Lys Lys Val Asn Ile
    1715                1720                1725

Asn Leu Asp Ser Ser Ser Phe Glu Tyr Lys Trp Ser Thr Glu Gly
    1730                1735                1740

Ser Asp Phe Ile Leu Val Arg Tyr Leu Glu Glu Ser Asn Lys Lys
    1745                1750                1755

Ile Leu Gln Lys Ile Arg Ile Lys Gly Ile Leu Ser Asn Thr Gln
    1760                1765                1770

Ser Phe Asn Lys Met Ser Ile Asp Phe Lys Asp Ile Lys Lys Leu
    1775                1780                1785

Ser Leu Gly Tyr Ile Met Ser Asn Phe Lys Ser Phe Asn Ser Glu
    1790                1795                1800

Asn Glu Leu Asp Arg Asp His Leu Gly Phe Lys Ile Ile Asp Asn
    1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Phe
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Leu Thr Ser Tyr Lys Ile Ile
    1865                1870                1875

Asn Gly Lys His Phe Tyr Phe Asn Asn Asp Gly Val Met Gln Leu
    1880                1885                1890

Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asn Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
```

-continued

```
            1985                1990                1995
Asp Thr Asp Thr Ala Ile Ala Phe Asn Gly Tyr Lys Thr Ile Asp
            2000                2005                2010
Gly Lys His Phe Tyr Phe Asp Ser Asp Cys Val Val Lys Ile Gly
            2015                2020                2025
Val Phe Ser Thr Ser Asn Gly Phe Glu Tyr Phe Ala Pro Ala Asn
            2030                2035                2040
Thr Tyr Asn Asn Asn Ile Glu Gly Gln Ala Ile Val Tyr Gln Ser
            2045                2050                2055
Lys Phe Leu Thr Leu Asn Gly Lys Lys Tyr Tyr Phe Asp Asn Asn
            2060                2065                2070
Ser Lys Ala Val Thr Gly Leu Gln Thr Ile Asp Ser Lys Lys Tyr
            2075                2080                2085
Tyr Phe Asn Thr Asn Thr Ala Glu Ala Ala Thr Gly Trp Gln Thr
            2090                2095                2100
Ile Asp Gly Lys Lys Tyr Tyr Phe Asn Thr Asn Thr Ala Glu Ala
            2105                2110                2115
Ala Thr Gly Trp Gln Thr Ile Asp Gly Lys Lys Tyr Tyr Phe Asn
            2120                2125                2130
Thr Asn Thr Ala Ile Ala Ser Thr Gly Tyr Thr Ile Ile Asn Gly
            2135                2140                2145
Lys His Phe Tyr Phe Asn Thr Asp Gly Ile Met Gln Ile Gly Val
            2150                2155                2160
Phe Lys Gly Pro Asn Gly Phe Glu Tyr Phe Ala Pro Ala Asn Thr
            2165                2170                2175
Asp Ala Asn Asn Ile Glu Gly Gln Ala Ile Leu Tyr Gln Asn Glu
            2180                2185                2190
Phe Leu Thr Leu Asn Gly Lys Lys Tyr Tyr Phe Gly Ser Asp Ser
            2195                2200                2205
Lys Ala Val Thr Gly Trp Arg Ile Ile Asn Asn Lys Lys Tyr Tyr
            2210                2215                2220
Phe Asn Pro Asn Asn Ala Ile Ala Ala Ile His Leu Cys Thr Ile
            2225                2230                2235
Asn Asn Asp Lys Tyr Tyr Phe Ser Tyr Asp Gly Ile Leu Gln Asn
            2240                2245                2250
Gly Tyr Ile Thr Ile Glu Arg Asn Asn Phe Tyr Phe Asp Ala Asn
            2255                2260                2265
Asn Glu Ser Lys Met Val Thr Gly Val Phe Lys Gly Pro Asn Gly
            2270                2275                2280
Phe Glu Tyr Phe Ala Pro Ala Asn Thr His Asn Asn Asn Ile Glu
            2285                2290                2295
Gly Gln Ala Ile Val Tyr Gln Asn Lys Phe Leu Thr Leu Asn Gly
            2300                2305                2310
Lys Lys Tyr Tyr Phe Asp Asn Asp Ser Lys Ala Val Thr Gly Trp
            2315                2320                2325
Gln Thr Ile Asp Gly Lys Lys Tyr Tyr Phe Asn Leu Asn Thr Ala
            2330                2335                2340
Glu Ala Ala Thr Gly Trp Gln Thr Ile Asp Gly Lys Lys Tyr Tyr
            2345                2350                2355
Phe Asn Leu Asn Thr Ala Glu Ala Ala Thr Gly Trp Gln Thr Ile
            2360                2365                2370
Asp Gly Lys Lys Tyr Tyr Phe Asn Thr Asn Thr Phe Ile Ala Ser
            2375                2380                2385
```

```
Thr Gly Tyr Thr Ser Ile Asn Gly Lys His Phe Tyr Phe Asn Thr
    2390                2395                2400

Asp Gly Ile Met Gln Ile Gly Val Phe Lys Gly Pro Asn Gly Phe
    2405                2410                2415

Glu Tyr Phe Ala Pro Ala Asn Thr Asp Ala Asn Asn Ile Glu Gly
    2420                2425                2430

Gln Ala Ile Leu Tyr Gln Asn Lys Phe Leu Thr Leu Asn Gly Lys
    2435                2440                2445

Lys Tyr Tyr Phe Gly Ser Asp Ser Lys Ala Val Thr Gly Leu Arg
    2450                2455                2460

Thr Ile Asp Gly Lys Lys Tyr Tyr Phe Asn Thr Asn Thr Ala Val
    2465                2470                2475

Ala Val Thr Gly Trp Gln Thr Ile Asn Gly Lys Lys Tyr Tyr Phe
    2480                2485                2490

Asn Thr Asn Thr Ser Ile Ala Ser Thr Gly Tyr Thr Ile Ile Ser
    2495                2500                2505

Gly Lys His Phe Tyr Phe Asn Thr Asp Gly Ile Met Gln Ile Gly
    2510                2515                2520

Val Phe Lys Gly Pro Asp Gly Phe Glu Tyr Phe Ala Pro Ala Asn
    2525                2530                2535

Thr Asp Ala Asn Asn Ile Glu Gly Gln Ala Ile Arg Tyr Gln Asn
    2540                2545                2550

Arg Phe Leu Tyr Leu His Asp Asn Ile Tyr Tyr Phe Gly Asn Asn
    2555                2560                2565

Ser Lys Ala Ala Thr Gly Trp Val Thr Ile Asp Gly Asn Arg Tyr
    2570                2575                2580

Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
    2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
    2690                2695                2700

Lys Ala Pro Gly Ile Tyr Gly
    2705                2710

<210> SEQ ID NO 2
<211> LENGTH: 2366
<212> TYPE: PRT
<213> ORGANISM: Clostridium difficile

<400> SEQUENCE: 2

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
```

```
            20                  25                  30
Glu Tyr His Asn Met Ser Glu Asn Thr Val Val Glu Lys Tyr Leu Lys
            35                  40                  45
Leu Lys Asp Ile Asn Ser Leu Thr Asp Ile Tyr Ile Asp Thr Tyr Lys
 50                  55                  60
Lys Ser Gly Arg Asn Lys Ala Leu Lys Lys Phe Lys Glu Tyr Leu Val
 65                  70                  75                  80
Thr Glu Val Leu Glu Leu Lys Asn Asn Asn Leu Thr Pro Val Glu Lys
                    85                  90                  95
Asn Leu His Phe Val Trp Ile Gly Gly Gln Ile Asn Asp Thr Ala Ile
                100                 105                 110
Asn Tyr Ile Asn Gln Trp Lys Asp Val Asn Ser Asp Tyr Asn Val Asn
                115                 120                 125
Val Phe Tyr Asp Ser Asn Ala Phe Leu Ile Asn Thr Leu Lys Lys Thr
                130                 135                 140
Val Val Glu Ser Ala Ile Asn Asp Thr Leu Glu Ser Phe Arg Glu Asn
145                 150                 155                 160
Leu Asn Asp Pro Arg Phe Asp Tyr Asn Lys Phe Phe Arg Lys Arg Met
                165                 170                 175
Glu Ile Ile Tyr Asp Lys Gln Lys Asn Phe Ile Asn Tyr Tyr Lys Ala
                180                 185                 190
Gln Arg Glu Glu Asn Pro Glu Leu Ile Ile Asp Asp Ile Val Lys Thr
                195                 200                 205
Tyr Leu Ser Asn Glu Tyr Ser Lys Glu Ile Asp Glu Leu Asn Thr Tyr
                210                 215                 220
Ile Glu Glu Ser Leu Asn Lys Ile Thr Gln Asn Ser Gly Asn Asp Val
225                 230                 235                 240
Arg Asn Phe Glu Glu Phe Lys Asn Gly Glu Ser Phe Asn Leu Tyr Glu
                245                 250                 255
Gln Glu Leu Val Glu Arg Trp Asn Leu Ala Ala Ala Ser Asp Ile Leu
                260                 265                 270
Arg Ile Ser Ala Leu Lys Glu Ile Gly Gly Met Tyr Leu Asp Val Asp
                275                 280                 285
Met Leu Pro Gly Ile Gln Pro Asp Leu Phe Glu Ser Ile Glu Lys Pro
                290                 295                 300
Ser Ser Val Thr Val Asp Phe Trp Glu Met Thr Lys Leu Glu Ala Ile
305                 310                 315                 320
Met Lys Tyr Lys Glu Tyr Ile Pro Glu Tyr Thr Ser Glu His Phe Asp
                325                 330                 335
Met Leu Asp Glu Glu Val Gln Ser Ser Phe Glu Ser Val Leu Ala Ser
                340                 345                 350
Lys Ser Asp Lys Ser Glu Ile Phe Ser Ser Leu Gly Asp Met Glu Ala
                355                 360                 365
Ser Pro Leu Glu Val Lys Ile Ala Phe Asn Ser Lys Gly Ile Ile Asn
                370                 375                 380
Gln Gly Leu Ile Ser Val Lys Asp Ser Tyr Cys Ser Asn Leu Ile Val
385                 390                 395                 400
Lys Gln Ile Glu Asn Arg Tyr Lys Ile Leu Asn Asn Ser Leu Asn Pro
                405                 410                 415
Ala Ile Ser Glu Asp Asn Asp Phe Asn Thr Thr Thr Asn Thr Phe Ile
                420                 425                 430
Asp Ser Ile Met Ala Glu Ala Asn Ala Asp Asn Gly Arg Phe Met Met
                435                 440                 445
```

```
Glu Leu Gly Lys Tyr Leu Arg Val Gly Phe Phe Pro Asp Val Lys Thr
            450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
            530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Asn Pro Gly
610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
            690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
            770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
            835                 840                 845

Ser Asp Ser Ile Asn Tyr Ile Lys Asp Glu Phe Lys Leu Ile Glu Ser
850                 855                 860
```

-continued

```
Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro
    1010                1015                1020

Thr Leu Ser Glu Gly Leu Pro Ile Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Thr Ala Thr Ala Ile Ile Thr Ser Ser Leu
    1070                1075                1080

Gly Ile Ala Ser Gly Phe Ser Ile Leu Val Pro Leu Ala Gly
    1085                1090                1095

Ile Ser Ala Gly Ile Pro Ser Leu Val Asn Asn Glu Leu Val Leu
    1100                1105                1110

Arg Asp Lys Ala Thr Lys Val Val Asp Tyr Phe Lys His Val Ser
    1115                1120                1125

Leu Val Glu Thr Glu Gly Val Phe Thr Leu Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Val Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
```

-continued

```
              1265                1270                1275
Lys Pro Arg Tyr Glu Asp Thr Asn Ile Arg Ile Asn Leu Asp Ser
              1280                1285                1290
Asn Thr Arg Ser Phe Ile Val Pro Ile Ile Thr Thr Glu Tyr Ile
              1295                1300                1305
Arg Glu Lys Leu Ser Tyr Ser Phe Tyr Gly Ser Gly Gly Thr Tyr
              1310                1315                1320
Ala Leu Ser Leu Ser Gln Tyr Asn Met Gly Ile Asn Ile Glu Leu
              1325                1330                1335
Ser Glu Ser Asp Val Trp Ile Ile Asp Val Asp Asn Val Val Arg
              1340                1345                1350
Asp Val Thr Ile Glu Ser Asp Lys Ile Lys Lys Gly Asp Leu Ile
              1355                1360                1365
Glu Gly Ile Leu Ser Thr Leu Ser Ile Glu Glu Asn Lys Ile Ile
              1370                1375                1380
Leu Asn Ser His Glu Ile Asn Phe Ser Gly Glu Val Asn Gly Ser
              1385                1390                1395
Asn Gly Phe Val Ser Leu Thr Phe Ser Ile Leu Glu Gly Ile Asn
              1400                1405                1410
Ala Ile Ile Glu Val Asp Leu Leu Ser Lys Ser Tyr Lys Leu Leu
              1415                1420                1425
Ile Ser Gly Glu Leu Lys Ile Leu Met Leu Asn Ser Asn His Ile
              1430                1435                1440
Gln Gln Lys Ile Asp Tyr Ile Gly Phe Asn Ser Glu Leu Gln Lys
              1445                1450                1455
Asn Ile Pro Tyr Ser Phe Val Asp Ser Glu Gly Lys Glu Asn Gly
              1460                1465                1470
Phe Ile Asn Gly Ser Thr Lys Glu Gly Leu Phe Val Ser Glu Leu
              1475                1480                1485
Pro Asp Val Val Leu Ile Ser Lys Val Tyr Met Asp Asp Ser Lys
              1490                1495                1500
Pro Ser Phe Gly Tyr Tyr Ser Asn Asn Leu Lys Asp Val Lys Val
              1505                1510                1515
Ile Thr Lys Asp Asn Val Asn Ile Leu Thr Gly Tyr Tyr Leu Lys
              1520                1525                1530
Asp Asp Ile Lys Ile Ser Leu Ser Leu Thr Leu Gln Asp Glu Lys
              1535                1540                1545
Thr Ile Lys Leu Asn Ser Val His Leu Asp Glu Ser Gly Val Ala
              1550                1555                1560
Glu Ile Leu Lys Phe Met Asn Arg Lys Gly Asn Thr Asn Thr Ser
              1565                1570                1575
Asp Ser Leu Met Ser Phe Leu Glu Ser Met Asn Ile Lys Ser Ile
              1580                1585                1590
Phe Val Asn Phe Leu Gln Ser Asn Ile Lys Phe Ile Leu Asp Ala
              1595                1600                1605
Asn Phe Ile Ile Ser Gly Thr Thr Ser Ile Gly Gln Phe Glu Phe
              1610                1615                1620
Ile Cys Asp Glu Asn Asp Asn Ile Gln Pro Tyr Phe Ile Lys Phe
              1625                1630                1635
Asn Thr Leu Glu Thr Asn Tyr Thr Leu Tyr Val Gly Asn Arg Gln
              1640                1645                1650
Asn Met Ile Val Glu Pro Asn Tyr Asp Leu Asp Asp Ser Gly Asp
              1655                1660                1665
```

```
Ile Ser Ser Thr Val Ile Asn Phe Ser Gln Lys Tyr Leu Tyr Gly
    1670                1675                1680

Ile Asp Ser Cys Val Asn Lys Val Val Ile Ser Pro Asn Ile Tyr
    1685                1690                1695

Thr Asp Glu Ile Asn Ile Thr Pro Val Tyr Glu Thr Asn Asn Thr
    1700                1705                1710

Tyr Pro Glu Val Ile Val Leu Asp Ala Asn Tyr Ile Asn Glu Lys
    1715                1720                1725

Ile Asn Val Asn Ile Asn Asp Leu Ser Ile Arg Tyr Val Trp Ser
    1730                1735                1740

Asn Asp Gly Asn Asp Phe Ile Leu Met Ser Thr Ser Glu Glu Asn
    1745                1750                1755

Lys Val Ser Gln Val Lys Ile Arg Phe Val Asn Val Phe Lys Asp
    1760                1765                1770

Lys Thr Leu Ala Asn Lys Leu Ser Phe Asn Phe Ser Asp Lys Gln
    1775                1780                1785

Asp Val Pro Val Ser Glu Ile Ile Leu Ser Phe Thr Pro Ser Tyr
    1790                1795                1800

Tyr Glu Asp Gly Leu Ile Gly Tyr Asp Leu Gly Leu Val Ser Leu
    1805                1810                1815

Tyr Asn Glu Lys Phe Tyr Ile Asn Asn Phe Gly Met Met Val Ser
    1820                1825                1830

Gly Leu Ile Tyr Ile Asn Asp Ser Leu Tyr Tyr Phe Lys Pro Pro
    1835                1840                1845

Val Asn Asn Leu Ile Thr Gly Phe Val Thr Val Gly Asp Asp Lys
    1850                1855                1860

Tyr Tyr Phe Asn Pro Ile Asn Gly Gly Ala Ala Ser Ile Gly Glu
    1865                1870                1875

Thr Ile Ile Asp Asp Lys Asn Tyr Tyr Phe Asn Gln Ser Gly Val
    1880                1885                1890

Leu Gln Thr Gly Val Phe Ser Thr Glu Asp Gly Phe Lys Tyr Phe
    1895                1900                1905

Ala Pro Ala Asn Thr Leu Asp Glu Asn Leu Glu Gly Glu Ala Ile
    1910                1915                1920

Asp Phe Thr Gly Lys Leu Ile Ile Asp Glu Asn Ile Tyr Tyr Phe
    1925                1930                1935

Asp Asp Asn Tyr Arg Gly Ala Val Glu Trp Lys Glu Leu Asp Gly
    1940                1945                1950

Glu Met His Tyr Phe Ser Pro Glu Thr Gly Lys Ala Phe Lys Gly
    1955                1960                1965

Leu Asn Gln Ile Gly Asp Tyr Lys Tyr Tyr Phe Asn Ser Asp Gly
    1970                1975                1980

Val Met Gln Lys Gly Phe Val Ser Ile Asn Asp Asn Lys His Tyr
    1985                1990                1995

Phe Asp Asp Ser Gly Val Met Lys Val Gly Tyr Thr Glu Ile Asp
    2000                2005                2010

Gly Lys His Phe Tyr Phe Ala Glu Asn Gly Glu Met Gln Ile Gly
    2015                2020                2025

Val Phe Asn Thr Glu Asp Gly Phe Lys Tyr Phe Ala His His Asn
    2030                2035                2040

Glu Asp Leu Gly Asn Glu Glu Gly Glu Glu Ile Ser Tyr Ser Gly
    2045                2050                2055
```

```
Ile Leu Asn Phe Asn Asn Lys Ile Tyr Tyr Phe Asp Asp Ser Phe
    2060            2065            2070

Thr Ala Val Val Gly Trp Lys Asp Leu Glu Asp Gly Ser Lys Tyr
    2075            2080            2085

Tyr Phe Asp Glu Asp Thr Ala Glu Ala Tyr Ile Gly Leu Ser Leu
    2090            2095            2100

Ile Asn Asp Gly Gln Tyr Tyr Phe Asn Asp Asp Gly Ile Met Gln
    2105            2110            2115

Val Gly Phe Val Thr Ile Asn Asp Lys Val Phe Tyr Phe Ser Asp
    2120            2125            2130

Ser Gly Ile Ile Glu Ser Gly Val Gln Asn Ile Asp Asp Asn Tyr
    2135            2140            2145

Phe Tyr Ile Asp Asp Asn Gly Ile Val Gln Ile Gly Val Phe Asp
    2150            2155            2160

Thr Ser Asp Gly Tyr Lys Tyr Phe Ala Pro Ala Asn Thr Val Asn
    2165            2170            2175

Asp Asn Ile Tyr Gly Gln Ala Val Glu Tyr Ser Gly Leu Val Arg
    2180            2185            2190

Val Gly Glu Asp Val Tyr Tyr Phe Gly Glu Thr Tyr Thr Ile Glu
    2195            2200            2205

Thr Gly Trp Ile Tyr Asp Met Glu Asn Glu Ser Asp Lys Tyr Tyr
    2210            2215            2220

Phe Asn Pro Glu Thr Lys Lys Ala Cys Lys Gly Ile Asn Leu Ile
    2225            2230            2235

Asp Asp Ile Lys Tyr Tyr Phe Asp Glu Lys Gly Ile Met Arg Thr
    2240            2245            2250

Gly Leu Ile Ser Phe Glu Asn Asn Asn Tyr Tyr Phe Asn Glu Asn
    2255            2260            2265

Gly Glu Met Gln Phe Gly Tyr Ile Asn Ile Glu Asp Lys Met Phe
    2270            2275            2280

Tyr Phe Gly Glu Asp Gly Val Met Gln Ile Gly Val Phe Asn Thr
    2285            2290            2295

Pro Asp Gly Phe Lys Tyr Phe Ala His Gln Asn Thr Leu Asp Glu
    2300            2305            2310

Asn Phe Glu Gly Glu Ser Ile Asn Tyr Thr Gly Trp Leu Asp Leu
    2315            2320            2325

Asp Glu Lys Arg Tyr Tyr Phe Thr Asp Glu Tyr Ile Ala Ala Thr
    2330            2335            2340

Gly Ser Val Ile Ile Asp Gly Glu Glu Tyr Tyr Phe Asp Pro Asp
    2345            2350            2355

Thr Ala Gln Leu Val Ile Ser Glu
    2360            2365

<210> SEQ ID NO 3
<211> LENGTH: 2710
<212> TYPE: PRT
<213> ORGANISM: Clostridium difficile

<400> SEQUENCE: 3

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Asn Glu Asn Lys Tyr Leu Gln Leu
            35                  40                  45
```

```
Lys Lys Leu Asn Glu Ser Ile Asp Val Phe Met Asn Lys Tyr Lys Asn
 50                  55                  60

Ser Ser Arg Asn Arg Ala Leu Ser Asn Leu Lys Lys Asp Ile Leu Lys
 65                  70                  75                  80

Glu Val Ile Leu Ile Lys Asn Ser Asn Thr Ser Pro Val Glu Lys Asn
                 85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
        130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Leu Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
                260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Pro Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460
```

```
Ile Ser Leu Ser Gly Pro Gly Ala Tyr Ala Ser Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Val Glu Glu Ala Gly Ser
                565                 570                 575

Lys Asn Tyr Val His Tyr Ile Ile Gln Leu Gln Gly Asp Asp Ile Ser
                580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asp Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
```

```
               885                 890                 895
Thr Tyr Ser Val Arg Phe Ile Asn Lys Ser Asn Gly Glu Ser Val Tyr
              900                 905                 910
Val Glu Thr Glu Lys Glu Ile Phe Ser Lys Tyr Ser Glu His Ile Thr
              915                 920                 925
Lys Glu Ile Ser Thr Ile Lys Asn Ser Ile Ile Thr Asp Val Asn Gly
              930                 935                 940
Asn Leu Leu Asp Asn Ile Gln Leu Asp His Thr Ser Gln Val Asn Thr
945                               950                 955                 960
Leu Asn Ala Ala Phe Phe Ile Gln Ser Leu Ile Asp Tyr Ser Ser Asn
                  965                 970                 975
Lys Asp Val Leu Asn Asp Leu Ser Thr Ser Val Lys Val Gln Leu Tyr
                  980                 985                 990
Ala Gln Leu Phe Ser Thr Gly Leu Asn Thr Ile Tyr Asp Ser Ile Gln
                  995                 1000                1005
Leu Val Asn Leu Ile Ser Asn Ala Val Asn Asp Thr Ile Asn Val
             1010                1015                1020
Leu Pro Thr Ile Thr Glu Gly Ile Pro Ile Val Ser Thr Ile Leu
             1025                1030                1035
Asp Gly Ile Asn Leu Gly Ala Ala Ile Lys Glu Leu Leu Asp Glu
             1040                1045                1050
His Asp Pro Leu Leu Lys Lys Glu Leu Glu Ala Lys Val Gly Val
             1055                1060                1065
Leu Ala Ile Asn Met Ser Leu Ser Ile Ala Ala Thr Val Ala Ser
             1070                1075                1080
Ile Val Gly Ile Gly Ala Glu Val Thr Ile Phe Leu Leu Pro Ile
             1085                1090                1095
Ala Gly Ile Ser Ala Gly Ile Pro Ser Leu Val Asn Asn Glu Leu
             1100                1105                1110
Ile Leu His Asp Lys Ala Thr Ser Val Val Asn Tyr Phe Asn His
             1115                1120                1125
Leu Ser Glu Ser Lys Glu Tyr Gly Pro Leu Lys Thr Glu Asp Asp
             1130                1135                1140
Lys Ile Leu Val Pro Ile Asp Asp Leu Val Ile Ser Glu Ile Asp
             1145                1150                1155
Phe Asn Asn Asn Ser Ile Lys Leu Gly Thr Cys Asn Ile Leu Ala
             1160                1165                1170
Met Glu Gly Gly Ser Gly His Thr Val Thr Gly Asn Ile Asp His
             1175                1180                1185
Phe Phe Ser Ser Pro Tyr Ile Ser Ser His Ile Pro Ser Leu Ser
             1190                1195                1200
Val Tyr Ser Ala Ile Gly Ile Lys Thr Glu Asn Leu Asp Phe Ser
             1205                1210                1215
Lys Lys Ile Met Met Leu Pro Asn Ala Pro Ser Arg Val Phe Trp
             1220                1225                1230
Trp Glu Thr Gly Ala Val Pro Gly Leu Arg Ser Leu Glu Asn Asn
             1235                1240                1245
Gly Thr Lys Leu Leu Asp Ser Ile Arg Asp Leu Tyr Pro Gly Lys
             1250                1255                1260
Phe Tyr Trp Arg Phe Tyr Ala Phe Phe Asp Tyr Ala Ile Thr Thr
             1265                1270                1275
Leu Lys Pro Val Tyr Glu Asp Thr Asn Thr Lys Ile Lys Leu Asp
             1280                1285                1290
```

-continued

Lys Asp Thr Arg Asn Phe Ile Met Pro Thr Ile Thr Thr Asp Glu
1295                1300                1305

Ile Arg Asn Lys Leu Ser Tyr Ser Phe Asp Gly Ala Gly Gly Thr
1310                1315                1320

Tyr Ser Leu Leu Leu Ser Ser Tyr Pro Ile Ser Met Asn Ile Asn
1325                1330                1335

Leu Ser Lys Asp Asp Leu Trp Ile Phe Asn Ile Asp Asn Glu Val
1340                1345                1350

Arg Glu Ile Ser Ile Glu Asn Gly Thr Ile Lys Lys Gly Asn Leu
1355                1360                1365

Ile Glu Asp Val Leu Ser Lys Ile Asp Ile Asn Lys Asn Lys Leu
1370                1375                1380

Ile Ile Gly Asn Gln Thr Ile Asp Phe Ser Gly Asp Ile Asp Asn
1385                1390                1395

Lys Asp Arg Tyr Ile Phe Leu Thr Cys Glu Leu Asp Asp Lys Ile
1400                1405                1410

Ser Leu Ile Ile Glu Ile Asn Leu Val Ala Lys Ser Tyr Ser Leu
1415                1420                1425

Leu Leu Ser Gly Asp Lys Asn Tyr Leu Ile Ser Asn Leu Ser Asn
1430                1435                1440

Thr Ile Glu Lys Ile Asn Thr Leu Gly Leu Asp Ser Lys Asn Ile
1445                1450                1455

Ala Tyr Asn Tyr Thr Asp Glu Ser Asn Asn Lys Tyr Phe Gly Ala
1460                1465                1470

Ile Ser Lys Thr Ser Gln Lys Ser Ile Ile His Tyr Lys Lys Asp
1475                1480                1485

Ser Lys Asn Ile Leu Glu Phe Tyr Asn Gly Ser Thr Leu Glu Phe
1490                1495                1500

Asn Ser Lys Asp Phe Ile Ala Glu Asp Ile Asn Val Phe Met Lys
1505                1510                1515

Asp Asp Ile Asn Thr Ile Thr Gly Lys Tyr Tyr Val Asp Asn Asn
1520                1525                1530

Thr Asp Lys Ser Ile Asp Phe Ser Ile Ser Leu Val Ser Lys Asn
1535                1540                1545

Gln Val Lys Val Asn Gly Leu Tyr Leu Asn Glu Ser Val Tyr Ser
1550                1555                1560

Ser Tyr Leu Asp Phe Val Lys Asn Ser Asp Gly His His Asn Thr
1565                1570                1575

Ser Asn Phe Met Asn Leu Phe Leu Asn Asn Ile Ser Phe Trp Lys
1580                1585                1590

Leu Phe Gly Phe Glu Asn Ile Asn Phe Val Ile Asp Lys Tyr Phe
1595                1600                1605

Thr Leu Val Gly Lys Thr Asn Leu Gly Tyr Val Glu Phe Ile Cys
1610                1615                1620

Asp Asn Asn Lys Asn Ile Asp Ile Tyr Phe Gly Glu Trp Lys Thr
1625                1630                1635

Ser Ser Ser Lys Ser Thr Ile Phe Ser Gly Asn Gly Arg Asn Val
1640                1645                1650

Val Val Glu Pro Ile Tyr Asn Pro Asp Thr Gly Glu Asp Ile Ser
1655                1660                1665

Thr Ser Leu Asp Phe Ser Tyr Glu Pro Leu Tyr Gly Ile Asp Arg
1670                1675                1680

```
Tyr Ile Asn Lys Val Leu Ile Ala Pro Asp Leu Tyr Thr Ser Leu
    1685                1690                1695

Ile Asn Ile Asn Thr Asn Tyr Tyr Ser Asn Glu Tyr Tyr Pro Glu
    1700                1705                1710

Ile Ile Val Leu Asn Pro Asn Thr Phe His Lys Lys Val Asn Ile
    1715                1720                1725

Asn Leu Asp Ser Ser Ser Phe Glu Tyr Lys Trp Ser Thr Glu Gly
    1730                1735                1740

Ser Asp Phe Ile Leu Val Arg Tyr Leu Glu Glu Ser Asn Lys Lys
    1745                1750                1755

Ile Leu Gln Lys Ile Arg Ile Lys Gly Ile Leu Ser Asn Thr Gln
    1760                1765                1770

Ser Phe Asn Lys Met Ser Ile Asp Phe Lys Asp Ile Lys Lys Leu
    1775                1780                1785

Ser Leu Gly Tyr Ile Met Ser Asn Phe Lys Ser Phe Asn Ser Glu
    1790                1795                1800

Asn Glu Leu Asp Arg Asp His Leu Gly Phe Lys Ile Ile Asp Asn
    1805                1810                1815

Lys Thr Tyr Tyr Tyr Asp Glu Asp Ser Lys Leu Val Lys Gly Leu
    1820                1825                1830

Ile Asn Ile Asn Asn Ser Leu Phe Tyr Phe Asp Pro Ile Glu Ser
    1835                1840                1845

Asn Leu Val Thr Gly Trp Gln Thr Ile Asn Gly Lys Lys Tyr Tyr
    1850                1855                1860

Phe Asp Ile Asn Thr Gly Ala Ala Ser Thr Ser Tyr Lys Ile Ile
    1865                1870                1875

Asn Gly Lys His Phe Tyr Phe Asn Asn Asn Gly Val Met Gln Leu
    1880                1885                1890

Gly Val Phe Lys Gly Pro Asp Gly Phe Glu Tyr Phe Ala Pro Ala
    1895                1900                1905

Asn Thr Gln Asn Asn Asn Ile Glu Gly Gln Ala Ile Val Tyr Gln
    1910                1915                1920

Ser Lys Phe Leu Thr Leu Asn Gly Lys Lys Tyr Tyr Phe Asp Asn
    1925                1930                1935

Asp Ser Lys Ala Val Thr Gly Trp Arg Ile Ile Asn Asn Glu Lys
    1940                1945                1950

Tyr Tyr Phe Asn Pro Asn Asn Ala Ile Ala Ala Val Gly Leu Gln
    1955                1960                1965

Val Ile Asp Asn Asn Lys Tyr Tyr Phe Asn Pro Asp Thr Ala Ile
    1970                1975                1980

Ile Ser Lys Gly Trp Gln Thr Val Asn Gly Ser Arg Tyr Tyr Phe
    1985                1990                1995

Asp Thr Asp Thr Ala Ile Ala Phe Asn Gly Tyr Lys Thr Ile Asp
    2000                2005                2010

Gly Lys His Phe Tyr Phe Asp Ser Asp Cys Val Val Lys Ile Gly
    2015                2020                2025

Val Phe Ser Gly Ser Asn Gly Phe Glu Tyr Phe Ala Pro Ala Asn
    2030                2035                2040

Thr Tyr Asn Asn Asn Ile Glu Gly Gln Ala Ile Val Tyr Gln Ser
    2045                2050                2055

Lys Phe Leu Thr Leu Asn Gly Lys Lys Tyr Tyr Phe Asp Asn Asn
    2060                2065                2070

Ser Lys Ala Val Thr Gly Trp Gln Thr Ile Asp Ser Lys Lys Tyr
```

```
               2075                2080                2085
Tyr Phe Asn Thr Asn Thr Ala Glu Ala Ala Thr Gly Trp Gln Thr
        2090                2095                2100
Ile Asp Gly Lys Lys Tyr Tyr Phe Asn Thr Asn Thr Ala Glu Ala
        2105                2110                2115
Ala Thr Gly Trp Gln Thr Ile Asp Gly Lys Lys Tyr Tyr Phe Asn
        2120                2125                2130
Thr Asn Thr Ser Ile Ala Ser Thr Gly Tyr Thr Ile Ile Asn Gly
        2135                2140                2145
Lys Tyr Phe Tyr Phe Asn Thr Asp Gly Ile Met Gln Ile Gly Val
        2150                2155                2160
Phe Lys Val Pro Asn Gly Phe Glu Tyr Phe Ala Pro Ala Asn Thr
        2165                2170                2175
His Asn Asn Asn Ile Glu Gly Gln Ala Ile Leu Tyr Gln Asn Lys
        2180                2185                2190
Phe Leu Thr Leu Asn Gly Lys Lys Tyr Tyr Phe Gly Ser Asp Ser
        2195                2200                2205
Lys Ala Ile Thr Gly Trp Gln Thr Ile Asp Gly Lys Lys Tyr Tyr
        2210                2215                2220
Phe Asn Pro Asn Asn Ala Ile Ala Ala Thr His Leu Cys Thr Ile
        2225                2230                2235
Asn Asn Asp Lys Tyr Tyr Phe Ser Tyr Asp Gly Ile Leu Gln Asn
        2240                2245                2250
Gly Tyr Ile Thr Ile Glu Arg Asn Asn Phe Tyr Phe Asp Ala Asn
        2255                2260                2265
Asn Glu Ser Lys Met Val Thr Gly Val Phe Lys Gly Pro Asn Gly
        2270                2275                2280
Phe Glu Tyr Phe Ala Pro Ala Asn Thr His Asn Asn Asn Ile Glu
        2285                2290                2295
Gly Gln Ala Ile Val Tyr Gln Asn Lys Phe Leu Thr Leu Asn Gly
        2300                2305                2310
Lys Lys Tyr Tyr Phe Asp Asn Asp Ser Lys Ala Val Thr Gly Trp
        2315                2320                2325
Gln Thr Ile Asp Ser Lys Lys Tyr Tyr Phe Asn Leu Asn Thr Ala
        2330                2335                2340
Val Ala Val Thr Gly Trp Gln Thr Ile Asp Gly Glu Lys Tyr Tyr
        2345                2350                2355
Phe Asn Leu Asn Thr Ala Glu Ala Ala Thr Gly Trp Gln Thr Ile
        2360                2365                2370
Asp Gly Lys Arg Tyr Tyr Phe Asn Thr Asn Thr Tyr Ile Ala Ser
        2375                2380                2385
Thr Gly Tyr Thr Ile Ile Asn Gly Lys His Phe Tyr Phe Asn Thr
        2390                2395                2400
Asp Gly Ile Met Gln Ile Gly Val Phe Lys Gly Pro Asp Gly Phe
        2405                2410                2415
Glu Tyr Phe Ala Pro Ala Asn Thr His Asn Asn Asn Ile Glu Gly
        2420                2425                2430
Gln Ala Ile Leu Tyr Gln Asn Lys Phe Leu Thr Leu Asn Gly Lys
        2435                2440                2445
Lys Tyr Tyr Phe Gly Ser Asp Ser Lys Ala Val Thr Gly Leu Arg
        2450                2455                2460
Thr Ile Asp Gly Lys Lys Tyr Tyr Phe Asn Thr Asn Thr Ala Val
        2465                2470                2475
```

Ala Val Thr Gly Trp Gln Thr Ile Asn Gly Lys Lys Tyr Tyr Phe
2480                2485                2490

Asn Thr Asn Thr Tyr Ile Ala Ser Thr Gly Tyr Thr Ile Ile Ser
2495                2500                2505

Gly Lys His Phe Tyr Phe Asn Thr Asp Gly Ile Met Gln Ile Gly
2510                2515                2520

Val Phe Lys Gly Pro Asp Gly Phe Glu Tyr Phe Ala Pro Ala Asn
2525                2530                2535

Thr Asp Ala Asn Asn Ile Glu Gly Gln Ala Ile Arg Tyr Gln Asn
2540                2545                2550

Arg Phe Leu Tyr Leu His Asp Asn Ile Tyr Phe Gly Asn Asp
2555                2560                2565

Ser Lys Ala Ala Thr Gly Trp Ala Thr Ile Asp Gly Asn Arg Tyr
2570                2575                2580

Tyr Phe Glu Pro Asn Thr Ala Met Gly Ala Asn Gly Tyr Lys Thr
2585                2590                2595

Ile Asp Asn Lys Asn Phe Tyr Phe Arg Asn Gly Leu Pro Gln Ile
2600                2605                2610

Gly Val Phe Lys Gly Pro Asn Gly Phe Glu Tyr Phe Ala Pro Ala
2615                2620                2625

Asn Thr Asp Ala Asn Asn Ile Asp Gly Gln Ala Ile Arg Tyr Gln
2630                2635                2640

Asn Arg Phe Leu His Leu Leu Gly Lys Ile Tyr Tyr Phe Gly Asn
2645                2650                2655

Asn Ser Lys Ala Val Thr Gly Trp Gln Thr Ile Asn Ser Lys Val
2660                2665                2670

Tyr Tyr Phe Met Pro Asp Thr Ala Met Ala Ala Ala Gly Gly Leu
2675                2680                2685

Phe Glu Ile Asp Gly Val Ile Tyr Phe Phe Gly Val Asp Gly Val
2690                2695                2700

Lys Ala Pro Gly Ile Tyr Gly
2705                2710

<210> SEQ ID NO 4
<211> LENGTH: 2366
<212> TYPE: PRT
<213> ORGANISM: Clostridium difficile

<400> SEQUENCE: 4

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn

```
                115                 120                 125
Val Phe Tyr Asp Ser Asn Ala Phe Leu Ile Asn Thr Leu Lys Lys Thr
130                 135                 140

Ile Val Glu Ser Ala Thr Asn Asp Thr Leu Glu Ser Phe Arg Glu Asn
145                 150                 155                 160

Leu Asn Asp Pro Arg Phe Asp Tyr Asn Lys Phe Tyr Arg Lys Arg Met
                165                 170                 175

Glu Ile Ile Tyr Asp Lys Gln Lys Asn Phe Ile Asn Tyr Tyr Lys Thr
                180                 185                 190

Gln Arg Glu Glu Asn Pro Asp Leu Ile Ile Asp Asp Ile Val Lys Ile
                195                 200                 205

Tyr Leu Ser Asn Glu Tyr Ser Lys Asp Ile Asp Glu Leu Asn Ser Tyr
210                 215                 220

Ile Glu Glu Ser Leu Asn Lys Val Thr Glu Asn Ser Gly Asn Asp Val
225                 230                 235                 240

Arg Asn Phe Glu Glu Phe Lys Gly Gly Glu Ser Phe Lys Leu Tyr Glu
                245                 250                 255

Gln Glu Leu Val Glu Arg Trp Asn Leu Ala Ala Ala Ser Asp Ile Leu
                260                 265                 270

Arg Ile Ser Ala Leu Lys Glu Val Gly Gly Val Tyr Leu Asp Val Asp
                275                 280                 285

Met Leu Pro Gly Ile Gln Pro Asp Leu Phe Glu Ser Ile Glu Lys Pro
290                 295                 300

Ser Ser Val Thr Val Asp Phe Trp Glu Met Val Lys Leu Glu Ala Ile
305                 310                 315                 320

Met Lys Tyr Lys Glu Tyr Ile Pro Gly Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
                355                 360                 365

Ser Pro Leu Glu Val Lys Ile Ala Phe Asn Ser Lys Gly Ile Ile Asn
                370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Ala Phe Ile
                420                 425                 430

Asp Ser Ile Met Ala Glu Ala Asn Ala Asp Asn Gly Arg Phe Met Met
                435                 440                 445

Glu Leu Gly Lys Tyr Leu Arg Val Gly Phe Phe Pro Asp Val Lys Thr
450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
                515                 520                 525

Ala Gln Phe Glu Glu Tyr Lys Lys Asn Tyr Phe Glu Gly Ser Leu Gly
530                 535                 540
```

```
Glu Asp Asp Asn Leu Asp Phe Ser Gln Asn Thr Val Asp Lys Glu
545                 550                 555                 560

Tyr Leu Leu Glu Lys Ile Ser Ser Leu Ala Arg Ser Ser Glu Arg Gly
            565                 570                 575

Tyr Ile His Tyr Ile Val Gln Leu Gln Gly Asp Lys Ile Ser Tyr Glu
                580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Tyr Asn Pro Gly
            610                 615                 620

Asp Gly Glu Ile Gln Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Leu Asp Val Asp Ser Leu Ser
                660                 665                 670

Thr Glu Ile Glu Thr Ala Ile Asp Leu Ala Lys Glu Asp Ile Ser Pro
                675                 680                 685

Lys Ser Ile Glu Ile Asn Leu Leu Gly Cys Asn Met Phe Ser Tyr Ser
            690                 695                 700

Val Asn Val Glu Glu Thr Tyr Pro Gly Lys Leu Leu Leu Arg Val Lys
705                 710                 715                 720

Asp Lys Val Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
770                 775                 780

Asn Lys Ile Ile Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Ala Glu Cys Glu Ile Asn Val Ile Ser Asn Ile
                820                 825                 830

Asp Thr Gln Val Val Glu Gly Arg Ile Glu Glu Ala Lys Ser Leu Thr
            835                 840                 845

Ser Asp Ser Ile Asn Tyr Ile Lys Asn Glu Phe Lys Leu Ile Glu Ser
850                 855                 860

Ile Ser Asp Ala Leu Tyr Asp Leu Lys Gln Gln Asn Glu Leu Glu Glu
865                 870                 875                 880

Ser His Phe Ile Ser Phe Glu Asp Ile Leu Glu Thr Asp Glu Gly Phe
            885                 890                 895

Ser Ile Arg Phe Ile Asp Lys Glu Thr Gly Glu Ser Ile Phe Val Glu
            900                 905                 910

Thr Glu Lys Ala Ile Phe Ser Glu Tyr Ala Asn His Ile Thr Glu Glu
            915                 920                 925

Ile Ser Lys Ile Lys Gly Thr Ile Phe Asp Thr Val Asn Gly Lys Leu
            930                 935                 940

Val Lys Lys Val Asn Leu Asp Ala Thr His Glu Val Asn Thr Leu Asn
945                 950                 955                 960
```

Ala Ala Phe Phe Ile Gln Ser Leu Ile Glu Tyr Asn Ser Ser Lys Glu
            965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
            995                 1000                1005

Glu Leu Val Ser Thr Ala Leu Asp Glu Thr Ile Asp Leu Leu Pro
    1010                1015                1020

Thr Leu Ser Glu Gly Leu Pro Val Ile Ala Thr Ile Ile Asp Gly
    1025                1030                1035

Val Ser Leu Gly Ala Ala Ile Lys Glu Leu Ser Glu Thr Ser Asp
    1040                1045                1050

Pro Leu Leu Arg Gln Glu Ile Glu Ala Lys Ile Gly Ile Met Ala
    1055                1060                1065

Val Asn Leu Thr Ala Ala Thr Thr Ala Ile Ile Thr Ser Ser Leu
    1070                1075                1080

Gly Ile Ala Ser Gly Phe Ser Ile Leu Leu Val Pro Leu Ala Gly
    1085                1090                1095

Ile Ser Ala Gly Ile Pro Ser Leu Val Asn Asn Glu Leu Ile Leu
    1100                1105                1110

Arg Asp Lys Ala Thr Lys Val Val Asp Tyr Phe Ser His Ile Ser
    1115                1120                1125

Leu Ala Glu Ser Glu Gly Ala Phe Thr Ser Leu Asp Asp Lys Ile
    1130                1135                1140

Met Met Pro Gln Asp Asp Leu Val Ile Ser Glu Ile Asp Phe Asn
    1145                1150                1155

Asn Asn Ser Ile Thr Leu Gly Lys Cys Glu Ile Trp Arg Met Glu
    1160                1165                1170

Gly Gly Ser Gly His Thr Val Thr Asp Asp Ile Asp His Phe Phe
    1175                1180                1185

Ser Ala Pro Ser Ile Thr Tyr Arg Glu Pro His Leu Ser Ile Tyr
    1190                1195                1200

Asp Val Leu Glu Val Gln Lys Glu Glu Leu Asp Leu Ser Lys Asp
    1205                1210                1215

Leu Met Val Leu Pro Asn Ala Pro Asn Arg Val Phe Ala Trp Glu
    1220                1225                1230

Thr Gly Trp Thr Pro Gly Leu Arg Ser Leu Glu Asn Asp Gly Thr
    1235                1240                1245

Lys Leu Leu Asp Arg Ile Arg Asp Asn Tyr Glu Gly Glu Phe Tyr
    1250                1255                1260

Trp Arg Tyr Phe Ala Phe Ile Ala Asp Ala Leu Ile Thr Thr Leu
    1265                1270                1275

Lys Pro Arg Tyr Glu Asp Thr Asn Ile Arg Ile Asn Leu Asp Ser
    1280                1285                1290

Asn Thr Arg Ser Phe Ile Val Pro Val Ile Thr Thr Glu Tyr Ile
    1295                1300                1305

Arg Glu Lys Leu Ser Tyr Ser Phe Tyr Gly Ser Gly Gly Thr Tyr
    1310                1315                1320

Ala Leu Ser Leu Ser Gln Tyr Asn Met Asn Ile Asn Ile Glu Leu
    1325                1330                1335

Asn Glu Asn Asp Thr Trp Val Ile Asp Val Asp Asn Val Val Arg
    1340                1345                1350

Asp Val Thr Ile Glu Ser Asp Lys Ile Lys Lys Gly Asp Leu Ile

-continued

```
            1355                1360                1365
Glu Asn Ile Leu Ser Lys Leu Ser Ile Glu Asp Asn Lys Ile Ile
            1370                1375                1380
Leu Asp Asn His Glu Ile Asn Phe Ser Gly Thr Leu Asn Gly Gly
            1385                1390                1395
Asn Gly Phe Val Ser Leu Thr Phe Ser Ile Leu Glu Gly Ile Asn
            1400                1405                1410
Ala Val Ile Glu Val Asp Leu Leu Ser Lys Ser Tyr Lys Val Leu
            1415                1420                1425
Ile Ser Gly Glu Leu Lys Thr Leu Met Ala Asn Ser Asn Ser Val
            1430                1435                1440
Gln Gln Lys Ile Asp Tyr Ile Gly Leu Asn Ser Glu Leu Gln Lys
            1445                1450                1455
Asn Ile Pro Tyr Ser Phe Met Asp Asp Lys Gly Lys Glu Asn Gly
            1460                1465                1470
Phe Ile Asn Cys Ser Thr Lys Glu Gly Leu Phe Val Ser Glu Leu
            1475                1480                1485
Ser Asp Val Val Leu Ile Ser Lys Val Tyr Met Asp Asn Ser Lys
            1490                1495                1500
Pro Leu Phe Gly Tyr Cys Ser Asn Asp Leu Lys Asp Val Lys Val
            1505                1510                1515
Ile Thr Lys Asp Asp Val Ile Ile Leu Thr Gly Tyr Tyr Leu Lys
            1520                1525                1530
Asp Asp Ile Lys Ile Ser Leu Ser Phe Thr Ile Gln Asp Glu Asn
            1535                1540                1545
Thr Ile Lys Leu Asn Gly Val Tyr Leu Asp Glu Asn Gly Val Ala
            1550                1555                1560
Glu Ile Leu Lys Phe Met Asn Lys Lys Gly Ser Thr Asn Thr Ser
            1565                1570                1575
Asp Ser Leu Met Ser Phe Leu Glu Ser Met Asn Ile Lys Ser Ile
            1580                1585                1590
Phe Ile Asn Ser Leu Gln Ser Asn Thr Lys Leu Ile Leu Asp Thr
            1595                1600                1605
Asn Phe Ile Ile Ser Gly Thr Thr Ser Ile Gly Gln Phe Glu Phe
            1610                1615                1620
Ile Cys Asp Lys Asp Asn Asn Ile Gln Pro Tyr Phe Ile Lys Phe
            1625                1630                1635
Asn Thr Leu Glu Thr Lys Tyr Thr Leu Tyr Val Gly Asn Arg Gln
            1640                1645                1650
Asn Met Ile Val Glu Pro Asn Tyr Asp Leu Asp Asp Ser Gly Asp
            1655                1660                1665
Ile Ser Ser Thr Val Ile Asn Phe Ser Gln Lys Tyr Leu Tyr Gly
            1670                1675                1680
Ile Asp Ser Cys Val Asn Lys Val Ile Ile Ser Pro Asn Ile Tyr
            1685                1690                1695
Thr Asp Glu Ile Asn Ile Thr Pro Ile Tyr Glu Ala Asn Asn Thr
            1700                1705                1710
Tyr Pro Glu Val Ile Val Leu Asp Thr Asn Tyr Ile Ser Glu Lys
            1715                1720                1725
Ile Asn Ile Asn Ile Asn Asp Leu Ser Ile Arg Tyr Val Trp Ser
            1730                1735                1740
Asn Asp Gly Ser Asp Phe Ile Leu Met Ser Thr Asp Glu Glu Asn
            1745                1750                1755
```

-continued

```
Lys Val Ser Gln Val Lys Ile Arg Phe Thr Asn Val Phe Lys Gly
    1760                1765                1770

Asn Thr Ile Ser Asp Lys Ile Ser Phe Asn Phe Ser Asp Lys Gln
    1775                1780                1785

Asp Val Ser Ile Asn Lys Val Ile Ser Thr Phe Thr Pro Ser Tyr
    1790                1795                1800

Tyr Val Glu Gly Leu Leu Asn Tyr Asp Leu Gly Leu Ile Ser Leu
    1805                1810                1815

Tyr Asn Glu Lys Phe Tyr Ile Asn Asn Phe Gly Met Met Val Ser
    1820                1825                1830

Gly Leu Val Tyr Ile Asn Asp Ser Leu Tyr Tyr Phe Lys Pro Pro
    1835                1840                1845

Ile Lys Asn Leu Ile Thr Gly Phe Thr Thr Ile Gly Asp Asp Lys
    1850                1855                1860

Tyr Tyr Phe Asn Pro Asp Asn Gly Gly Ala Ala Ser Val Gly Glu
    1865                1870                1875

Thr Ile Ile Asp Gly Lys Asn Tyr Tyr Phe Ser Gln Asn Gly Val
    1880                1885                1890

Leu Gln Thr Gly Val Phe Ser Thr Glu Asp Gly Phe Lys Tyr Phe
    1895                1900                1905

Ala Pro Ala Asp Thr Leu Asp Glu Asn Leu Glu Gly Glu Ala Ile
    1910                1915                1920

Asp Phe Thr Gly Lys Leu Thr Ile Asp Glu Asn Val Tyr Tyr Phe
    1925                1930                1935

Gly Asp Asn Tyr Arg Ala Ala Ile Glu Trp Gln Thr Leu Asp Asp
    1940                1945                1950

Glu Val Tyr Tyr Phe Ser Thr Asp Thr Gly Arg Ala Phe Lys Gly
    1955                1960                1965

Leu Asn Gln Ile Gly Asp Asp Lys Phe Tyr Phe Asn Ser Asp Gly
    1970                1975                1980

Ile Met Gln Lys Gly Phe Val Asn Ile Asn Asp Lys Thr Phe Tyr
    1985                1990                1995

Phe Asp Asp Ser Gly Val Met Lys Ser Gly Tyr Thr Glu Ile Asp
    2000                2005                2010

Gly Lys Tyr Phe Tyr Phe Ala Glu Asn Gly Glu Met Gln Ile Gly
    2015                2020                2025

Val Phe Asn Thr Ala Asp Gly Phe Lys Tyr Phe Ala His His Asp
    2030                2035                2040

Glu Asp Leu Gly Asn Glu Glu Gly Glu Ala Leu Ser Tyr Ser Gly
    2045                2050                2055

Ile Leu Asn Phe Asn Asn Lys Ile Tyr Tyr Phe Asp Asp Ser Phe
    2060                2065                2070

Thr Ala Val Val Gly Trp Lys Asp Leu Glu Asp Gly Ser Lys Tyr
    2075                2080                2085

Tyr Phe Asp Glu Asp Thr Ala Glu Ala Tyr Ile Gly Ile Ser Ile
    2090                2095                2100

Ile Asn Asp Gly Lys Tyr Tyr Phe Asn Asp Ser Gly Ile Met Gln
    2105                2110                2115

Ile Gly Phe Val Thr Ile Asn Asn Glu Val Phe Tyr Phe Ser Asp
    2120                2125                2130

Ser Gly Ile Val Glu Ser Gly Met Gln Asn Ile Asp Asp Asn Tyr
    2135                2140                2145
```

```
Phe Tyr Ile Asp Glu Asn Gly Leu Val Gln Ile Gly Val Phe Asp
            2150                2155                2160

Thr Ser Asp Gly Tyr Lys Tyr Phe Ala Pro Ala Asn Thr Val Asn
        2165                2170                2175

Asp Asn Ile Tyr Gly Gln Ala Val Glu Tyr Ser Gly Leu Val Arg
        2180                2185                2190

Val Gly Glu Asp Val Tyr Tyr Phe Gly Glu Thr Tyr Thr Ile Glu
        2195                2200                2205

Thr Gly Trp Ile Tyr Asp Met Glu Asn Glu Ser Asp Lys Tyr Tyr
        2210                2215                2220

Phe Asp Pro Glu Thr Lys Lys Ala Tyr Lys Gly Ile Asn Val Ile
        2225                2230                2235

Asp Asp Ile Lys Tyr Tyr Phe Asp Glu Asn Gly Ile Met Arg Thr
        2240                2245                2250

Gly Leu Ile Thr Phe Glu Asp Asn His Tyr Tyr Phe Asn Glu Asp
        2255                2260                2265

Gly Ile Met Gln Tyr Gly Tyr Leu Asn Ile Glu Asp Lys Thr Phe
        2270                2275                2280

Tyr Phe Ser Glu Asp Gly Ile Met Gln Ile Gly Val Phe Asn Thr
        2285                2290                2295

Pro Asp Gly Phe Lys Tyr Phe Ala His Gln Asn Thr Leu Asp Glu
        2300                2305                2310

Asn Phe Glu Gly Glu Ser Ile Asn Tyr Thr Gly Trp Leu Asp Leu
        2315                2320                2325

Asp Glu Lys Arg Tyr Tyr Phe Thr Asp Glu Tyr Ile Ala Ala Thr
        2330                2335                2340

Gly Ser Val Ile Ile Asp Gly Glu Glu Tyr Tyr Phe Asp Pro Asp
        2345                2350                2355

Thr Ala Gln Leu Val Ile Ser Glu
        2360                2365

<210> SEQ ID NO 5
<211> LENGTH: 460
<212> TYPE: PRT
<213> ORGANISM: Clostridium difficile

<400> SEQUENCE: 5

Met Lys Lys Phe Arg Lys His Lys Arg Ile Ser Asn Cys Ile Ser Ile
1               5                   10                  15

Leu Leu Ile Leu Tyr Leu Thr Leu Gly Gly Leu Leu Pro Asn Asn Ile
            20                  25                  30

Tyr Ala Gln Asp Leu Gln Ser Tyr Ser Glu Lys Val Cys Asn Thr Thr
        35                  40                  45

Tyr Lys Ala Pro Ile Glu Ser Phe Leu Lys Asp Lys Glu Lys Ala Lys
    50                  55                  60

Glu Trp Glu Arg Lys Glu Ala Glu Arg Ile Glu Gln Lys Leu Glu Arg
65                  70                  75                  80

Ser Glu Lys Glu Ala Leu Glu Ser Tyr Lys Lys Asp Ser Val Glu Ile
                85                  90                  95

Ser Lys Tyr Ser Gln Thr Arg Asn Tyr Phe Tyr Asp Tyr Gln Ile Glu
            100                 105                 110

Ala Asn Ser Arg Glu Lys Glu Tyr Lys Glu Leu Arg Asn Ala Ile Ser
        115                 120                 125

Lys Asn Lys Ile Asp Lys Pro Met Tyr Val Tyr Tyr Phe Glu Ser Pro
    130                 135                 140
```

```
Glu Lys Phe Ala Phe Asn Lys Val Ile Arg Thr Glu Asn Gln Asn Glu
145                 150                 155                 160

Ile Ser Leu Glu Lys Phe Asn Glu Phe Lys Glu Thr Ile Gln Asn Lys
            165                 170                 175

Leu Phe Lys Gln Asp Gly Phe Lys Asp Ile Ser Leu Tyr Glu Pro Gly
        180                 185                 190

Lys Gly Asp Glu Lys Pro Thr Pro Leu Leu Met His Leu Lys Leu Pro
    195                 200                 205

Arg Asn Thr Gly Met Leu Pro Tyr Thr Asn Thr Asn Asn Val Ser Thr
210                 215                 220

Leu Ile Glu Gln Gly Tyr Ser Ile Lys Ile Asp Lys Ile Val Arg Ile
225                 230                 235                 240

Val Ile Asp Gly Lys His Tyr Ile Lys Ala Glu Ala Ser Val Val Asn
                245                 250                 255

Ser Leu Asp Phe Lys Asp Asp Val Ser Lys Gly Asp Ser Trp Gly Lys
            260                 265                 270

Ala Asn Tyr Asn Asp Trp Ser Asn Lys Leu Thr Pro Asn Glu Leu Ala
        275                 280                 285

Asp Val Asn Asp Tyr Met Arg Gly Gly Tyr Thr Ala Ile Asn Asn Tyr
    290                 295                 300

Leu Ile Ser Asn Gly Pro Val Asn Asn Pro Asn Pro Glu Leu Asp Ser
305                 310                 315                 320

Lys Ile Thr Asn Ile Glu Asn Ala Leu Lys Arg Glu Pro Ile Pro Thr
                325                 330                 335

Asn Leu Thr Val Tyr Arg Arg Ser Gly Pro Gln Glu Phe Gly Leu Thr
            340                 345                 350

Leu Thr Ser Pro Glu Tyr Asp Phe Asn Lys Leu Glu Asn Ile Asp Ala
        355                 360                 365

Phe Lys Ser Lys Trp Glu Gly Gln Ala Leu Ser Tyr Pro Asn Phe Ile
    370                 375                 380

Ser Thr Ser Ile Gly Ser Val Asn Met Ser Ala Phe Ala Lys Arg Lys
385                 390                 395                 400

Ile Val Leu Arg Ile Thr Ile Pro Lys Gly Ser Pro Gly Ala Tyr Leu
                405                 410                 415

Ser Ala Ile Pro Gly Tyr Ala Gly Glu Tyr Glu Val Leu Leu Asn His
            420                 425                 430

Gly Ser Lys Phe Lys Ile Asn Lys Ile Asp Ser Tyr Lys Asp Gly Thr
        435                 440                 445

Ile Thr Lys Leu Ile Val Asp Ala Thr Leu Ile Pro
    450                 455                 460

<210> SEQ ID NO 6
<211> LENGTH: 876
<212> TYPE: PRT
<213> ORGANISM: Clostridium difficile

<400> SEQUENCE: 6

Met Lys Ile Gln Met Arg Asn Lys Lys Val Leu Ser Phe Leu Thr Leu
1               5                   10                  15

Thr Ala Ile Val Ser Gln Ala Leu Val Tyr Pro Val Tyr Ala Gln Thr
                20                  25                  30

Ser Thr Ser Asn His Ser Asn Lys Lys Glu Ile Val Asn Glu Asp
            35                  40                  45

Ile Leu Pro Asn Asn Gly Leu Met Gly Tyr Tyr Phe Ser Asp Glu His
```

-continued

```
                50                  55                  60
Phe Lys Asp Leu Lys Leu Met Ala Pro Ile Lys Asp Gly Asn Leu Lys
 65                  70                  75                  80

Phe Glu Glu Lys Lys Val Asp Lys Leu Leu Asp Lys Asp Lys Ser Asp
                 85                  90                  95

Val Lys Ser Ile Arg Trp Thr Gly Arg Ile Ile Pro Ser Lys Asp Gly
            100                 105                 110

Glu Tyr Thr Leu Ser Thr Asp Arg Asp Asp Val Leu Met Gln Val Asn
            115                 120                 125

Thr Glu Ser Thr Ile Ser Asn Thr Leu Lys Val Asn Met Lys Lys Gly
        130                 135                 140

Lys Glu Tyr Lys Val Arg Ile Glu Leu Gln Asp Lys Asn Leu Gly Ser
145                 150                 155                 160

Ile Asp Asn Leu Ser Ser Pro Asn Leu Tyr Trp Glu Leu Asp Gly Met
                165                 170                 175

Lys Lys Ile Ile Pro Glu Glu Asn Leu Phe Leu Arg Asp Tyr Ser Asn
            180                 185                 190

Ile Glu Lys Asp Asp Pro Phe Ile Pro Asn Asn Asn Phe Phe Asp Pro
        195                 200                 205

Lys Leu Met Ser Asp Trp Glu Asp Glu Asp Leu Asp Thr Asp Asn Asp
210                 215                 220

Asn Ile Pro Asp Ser Tyr Glu Arg Asn Gly Tyr Thr Ile Lys Asp Leu
225                 230                 235                 240

Ile Ala Val Lys Trp Glu Asp Ser Phe Ala Glu Gln Gly Tyr Lys Lys
                245                 250                 255

Tyr Val Ser Asn Tyr Leu Glu Ser Asn Thr Ala Gly Asp Pro Tyr Thr
            260                 265                 270

Asp Tyr Glu Lys Ala Ser Gly Ser Phe Asp Lys Ala Ile Lys Thr Glu
        275                 280                 285

Ala Arg Asp Pro Leu Val Ala Ala Tyr Pro Ile Val Gly Val Gly Met
    290                 295                 300

Glu Lys Leu Ile Ile Ser Thr Asn Glu His Ala Ser Thr Asp Gln Gly
305                 310                 315                 320

Lys Thr Val Ser Arg Ala Thr Thr Asn Ser Lys Thr Glu Ser Asn Thr
                325                 330                 335

Ala Gly Val Ser Val Asn Val Gly Tyr Gln Asn Gly Phe Thr Ala Asn
            340                 345                 350

Val Thr Thr Asn Tyr Ser His Thr Thr Asp Asn Ser Thr Ala Val Gln
        355                 360                 365

Asp Ser Asn Gly Glu Ser Trp Asn Thr Gly Leu Ser Ile Asn Lys Gly
    370                 375                 380

Glu Ser Ala Tyr Ile Asn Ala Asn Val Arg Tyr Tyr Asn Thr Gly Thr
385                 390                 395                 400

Ala Pro Met Tyr Lys Val Thr Pro Thr Thr Asn Leu Val Leu Asp Gly
                405                 410                 415

Asp Thr Leu Ser Thr Ile Lys Ala Gln Glu Asn Gln Ile Gly Asn Asn
            420                 425                 430

Leu Ser Pro Gly Asp Thr Tyr Pro Lys Lys Gly Leu Ser Pro Leu Ala
        435                 440                 445

Leu Asn Thr Met Asp Gln Phe Ser Ser Arg Leu Ile Pro Ile Asn Tyr
    450                 455                 460

Asp Gln Leu Lys Lys Leu Asp Ala Gly Lys Gln Ile Lys Leu Glu Thr
465                 470                 475                 480
```

Thr Gln Val Ser Gly Asn Phe Gly Thr Lys Asn Ser Ser Gly Gln Ile
            485                 490                 495

Val Thr Glu Gly Asn Ser Trp Ser Asp Tyr Ile Ser Gln Ile Asp Ser
        500                 505                 510

Ile Ser Ala Ser Ile Ile Leu Asp Thr Glu Asn Glu Ser Tyr Glu Arg
            515                 520                 525

Arg Val Thr Ala Lys Asn Leu Gln Asp Pro Glu Asp Lys Thr Pro Glu
    530                 535                 540

Leu Thr Ile Gly Glu Ala Ile Glu Lys Ala Phe Gly Ala Thr Lys Lys
545                 550                 555                 560

Asp Gly Leu Leu Tyr Phe Asn Asp Ile Pro Ile Asp Glu Ser Cys Val
                565                 570                 575

Glu Leu Ile Phe Asp Asp Asn Thr Ala Asn Lys Ile Lys Asp Ser Leu
                580                 585                 590

Lys Thr Leu Ser Asp Lys Lys Ile Tyr Asn Val Lys Leu Glu Arg Gly
                595                 600                 605

Met Asn Ile Leu Ile Lys Thr Pro Thr Tyr Phe Thr Asn Phe Asp Asp
    610                 615                 620

Tyr Asn Asn Tyr Pro Ser Thr Trp Ser Asn Val Asn Thr Thr Asn Gln
625                 630                 635                 640

Asp Gly Leu Gln Gly Ser Ala Asn Lys Leu Asn Gly Glu Thr Lys Ile
                645                 650                 655

Lys Ile Pro Met Ser Glu Leu Lys Pro Tyr Lys Arg Tyr Val Phe Ser
                660                 665                 670

Gly Tyr Ser Lys Asp Pro Leu Thr Ser Asn Ser Ile Ile Val Lys Ile
            675                 680                 685

Lys Ala Lys Glu Glu Lys Thr Asp Tyr Leu Val Pro Glu Gln Gly Tyr
    690                 695                 700

Thr Lys Phe Ser Tyr Glu Phe Glu Thr Thr Glu Lys Asp Ser Ser Asn
705                 710                 715                 720

Ile Glu Ile Thr Leu Ile Gly Ser Gly Thr Thr Tyr Leu Asp Asn Leu
                725                 730                 735

Ser Ile Thr Glu Leu Asn Ser Thr Pro Glu Ile Leu Asp Glu Pro Glu
                740                 745                 750

Val Lys Ile Pro Thr Asp Gln Glu Ile Met Asp Ala His Lys Ile Tyr
                755                 760                 765

Phe Ala Asp Leu Asn Phe Asn Pro Ser Thr Gly Asn Thr Tyr Ile Asn
    770                 775                 780

Gly Met Tyr Phe Ala Pro Thr Gln Thr Asn Lys Glu Ala Leu Asp Tyr
785                 790                 795                 800

Ile Gln Lys Tyr Arg Val Glu Ala Thr Leu Gln Tyr Ser Gly Phe Lys
                805                 810                 815

Asp Ile Gly Thr Lys Asp Lys Glu Met Arg Asn Tyr Leu Gly Asp Pro
            820                 825                 830

Asn Gln Pro Lys Thr Asn Tyr Val Asn Leu Arg Ser Tyr Phe Thr Gly
    835                 840                 845

Gly Glu Asn Ile Met Thr Tyr Lys Lys Leu Arg Ile Tyr Ala Ile Thr
850                 855                 860

Pro Asp Asp Arg Glu Leu Leu Val Leu Ser Val Asp
865                 870                 875

<210> SEQ ID NO 7
<211> LENGTH: 224

```
<212> TYPE: PRT
<213> ORGANISM: Homo sapiens

<400> SEQUENCE: 7

Ile Val Gly Gly Tyr Asn Cys Glu Glu Asn Ser Val Pro Tyr Gln Val
1               5                   10                  15

Ser Leu Asn Ser Gly Tyr His Phe Cys Gly Gly Ser Leu Ile Asn Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Gln Tyr Asp Arg Lys Thr
65                  70                  75                  80

Leu Asn Asn Asp Ile Met Leu Ile Lys Leu Ser Ser Arg Ala Val Ile
                85                  90                  95

Asn Ala Arg Val Ser Thr Ile Ser Leu Pro Thr Ala Pro Pro Ala Thr
            100                 105                 110

Gly Thr Lys Cys Leu Ile Ser Gly Trp Gly Asn Thr Ala Ser Ser Gly
        115                 120                 125

Ala Asp Tyr Pro Asp Glu Leu Gln Cys Leu Asp Ala Pro Val Leu Ser
    130                 135                 140

Gln Ala Lys Cys Glu Ala Ser Tyr Pro Gly Lys Ile Thr Ser Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Val Val Ser
            180                 185                 190

Trp Gly Asp Gly Cys Ala Gln Lys Asn Lys Pro Gly Val Tyr Thr Lys
        195                 200                 205

Val Tyr Asn Tyr Val Lys Trp Ile Lys Asn Thr Ile Ala Ala Asn Ser
    210                 215                 220

<210> SEQ ID NO 8
<211> LENGTH: 224
<212> TYPE: PRT
<213> ORGANISM: Homo sapiens

<400> SEQUENCE: 8

Ile Val Gly Gly Tyr Ile Cys Glu Glu Asn Ser Val Pro Tyr Gln Val
1               5                   10                  15

Ser Leu Asn Ser Gly Tyr His Phe Cys Gly Gly Ser Leu Ile Ser Glu
            20                  25                  30

Gln Trp Val Val Ser Ala Gly His Cys Tyr Lys Ser Arg Ile Gln Val
        35                  40                  45

Arg Leu Gly Glu His Asn Ile Glu Val Leu Glu Gly Asn Glu Gln Phe
    50                  55                  60

Ile Asn Ala Ala Lys Ile Ile Arg His Pro Lys Tyr Asn Ser Arg Thr
65                  70                  75                  80

Leu Asp Asn Asp Ile Leu Leu Ile Lys Leu Ser Ser Pro Ala Val Ile
                85                  90                  95

Asn Ser Arg Val Ser Ala Ile Ser Leu Pro Thr Ala Pro Pro Ala Ala
            100                 105                 110

Gly Thr Glu Ser Leu Ile Ser Gly Trp Gly Asn Thr Leu Ser Ser Gly
        115                 120                 125
```

```
Ala Asp Tyr Pro Asp Glu Leu Gln Cys Leu Asp Ala Pro Val Leu Ser
            130                 135                 140

Gln Ala Glu Cys Glu Ala Ser Tyr Pro Gly Lys Ile Thr Asn Asn Met
145                 150                 155                 160

Phe Cys Val Gly Phe Leu Glu Gly Gly Lys Asp Ser Cys Gln Gly Asp
                165                 170                 175

Ser Gly Gly Pro Val Val Ser Asn Gly Glu Leu Gln Gly Ile Val Ser
                180                 185                 190

Trp Gly Tyr Gly Cys Ala Gln Lys Asn Arg Pro Gly Val Tyr Thr Lys
                195                 200                 205

Val Tyr Asn Tyr Val Asp Trp Ile Lys Asp Thr Ile Ala Ala Asn Ser
            210                 215                 220

<210> SEQ ID NO 9
<211> LENGTH: 246
<212> TYPE: PRT
<213> ORGANISM: Homo sapiens

<400> SEQUENCE: 9

Gly Cys Gly Val Pro Ala Ile His Pro Val Leu Ser Gly Leu Ser Arg
1               5                   10                  15

Ile Val Asn Gly Glu Asp Ala Val Pro Gly Ser Trp Pro Trp Gln Val
            20                  25                  30

Ser Leu Gln Asp Lys Thr Gly Phe His Phe Cys Gly Gly Ser Leu Ile
        35                  40                  45

Ser Glu Asp Trp Val Val Thr Ala Ala His Cys Gly Val Arg Thr Ser
50                  55                  60

Asp Val Val Ala Gly Glu Phe Asp Gln Gly Ser Asp Glu Glu Asn
65                  70                  75              80

Ile Gln Val Leu Lys Ile Ala Lys Val Phe Lys Asn Pro Lys Phe Ser
                85                  90                  95

Ile Leu Thr Val Asn Asn Asp Ile Thr Leu Leu Lys Leu Ala Thr Pro
            100                 105                 110

Ala Arg Phe Ser Gln Thr Val Ser Ala Val Cys Leu Pro Ser Ala Asp
        115                 120                 125

Asp Asp Phe Pro Ala Gly Thr Leu Cys Ala Thr Thr Gly Trp Gly Lys
130                 135                 140

Thr Lys Tyr Asn Ala Asn Lys Thr Pro Asp Lys Leu Gln Gln Ala Ala
145                 150                 155                 160

Leu Pro Leu Leu Ser Asn Ala Glu Cys Lys Lys Ser Trp Gly Arg Arg
                165                 170                 175

Ile Thr Asp Val Met Ile Cys Ala Gly Ala Ser Gly Val Ser Ser Cys
            180                 185                 190

Met Gly Asp Ser Gly Gly Pro Leu Val Cys Gln Lys Asp Gly Ala Trp
        195                 200                 205

Thr Leu Val Gly Ile Val Ser Trp Gly Ser Asp Thr Cys Ser Thr Ser
210                 215                 220

Ser Pro Gly Val Tyr Ala Arg Val Thr Lys Leu Ile Pro Trp Val Gln
225                 230                 235                 240

Lys Ile Leu Ala Ala Asn
            245
```

THERAPIES FOR PREVENTING OR SUPPRESSING *CLOSTRIDIUM DIFFICILE* INFECTION

SEQUENCE LISTING INCORPORATION BY REFERENCE

A sequence listing in an ASCII text file, having the name "MSQ07-024-CIP-US_Sequence_Listing_FOR_NMR.txt", created on 6 Dec. 2010, and having a size of 104 kb, is hereby incorporated by reference in its entirety.

The present invention relates to therapeutics and corresponding therapies for the treatment or suppression of *Clostridium difficile* infection (CDI).

*Clostridium difficile* infection (CDI) is now a major problem in hospitals worldwide. The bacterium causes nosocomial, antibiotic-associated disease which manifests itself in several forms ranging from mild self-limiting diarrhoea to potentially life-threatening, severe colitis. Elderly patients are most at risk from these potentially life-threatening diseases and incidents of CDI have increased dramatically over the last 10 years. In 2007 in the UK there were over 50,000 cases of CDI with over 8,000 associated deaths. CDI costs the NHS>£500M per annum.

The various strains of *C. difficile* may be classified by a number of methods. One of the most commonly used is polymerase chain reaction (PCR) ribotyping in which PCR is used to amplify the 16S-23S rRNA gene intergenic spacer region of *C. difficile*. Reaction products from this provide characteristic band patterns identifying the bacterial ribotype of isolates. Toxinotyping is another typing method in which the restriction patterns derived from DNA coding for the *C. difficile* toxins are used to identify strain toxinotype. The differences in restriction patterns observed between toxin genes of different strains are also indicative of sequence variation within the *C. difficile* toxin family. Toxin B shows sequence variation in some regions. For example, there's an approximate 13% sequence difference with the C-terminal 60 kDa region of toxinotype 0 Toxin B compared to the same region in toxinotype III.

Strains of *C. difficile* produce a variety of virulence factors, notable among which are several protein toxins: Toxin A, Toxin B and, in some strains, a binary toxin which is similar to *Clostridium perfringens* iota toxin. Toxin A is a large protein cytotoxin/enterotoxin which plays a role in the pathology of infection and may influence the gut colonisation process. Outbreaks of CDI have been reported with Toxin A-negative/Toxin B-positive strains, which indicates that Toxin B is also capable of playing a key role in the disease pathology. Both Toxins A and B exert their mechanisms of action via multi-step mechanisms, which include binding to receptors on the cell surface, internalisation followed by translocation and release of the effector domain into the cell cytosol and finally intracellular action. For both Toxins A and B this involves the inactivation of small GTPases of the Rho family. For this inactivation, each toxin catalyses the transfer of a glucose moiety (from UDP-glucose) on to an amino residue of the Rho protein. Both Toxins A and B also contain a second enzyme activity in the form of a cysteine protease which appears to play a role in the release of the effector domain into the cytosol after translocation. The *C. difficile* binary toxin modifies cell actin by a mechanism which involves the transfer of an ADP-ribose moiety from NAD onto its target protein.

Treatment of *C. difficile* infection currently relies on antibiotics of which metronidazole and vancomycin constitute those of choice. However, these antibiotics are not effective in all cases and 20-30% of patients suffer relapse of the disease. Of major concern is the appearance in the UK of more virulent strains which were first identified in Canada in 2002. These strains, which include those belonging to PCR ribotype 027, toxinotype III, cause CDI with a directly attributable mortality more than 3-fold that observed previously.

New therapeutics are therefore required especially urgently since the efficacy of current antibiotics appears to be decreasing.

Accordingly, there is a need in the art for new therapies/therapeutics capable of specifically addressing *C. difficile* infection (CDI). This need is addressed by the present invention, which solves one or more of the above-mentioned problems.

In more detail, a first aspect of the present invention provides ovine antibodies, for oral use in the prevention or treatment of CDI. Said oral therapy provides a simple treatment/prevention/suppression of CDI with unexpected efficacy and/or with reduced side-effects. In another aspect, the invention provides an antibody composition comprising the ovine antibodies, in a form suitable for oral use in the prevention or treatment of CDI. In one embodiment, the ovine antibodies are polyclonal antibodies.

In use, the antibodies of the invention bind to a *C. difficile* toxin or a fragment thereof, preferably neutralising the biological activity of the toxin or fragment thereof. Accordingly, the antibodies of the present invention are capable of preventing or treating CDI, and/or preferably also preventing a relapse in a patient.

The antibody therapy of the present invention provides a distinct advantage over other therapies in that it is able to inhibit the biological action of one or more of the toxins of *C. difficile*, whilst having a minimal or low immunogenic effect on a patient. Moreover, the antibodies of the present invention can be produced with very high toxin-neutralising titres. Thus, the ovine antibodies can be readily obtained and can protect the patient against the pathological effects produced by *C. difficile* with minimal or no side-effects. The antibodies of the present invention may also be used prophylactically to prevent the onset of CDI.

The principal targets of the present invention are *C. difficile* toxins or fragments thereof. Suitable *C. difficile* toxins, to which the antibodies of the invention may bind to and/or neutralise, include any *C. difficile* toxins that cause or are associated with CDI or a symptom thereof. In a further embodiment, the antibodies of the invention bind to and/or neutralise one or more type of *C. difficile* toxin selected from the following: *C. difficile* Toxin A or a fragment thereof, *C. difficile* Toxin B or a fragment thereof, and *C. difficile* Binary Toxin or a fragment thereof.

Thus, in one embodiment, the antibody composition of the present invention comprises ovine antibodies that bind to and/or neutralise *C. difficile* Toxin A (or a fragment thereof). In another embodiment, the antibody composition of the present invention comprises ovine antibodies that bind to and/or neutralise *C. difficile* Toxin B (or a fragment thereof). In yet another embodiment, the antibody composition of the present invention comprises ovine antibodies that bind to and/or neutralise *C. difficile* Binary Toxin (or a fragment thereof).

In another embodiment, the antibody composition of the present invention comprises ovine antibodies that bind to and/or neutralise *C. difficile* Toxin A (or a fragment thereof) and to *C. difficile* Toxin B (or a fragment thereof). In another embodiment, the antibody composition of the present invention comprises ovine antibodies that bind to and/or neutralise *C. difficile* Toxin A (or a fragment thereof) and to *C. difficile*

Binary Toxin (or a fragment thereof). In yet another embodiment, the antibody composition of the present invention comprises ovine antibodies that bind to and/or neutralise *C. difficile* Toxin B (or a fragment thereof) and to *C. difficile* Binary Toxin (or a fragment thereof).

The antibody composition of the present invention may also comprise ovine antibodies that bind to and/or neutralise *C. difficile* Toxin A (or a fragment thereof), to *C. difficile* Toxin B (or a fragment thereof) and to *C. difficile* Binary Toxin (or a fragment thereof).

The antibodies of the present invention interact with specific epitopes of the toxin. For example, an antibody can bind an epitope in the N-terminal domain (e.g. between amino acids 1-957) or the mid-region domains (e.g. between amino acids 958-1831) or the C-terminal repeat domains (e.g. between amino acids 1832-2710) of *C. difficile* Toxin A. For example, the antibody may bind to an epitope within amino acids 1832-2710 of *C. difficile* Toxin A. Similarly an antibody can bind an epitope in the N-terminal domain (e.g. between amino acids 1-955) or the mid-region domains (e.g. between amino acids 956-1831) or the C-terminal repeat domains (e.g. between amino acids 1832-2366) of Toxin B. For example, an antibody may bind to an epitope within amino acids 1832-2366 of Toxin B. In the case of the binary toxin antibodies may bind to the catalytic domain (Fragment A) or the receptor binding domain, which resides in the C-terminal portion of Fragment B (approx residues 400-870); and/or to the N-terminal half of Fragment B (approx residues 1-400), which is involved in the binding and translocation of Fragment A into the cell.

In one embodiment, the *C. difficile* toxin is selected from one of toxinotypes 0 to XV. Preferred toxinotypes (plus example Ribotypes and Strains) are listed in the Table immediately below. The listed toxinotypes are purely illustrative and are not intended to be limiting to the present invention.

| Toxinotype | Example Ribotypes | Example Strains | Reference |
|---|---|---|---|
| 0 | 001, 106 | VPI10463 | Rupnik et al. (1998) |
| I | 003, 012, 102 | EX623 | J. Clinical |
| II | 103 | AC008 | Microbiol. 36: |
| III | 027, 034, 075, 080 | R20291, QCD-32g58 | 2240-2247 |
| IV | 023, 034, 075, 080 | 55767 | |
| V | 066, 078 | SE881 | |
| VI | 045, 063, 066 | 51377 | |
| VII | 063 | 57267 | |
| VIII | 017, 047 | 1470 | |
| IX | 019 | 51680 | |
| X | 036 | 8864 | |
| XI | 033 | IS58, R11402 | Rupnik et al. (2001) |
| XII | 056 | IS25 | Microbiology |
| XIII | 070 | R9367 | 147: 439-447 |
| XIV | 111 | R10870 | |
| XV | 122 | R9385 | |

Different antibodies of the present invention may bind to and/or neutralise a *C. difficile* toxin from the same or from different strains of *C. difficile*. For example, the antibodies may bind to and/or neutralise one or more of the following: *C. difficile* Toxin A—Toxinotype 0; *C. difficile* Toxin B—Toxinotype 0; *C. difficile* Toxin A—Toxinotype III; *C. difficile* Toxin B—Toxinotype III; *C. difficile* Toxin A—Toxinotype V; and/or *C. difficile* Toxin B—Toxinotype V. Preferably, a mixture of antibodies is employed, which bind to and/or neutralise Toxins A and B from all or most of these Toxinotypes. An antibody of the present invention may bind to an epitope in the N-terminal domain, the mid-region domain, and/or the C-terminal repeat domain of said strains of *C. difficile* Toxin A and/or *C. difficile* Toxin B and/or *C. difficile* Binary Toxin.

In certain embodiments, the antibodies of the present invention may bind to and/or neutralise at least one *C. difficile* toxin comprising an amino acid sequence at least 80%, 85%, 90%, 95%, 98%, 99%, or more identical to SEQ ID NOs: 1-6, or a fragment thereof.

The invention also embraces a corresponding method for prevention or treatment of CDI, said method comprising oral administration of the antibody composition of the present invention to a patient. The patient can be infected with *C. difficile*, or have a symptom of *C. difficile* (e.g. mild self-limiting diarrhoea, abdomenal pain, fever and loss of appetite to life-threatening conditions such as pseudomembranous colitis and cytotoxic megacolon) or have a predisposition towards *C. difficile* infection (e.g. undergoing treatment with antibiotics, having experienced *C. difficile* and at risk of relapse, or exposed to a second individual who has shown the clinical symptoms associated with *C. difficile* infection). The present invention thereby provides an effective means for preventing, suppressing or treating CDI (or a symptom thereof).

In one embodiment, said method of treating CDI comprises oral administration of the antibody composition of the present invention to a patient infected with *C. difficile*, or suffering from the symptoms of CDI. This can be accomplished using a therapeutically effective amount of the antibodies. Such administration may be effected by repeated administrations of antibody compositions of the present invention, for a prolonged period of time. The antibody components of said compositions may be the same or different (in terms of their toxinotype specificity and/or targeted binding region or epitope on a *C. difficile* Toxin), and administration can be concurrent or sequential, and can be effected in any order.

In another embodiment, said method of preventing CDI comprises oral administration of the antibody composition of the present invention to a patient to provide passive immunity against CDI. This can be accomplished using a prophylactically effective amount of the antibodies prior to the onset or in the very early stages of CDI. Such administration may be effected by repeated administrations of antibody compositions of the present invention, for a prolonged period of time. The antibody components of said compositions may be the same or different (in terms of their toxinotype specificity and/or targeted binding region or epitope on a *C. difficile* Toxin), and administration can be concurrent or sequential, and can be effected in any order.

In another embodiment, said method of treating CDI comprises administering antibody systemically (eg. once or twice per day, or once or twice or 3- or 4-times per every 3-4 days; for a short period of typically 1-2 weeks) followed by a more prolonged period of oral administration (eg. once or twice or 3- or 4- or 5- or 6-times per day, or once or twice or 3- or 4- or 5- or 6-times per every 3-4 days, or once or twice or 3- or 4- or 5- or 6-times per week) of antibody. In this embodiment, the systemically administered antibody is provided as a formulation suitable for that route and the orally administered antibody is provided in the form of a composition of the present invention. Such administration may be effected by giving one or more administrations of antibody via the systemic route followed by repeated oral administrations of antibody compositions of the present invention, for a more prolonged period of time. The antibody components of said compositions may be the same or different (in terms of their toxinotype specificity and/or targeted binding region or epitope on a *C. difficile* Toxin).

In another embodiment, the above oral administration may be performed prior to or simultaneously with a corresponding systemic administration of said antibodies. Naturally, when administered systemically, the antibodies are formulated accordingly (eg. such formulations are typically provided as isotoxic aqueous formulations and do not require means for protection against stomach acid or stomach enzymes such as trypsin and/or chymotrypsin).

In one embodiment, the subject to be treated or protected is a subject in one or more or the following category: hospitalised; over 65 or 70 years' old; receiving broad-range spectrum antibiotics; having previous CDI history/infection; having close proximity to symptomatic CDI patients; having mild-to-moderate disease severity; presenting as asymptomatic but considered at high risk of relapse (eg. because of one or more relapse episodes); having close proximity to CDI outbreak areas or patients.

Antibody Preparation

The ovine antibodies are antibodies which have been raised in a sheep. Thus, the present invention includes a method of producing ovine antibodies for use in the antibody composition of the invention, said method generally involving (i) administering an immunogen comprising a *C. difficile* toxin or a fragment thereof to a sheep, (ii) allowing sufficient time for the generation of antibodies in the sheep, and (iii) obtaining the antibodies from the sheep. As used herein, sheep comprise any species that fall within the *Ovis* genus (e.g. *Ovis ammon, Ovis orientalis aries, Ovis orientalis orientalis, Ovis orientalis vignei, Ovis Canadensis, Ovis dalli, Ovis nivicola*).

The present invention also includes a method of producing ovine antibodies for use in the oral antibody composition of the invention, wherein the ovine antibodies are elicited by a sheep in response to an immunogen comprising a *C. difficile* toxin or a fragment thereof (preferably a fragment that possesses antigenic cross-reactivity with the full-length natural Toxin and/or retains the toxin or toxin-like activity of the full-length natural Toxin).

The antibody may be obtained from the sheep serum. Thus, the procedures generate sheep antisera containing antibodies capable of binding and neutralising *C. difficile* toxins. In a further embodiment, the antibodies are isolated and/or purified. Thus, another aspect of the present invention involves purifying the antibodies from sheep antiserum.

In one embodiment, the immunogen used to generate the antibodies of the present invention is a *C. difficile* toxin or a fragment thereof, which has optionally been purified. Suitable *C. difficile* toxins include any *C. difficile* toxins that cause or are associated with CDI or a symptom thereof. In a further embodiment, the toxin is selected from at least one of the following toxins: *C. difficile* Toxin A or a fragment thereof, *C. difficile* Toxin B or a fragment thereof and *C. difficile* Binary Toxin or a fragment thereof. The *C. difficile* toxin may also be a toxin selected from one of the toxinotypes 0 to XV as defined hereinbefore.

Production of a purified *C. difficile* toxin is exemplified in the Examples. In certain embodiments, the immunogen is a *C. difficile* toxin variant. In another embodiment the immunogen comprises an amino acid sequence at least 80%, 85%, 90%, 95%, 98%, 99%, or more identical to SEQ ID NOs: 1-6, or a fragment thereof.

The immunogen used to generate the antibodies of the present invention may also be partially or completely inactivated, i.e. have reduced toxicity. Examples of modification include: chemical treatment (e.g. treatment with UDP-dialdehyde, formaldehyde, glutaraldehyde, peroxide, or oxygen) and recombinant methods (e.g. deletions or mutations in the toxin). For example, the immunogen may be a *C. difficile* toxoid or a fragment thereof derived from the native toxin by treatment with formaldehyde. Alternatively, a recombinant toxoid may be generated by selectively inactivating the active site motif by site-directed mutagenesis. An example of site directed mutagenesis to reduce or ablate the toxin effects of Toxins A and B is modification of the DXD motif in the N-terminal domain of the toxin. The aspartates and/or other residues may be mutated to e.g. alanine in order to reduce the biological activity of either Toxin A and B. For example, for Toxin A one of more of the following amino acids may be mutated: Asp 269, Asp285, Asp 287, Asn383, Trp519, Tyr283, Arg272. For Toxin B one of more of the following amino acids may be mutated: Asp270, Asp286, Asp 288, Asn384, Trp520, Tyr284, Arg273.

Antigens may be formulated with an adjuvant. Suitable adjuvants may include alum (aluminium phosphate or aluminium hydroxide), which is used widely in humans, and other adjuvants such as saponin and its purified component Quil A, Freund's complete and incomplete adjuvant, RIBBI adjuvant, and other adjuvants used in research and veterinary applications.

The *C. difficile* toxins or toxoids may be used as immunogens separately or in combination, either concurrently or sequentially, in order to produce antibodies specific for individual *C. difficile* toxins or combinations. For example, two or more toxins or toxoids may be mixed together and used as a single immunogen. Alternatively a *C. difficile* toxin (e.g. *C. difficile* Toxin A) may be used separately as a first immunogen on a first sheep, and another *C. difficile* toxin (e.g. *C. difficile* Toxin B) may be used separately on a second sheep. The antibodies produced by separate immunisation may be combined to yield an antibody composition directed against *C. difficile* toxins.

Where the oral delivery aspect of the present invention includes a separate or additional therapeutic component (eg. a non-oral therapy/therapeutic), the latter is formulated by conventional means—examples of non-oral therapies include administration of an antibody or antibodies of the present invention via any non-oral route, including subcutaneous, intramuscular, intraperitoneal, and intravenous.

The method comprises all modes of immunisation (ie. to generate the antibodies of the invention), including subcutaneous, intramuscular, intraperitoneal, and intravenous. The invention also contemplates a wide variety of immunisation schedules. In one embodiment, a sheep or goat is administered toxin(s) on day zero and subsequently receives toxin(s) at intervals thereafter. It will be appreciated that the interval range and dosage range required depends on the precise nature of the immunogen, the route of administration, the nature of the formulation, and the judgement of the attending person. Variations in these dosage levels can be adjusted using standard empirical routines for optimisation. Similarly, it is not intended that the present invention be limited to any particular schedule for collecting antibody. The preferred collection time is someday after day 56. Levels of the specific antibody, i.e. that which binds to the immunogen, should represent at least 3 g per liter of serum.

The antibodies of the invention may be modified as necessary after collection, so that, in certain instances, they are less immunogenic in the patient to whom they are administered. For example, if the patient is a human, the antibodies may be despeciated by methods well known in the art. One example as to how an antibody can be made less immunogenic is to prepare the F(ab)$_2$ fragment. The antibodies of the invention may be used to produce such antibody fragments for which various techniques have been developed. For example, the fragments may be derived by proteolytic digestion of intact antibodies. Other techniques for their production will be apparent to the skilled practitioner.

Antibody Formulation and Delivery

In use, the present invention employs a pharmaceutical composition, comprising the antibody composition of the present invention in a form suitable for oral administration. The purified intact antibodies, or their fragments, are formulated for such delivery. For example, antibody, or its fragment, at a concentration between 5-50 or 15-50 or 25-50 g/liter may be formulated in buffer. Examples of suitable buffer components include physiological salts such as sodium citrate and/or citric acid. Preferred buffers contain 100-200 or 125-175 or approximately 150 (eg. 153) mM physiological salts such as sodium chloride.

Antibody compositions of the invention are formulated for oral delivery. A key problem with oral delivery is ensuring that sufficient antibody reaches the colon where it is required. In this regard, factors that may inhibit optimal amounts of antibody reaching the gut include the proteolytic enzymes present in the digestive secretions, which degrade the antibody molecule and also in some instances the effect of CDI itself which can cause paralytic ileus and other complications that prevent movement of fluids down the alimentary canal. Thus, in a preferred embodiment of the present invention, the antibody composition is formulated by incorporation of means for countering/reducing the undesirable effects of the alimentary enzymes (eg. stomach enzymes) and environment (eg. stomach acid). There now follows a non-limiting description of a variety of embodiments of said means. Each of said embodiments may be employed alone or in combination with each other. Additional means known to a skilled person are included within the context of the present invention, and may also be employed alone or in combination with any of the following embodiments.

The oral antibody formulations/compositions of the present invention may include one or more inhibitor of trypsin (e.g. an inhibitor of trypsin-1 and/or trypsin-2) and/or chymotrypsin (e.g. an inhibitor of chymotrypsin B). In one embodiment, said inhibitor is a macromolecular inhibitor (eg. a macromolecular inhibitor having a molecular weight of at least 5 kDa), such as a polypeptide-based inhibitor. By way of example, said inhibitor(s) may contain a polypeptide loop, which when cleaved by either trypsin or chymotrypsin causes the inhibitor to bind very strongly to the protease thus inhibiting the further action of trypsin and/or chymotrypsin. One preferred inhibitor in this regard may be provided, for convenience, in the form of egg white (albumin). Alternatively (or in addition), the active component thereof (e.g. ovomucoid and ovostatin/ovomacroglobulin) may be employed. Another example is soybean trypsin inhibitor.

In one embodiment, an inhibitor cocktail may be provided, for convenience, in the form of colostrum (e.g. bovine). Alternatively (or in addition), the active component(s) thereof may be employed. Colostrum is readily combinable with ovine antibodies to provide a suitable formulation of oral administration.

In one embodiment, the trypsin inhibitor is a small protein (eg. Mw 5-25 kDa) that is naturally synthesized in the exocrine pancreas which prevents conversion of trypsinogen to trypsin, so protecting itself against trypsin digestion. Pancreatic trypsin inhibitor competitively binds to the active site of trypsin and inactivates it at a very low concentration. Examples of trypsin inhibitors suitable for use in the present invention include both naturally produced and recombinantly produced molecules, such as:

| Source | Mw | Additional information |
|---|---|---|
| Lima beans | 8-10 kDa | There are six different lima bean inhibitors. |
| Bovine pancreas | 6.5 kDa | Kunitz inhibitor is the best known pancreatic inhibitor. Chymotrypsin is also inhibited by this chemical, but less tightly. When extracted from lung tissue, this is known as aprotinin. |
| Ovomucoid | ca. 27 kDa | Ovomucoids are glycoprotein protease inhibitors found in raw avian egg white. |
| Ovostatin | ca. 175 kDa | Ovostatins (ovomacroglobulins) are protease inhibitors found in raw avian egg white. |
| Soybeans | 20.7-22.3 kDa | Soybeans contain several trypsin inhibitors. All also bind to and inactivate chymotrypsin. |

Natural pancreatic trypsin inhibitors are produced by the acinar cells and provide security against accidental trypsinogen activation and consequential unbridled proteolysis. By way of example, the intracellular basic trypsin inhibitor (BPTI) was first crystallized by Kunitz and Northrop in 1936. Basic pancreatic trypsin inhibitor (BPTI) forms a very stable 1:1 complex with bovine trypsin between pH 3 and 10, and also human trypsins. Chymotrypsin is also inhibited by BPTI. Soybean trypsin inhibitor (SBTI) first crystallized by Kunitz (1945) is one of several trypsin inhibitors found in soybeans. The best known preparation is that of Kunitz (Mw 21,500±800; isoelectric point: 4.5). The Kunitz soybean inhibitor consists of a single polypeptide chain crosslinked by two disulfide bridges, and inhibits trypsin mole-for-mole and to a lesser extent chymotrypsin. Ovomucoids (Mw 28,500±3, 500) are the glycoprotein protease-inhibitors of avian egg white, and act upon bovine trypsin and chymotrypsin. Lima bean trypsin inhibitor (LBI) acts upon both trypsin and chymotrypsin by forming equimolar complexes. The trypsin susceptible binding site is a lys-ser peptide bond, whereas the site of chymotrypsin action is a leu-ser bond (Krahn and Stevens 1970). Lima bean trypsin inhibitors (Mw 8,000-10,000) may be chromatographically separated into as many as six variants. All have similar but not identical amino acid composition, contain six or seven disulfide bonds and lack methionine and tryptophan.

By way of further example, Bowman Birk protease inhibitors are a group of chymotrypsin and trypsin inhibitors produced by Soybeans and a range of leguminous plants. They are small disulphide rich proteins of 7-10 kda which are non-toxic to humans and well tolerated. Chymotrypsin peptide inhibitors which are extremely stable to extremes of pH occur in turtle egg whites. These small peptide inhibitors (approx 13 kDa) form stable complexes with chymotrypsin (Guha et al (1984) J. Bioscience 6: 155-163).

In one embodiment, the trypsin and/or chymotrypsin inhibitor(s) component may be an antibody (including a fragment thereof) that binds to (eg. specifically binds to) and inactivates the enzymatic activity of trypsin and/or chymotrypsin. Such antibody-based inhibitors may be used as an alternative or in addition to the above non-antibody-based inhibitors. Thus, an inhibitor combination of an antibody-based inhibitor and a non-antibody inhibitor may be employed. By way of example, a non-antibody inhibitor (eg. ovomucoid) may be used in combination with an antibody inhibitor where the antibody inhibits chymotrypsin (and/or trypsin). Similarly, a non-antibody chymotrypsin inhibitor may be used in combination with an antibody inhibitor where the antibody inhibits trypsin (and/or chymotrypsin). Such antibodies may be prepared routinely (eg. see Example 10).

The above-described trypsin and/or chymotrypsin inhibitor(s) may be orally administered prior to, simultaneously with, or subsequent to the antibody component. In one embodiment, the inhibitor(s) are administered prior to or simultaneously with the antibody component.

In one embodiment, the oral antibody formulations of the present invention may include an antacid component. In use, said antacid component helps protect the antibody component from the highly acid gastric environment that exists within a patient.

An antacid is any substance, generally a base or basic salt, which counteracts stomach acidity. In other words, antacids are stomach acid neutralizers that raise the stomach pH, ideally above pH 4.0, for a limited time period Antacids perform a neutralization reaction, i.e. they buffer gastric acid, raising the pH to reduce acidity in the stomach.

Examples of suitable antacids for use in the present invention include: aluminium hydroxide (eg. Amphojel, Alterna-GEL); magnesium hydroxide (e.g. Phillips' Milk of Magnesia); aluminum hydroxide with magnesium hydroxide (e.g. Maalox, Mylanta, Diovol); Aluminum carbonate gel (eg. Basaljel); calcium carbonate (eg. Alcalak, TUMS, Quick-Eze, Rennie, Titralac, Rolaids); sodium bicarbonate (eg. bicarbonate of soda, Alka-Seltzer); magnesium carbonate; magnesium trisilicate; hydrotalcite (eg. $Mg_6Al_2(CO_3)(OH)_{16}$. $4(H_2O)$; Talcid); bismuth subsalicylate (e.g. Pepto-Bismol); alginates (e.g. sodium alginate, alginic acid); magaldrate with simethicone (eg. Pepsil); any of the above in combination with simethicone for example Asilone, which has three active ingredients, aluminium hydroxide and magnesium oxide neutralise the acid removing the cause of the pain, and dimethicone.

In addition (or alternatively) to the above-described formulation components, the composition may include a physical and/or chemical means for protecting the antibody from the acidic environment of the stomach so that an active antibody is ultimately delivered to the intestine site of action (eg. the colon).

By way of example, the antibodies may be encapsulated (eg. pellets, granular matrices, beads, microspheres, nanoparticles, or liposomes) and/or may be chemically protected (eg. by PEGylation).

Conventional encapsulation techniques suitable for use in the present invention include:

| Technique employed | Polymer(s) used |
| --- | --- |
| pH dependent | Eudragit L100 and S100 |
| | Eudragit L100 and S100 |
| | Eudragit L100 and S100 |
| | Eudragit S, Eudragit FS, Eudragit P4135 F |
| | Eudragit L 30 D-55 and Eudragit FS 30 D |
| Time dependent | Hydroxy propyl methyl cellulose |
| | Hydroxyethyl cellulose, ethyl cellulose, microcrystalline cellulose |
| | Lactose/behinic acid |
| | Hydroxy propyl methyl cellulose |
| | Hydroxy propyl methyl cellulose acetate succinate |
| Bacteria dependent/ Polysaccharide based | Chitosan |
| | Pectin |
| | Guar gum |
| | Chondroitin sulphate |
| | Amylose |
| | Alginates |

The pH in the terminal ileum and colon (except ascending colon) is higher than in any other region of the GI tract. Thus a dosage form that disintegrates preferentially at high pH levels is optimal for site-specific delivery into this region. One of the simplest approaches for designing a pH-dependent multiparticulate colon-specific delivery system is enteric coated granules. Enteric coating has traditionally been used to prevent drug release in the upper GI tract. Enteric coating polymers may be used as both binders and as coating materials for granules. The incorporation of citric acid into the coating and/or the tablet matrix helps to retard in vitro release and in vivo absorption because of the prolongation in disintegration time of the core system due to the presence of the acid. Most commonly used pH-dependent coating polymers for peroral delivery are methacrylic acid copolymers, Eudragit L100 and Eudragit S100, which dissolve at pH 6.0 and 7.0 respectively. The combination of these two polymers in various ratios makes it possible to manipulate drug release within 6.0-7.0 pH range. Capsules comprising these polymers may be further coated with solutions of polymethacrylates.

Similarly, excipients such as aqueous hydroxypropyl methyl cellulose acetate succinate as a coating material and citric acid as a pH regulating agent may be added. Glyceryl palmitostearate may be used as a retardant material to formulate controlled release matrices.

Coating formulations (e.g. Eudragit S100) may be further covered with a layer of chitosan HCl. Upon hydration, the capsule shell dissolves and the chitosan layer forms a gel (internal pH of 4.5), which generates an acidic environment around the Eudragit film so that it does not dissolve in the ascending colon. In the ascending colon, the chitosan HCl gel is degraded by the colonic micro flora, thereby exposing the Eudragit film to the colonic environment. But since the ascending colon is weakly acidic with a pH is less than 7.0, the film coat still remains intact. However, on arrival in the descending colon where pH is greater than 7, the Eudragit film coat dissolves and the drug is released in a controlled fashion from the matrices. Multi-layer coats may be employed based on, for example, an inner coat (a combination of Eudragit RL/RS), and an outer coat (Eudragit FS 30D). Eudragit FS 30D is an-ionic co-polymer of methyl acrylate, methyl methacrylate and methacrylic acid and is pH sensitive and dissolves at pH above 6.5.

Microbially-controlled delivery systems may also be employed, which rely on the unique enzymatic ability of the colonic micro flora. Delivery systems of this type enable a more specific targeting, independent of pH variations along the GI tract. Many natural polysaccharides such as chondroitin sulphate, pectin, dextran, guar gum etc. may be employed. Multiparticulate systems comprising hydrogel beads (chitosan and tripolyphosphate (TPP)) are one option—TPP acts as a counter ion to positively charged chitosan to form gel beads. The beads are loaded with bovine serum albumin (BSA), a protein that is liable to degradation in the upper parts of GI tract, and the cross-linking of chitosan with TPP results in reduced solubility of chitosan, thereby resulting in lesser protein (antibody) release during upper GI transit. Amylose is a particularly good film-forming polymer (via gelation), and may also be mixed with Eudragit RS/RL 30D aqueous dispersions. Similarly, amidated low methoxy pectin which forms rigid gels with divalent cations (eg. calcium or zinc) may be employed to produce calcium pectinate gel beads for colonic delivery. Pectin may be combined with calcium salts—calcium pectinate (the insoluble salt of pectin) is not degraded by gastric or intestinal enzymes but is capable of degradation by colonic pectinolytic enzymes. As an alternative to crosslinking of soluble polysaccharides to form insoluble salts, the polysaccharide based system may be coated with pH sensitive polymers. By way of example, chitosan microcores may be prepared and coated with acrylic polymers, such as Eudragit L100 and Eudragit S100 respectively. Eudragit P-4135 F represents a further example of a suitable pH-sensitive polymer, which may be employed to prepare microparticles for colonic delivery.

Multiparticulate systems may be employed, which combine pH sensitive delivery and biodegradation in the colonic environment. By way of example, an inner entrapment matrix of chitosan microcores may be prepared using a technique such as spray drying, followed by application of chitosan microcores microencapsulated within Eudragit polymers by a technique such as oil-in oil solvent evaporation. Upon dissolution of the outer Eudragit coat at appropriate pH the exposed chitosan microcores swell and form a gel barrier in alkaline pH, and, in the colonic region, the chitosan undergoes degradation thereby enhancing release. Similar colonic delivery multiparticulate systems may be based on chitosan microspheres coated with Eudragit L100 or S100. Suitable preparation techniques include emulsion solvent evaporation. The chitosan may be cross-linked with glutaraldehyde.

Polyacrylates represent a further example of a suitable delivery vehicle for use in the present invention. By way of example, a terpolymer of styrene and hydroxyethyl methacrylate cross-linked with a difunctional azo-compound may be employed. The system depends on cleavage of the azo bond by colonic microflora resulting in degradation of polymer. Similarly, a pH responsive poly (methacrylic-g-ethylene glycol) hydrogel may be employed as an oral delivery vehicle. Once inside the basic and neutral environment of the small intestine, the gels rapidly swell and dissociate.

In another embodiment, a microcapsule formulation may be employed for peroral colon-specific delivery. In more detail, aqueous colloidal terpolymers of ethylacrylate/methyl methacrylate/2-hydroxylethyl methacrylate (poly (EA/MME/HEMA), for example as synthesized by emulsion polymerization technique(s) may be employed. These polymers exhibit delayed release profiles which were characterized by a long lag time and subsequent rapid release of the entrapped moiety.

In another embodiment, orally administered nanoparticles may serve as suitable delivery vehicles. By way of example, loaded nanoparticles may be entrapped into pH sensitive microspheres, which serve to deliver the incorporated nanoparticle to the desired colonic site of action. Nanoparticles have a large specific surface, which is indicative of high interactive potential with biological surfaces. Thus, bioadhesion can be induced by binding nanoparticles with different molecules. By way of example, nanoparticles may be prepared from gliadin protein isolate from wheat gluten and then conjugated with lectins (glycoproteins of non-immune origin which provide specific bioadhesion). Accordingly, nanoparticles are provided, which have a high capacity for non-specific interaction with intestine and the binding of lectin provided greater specificity for colonic mucosa.

In one embodiment, a delivery vehicle based on an albumin-chitosan mixed matrix microsphere-filled coated capsule formulation may be employed. In this regard, an antibody preparation of the invention is filled into hard gelatin capsules and enteric coated.

In one embodiment, albumin microspheres may be employed as the oral delivery system.

In one embodiment, squalane oil-containing multiple emulsions may be employed

In one embodiment, poly(lactide-co-glycolide) microspheres may be employed as the oral delivery vehicle.

In one embodiment, a colonic delivery coating comprising a mixture of pH-responsive enteric polymer (Eudragit S) and biodegradable polysaccharide (resistant starch) in a single layer matrix film may be employed. Examples of these delivery vehicles are available commercially, such as from Encap Drug Delivery (Livingston, UK)—particular embodiments include PHLORAL™ and ENCODE™.

In addition (or alternatively) to the above delivery vehicle embodiment, the antibodies/antibody fragments of the present invention may be protected from acid erosion by PEGylation with polyethylene glycol (PEG). PEG of various molecular weights (500-40000 Da) may be coupled to IgG, for example, in a ratio of 2-20 PEG molecules per antibody molecule. We refer to Greenwald, R. B et al (2003) "Effective drug delivery by PEGylated drug conjugates", Advanced Drug Delivery Reviews 55, pp. 217-250. This publication is incorporated in its entirety by reference thereto.

In one embodiment, delivery capsules such as liposomes, micro- or nanocapsules (eg. chitosan nanocapsules) may be chemically modified with poly(ethylene glycol) (PEG). The typical degree of PEGylation is in the range of 0.1% to 5%, such as 0.5% to 2%, for example 0.5% or 1%. The presence of PEG, whether alone or grafted to chitosan, improves the stability of the delivery capsules in the gastrointestinal fluids.

In one embodiment, the antibodies of the present invention may be treated with monomethoxypoly(ethylene) glycols activated by cyanuric chloride, succinimidyl succinate, and tresyl chloride.

PEGylated delivery vehicles such as liposomes, micro- or nanocapsules have an intrinsic ability to accumulate at disease sites and facilitate transfection of target cells. Unlike many viral vectors, PEGylated liposomes are generally considered to be non-immunogenic.

In one embodiment, a branched PEGylating reagent is employed as branched PEG protecting groups are more effective than linear PEG molecules.

Since the antibody formulations of the present invention are for oral delivery, said formulations may include a sweetener, such as vanilla essence, a sugar (eg. glucose, sucrose, etc), sugar alcohols, honey, fruit, syrups (eg. maple syrup, rice syrup, birch syrup, pine syrup, hickory syrup, poplar syrup, palm syrup, sugar beet syrup, sorghum syrup, corn syrup, cane syrup, golden syrup, barley malt syrup, molasses (treacle), brown rice syrup, agave syrup, yacon syrup), acesulfame potassium (also known as Sunett), alitame (also known as aclame), aspartame (also known as Equal or Nutrasweet), anethole, cyclamate, glycyrrhizin, lo han guo, neotame, perillartine, saccharin (also known as Sweet 'n' Low), stevioside, sucralose (also known as SucraPlus and Splenda), or inulin.

Compositions suitable for oral delivery may be in the form of solutions, suspensions or dry powders which are dissolved or suspended in a suitable vehicle prior to use.

In preparing pharmaceutical formulations, the antibodies and/or fragments thereof can be dissolved in the vehicle, and sterilised for example by filtration through a sterile filter using aseptic techniques before filling into suitable sterile vials or ampoules and sealing. Advantageously additives such as buffering, solubilising, stabilising, preservative or bactericidal or suspending and/or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

The dosage ranges for administration of the antibodies of the present invention are those to produce the desired therapeutic effect. It will be appreciated that the dosage range required depends on the precise nature of the antibody or composition, the nature of the formulation, the age of the patient, the nature, extent or severity of the patient's condition, contraindications, if any, and the judgement of the attending physician. Variations in these dosage levels can be adjusted using standard empirical routines for optimisation.

In one embodiment, typical daily dosages are in the range of 5-20 mg (e.g. 8-15 mg or approximately 10 mg) per kg of body weight. The unit dosage can vary from less than 100 mg, but typically will be in the region of 250-500 mg per dose, which may be administered daily (eg. 1×, 2×, 3× or 4× per day) or less frequently (e.g. on alternative days, or say once per week).

It is also within the scope of the invention to use the antibodies of the invention in oral therapeutic methods for the prevention or treatment of CDI in combination with one another, or as an adjunct to, or in conjunction with, other established therapies normally used in the treatment in CDI. For example, the antibodies of the present invention may be administered in conjunction with a suitable antibiotic (e.g. metronidazole and/or vancomycin)

The combination treatment may be carried out in any way as deemed necessary or convenient by the person skilled in the art and for the purpose of this specification, no limitations with regard to the order, amount, repetition or relative amount of the compounds to be used in combination is contemplated.

Definitions Section

*Clostridium difficile* is a species of Gram-positive bacteria of the genus *Clostridium*.

*Clostridium difficile* infection (CDI) means a bacterial infection which affects humans and animals and which results in a range of symptoms from mild self-limiting diarrhoea to life-threatening conditions such as pseudomembranous colitis and cytotoxic megacolon. In this disease, *C. difficile* replaces the normal gut flora and produces cytotoxins which attack and damage the gut epithelium. Primary risk factors for human CDI include: receiving broad-spectrum antibiotics, over 65 years old and hospitalised.

*Clostridium difficile* Toxin A is a family of protein cytotoxins/enterotoxins of approximately 300 kDa in size. Toxin A has an enzyme activity within the N-terminal region which acts to disrupt the cytoskeleton of the mammalian cell causing cell death. There are a number of naturally occurring variants of Toxin A within the strains of *Clostridium difficile* which are call 'toxinotypes'. The various toxinotypes of Toxin A have variations within their primary sequence of usually <10% overall. Examples of suitable Toxin A sequences include SEQ ID Nos: 1 and 3.

*Clostridium difficile* Toxin B is a family of protein cytotoxins of approximately 270 kDa in size which are similar to Toxin A but significantly more cytotoxic. Like Toxin A, Toxin B has an enzyme activity within the N-terminal region which acts to disrupt the cytoskeleton of the mammalian cell causing cell death. There are a number of naturally occurring variants of Toxin B within the strains of *C. difficile* which are call 'toxinotypes'. The various toxinotypes of Toxin B have variations within their primary sequence of usually <15% overall. Examples of suitable Toxin A sequences include SEQ ID Nos: 2 and 4.

Binary Toxin is a two component cytotoxin produced by some but not all strains of *C. difficile*. The binary toxins are similar in action to *Clostridium botulinum* C2 and *Clostridium perfringens* iota toxins, which like *C. difficile* binary toxin, consist of a cell binding fragment of approximately 100 kDa and an enzymically active 'effector' fragment of approx. 50 kDa. Examples of suitable Binary Toxin sequences include SEQ ID Nos: 5 and 6.

As used herein, the term "toxin" encompasses said toxin fragments. The fragment may range from any number of amino acids between 10 and 2700 (e.g. at least 50, 100, 150, 200, 250, 300, 350, 400, 500, 750, 1000, 1500, 2000 or 2500) of the reference toxin. The fragment preferably includes at least one epitope of the gene product in question. The "fragment" may also have a common antigenic cross-reactivity and/or substantially the same in vivo biological activity as the toxin from which it is derived. For example, an antibody capable of binding to a fragment would be also capable of binding to the toxin from which it is derived. Alternatively, the fragment may share a common ability to induce a "recall response" of a T-lymphocyte which has been previously exposed to an antigenic component of a *C. difficile* toxin.

Reference to the term Toxin embraces "variants" thereof—for example, a peptide or peptide fragment having at least 80 or 85 or 90 or 95 or 96 or 97 or 98 or 99 percent amino acid sequence homology with a *C. difficile* Toxin. In a further embodiment, a "variant" may be a mimic of the peptide or peptide fragment, which mimic reproduces at least one epitope of the peptide or peptide fragment.

Reference to the Toxin embraces Toxin "toxoid", which is discussed in more detail below.

Toxinotypes are often used to classify strains of *C. difficile*. Toxinotypes are based on a method which characterises the restriction patterns obtained with the toxin genes. As described above, toxinotypes of Toxins A and B represent variants, by primary amino acid sequence, of these protein toxins.

*Clostridium difficile* Toxoid is used to describe a *C. difficile* toxin (Toxin A, Toxin B or Binary Toxin) or a mixture of *C. difficile* toxins that has been partially or completely inactivated. A toxin is considered inactivated if it has less toxicity (e.g. 100%, 99%, 95% or 90% less toxicity) than untreated toxin as measured by an in vitro cytotoxicity assay or by animal toxicity.

An antibody that binds to a toxin of interest is one capable of binding that toxin with sufficient affinity such that the antibody is useful as a therapeutic agent. An antibody that binds to a toxin of interest is one that binds to a toxin of *C. difficile* with an affinity ($K_a$) of at least $10^4$M.

Toxin neutralising means the action of a substance (e.g. an antibody) which blocks the biological action of one or more of the cytotoxins (Toxin A and/or Toxin B and/or binary toxin) of *C. difficile*. The cytotoxin's biological action being defined as its ability to kill or impair the function of mammalian cells, in particular cells of the mammalian gut epithelium. Toxin neutralising activity of a substance may be measured by its ability to prevent the death of mammalian cells grown in culture.

A therapeutically effective amount refers to the amount of the antibody, which when administered alone or in combination to a patient for treating CDI, or at least one of the clinical symptoms of CDI, is sufficient to affect such treatment of the disease, or symptom. The therapeutically effective amount can vary depending, for example, on the antibody, the infection, and/or symptoms of the infection, severity of the infection, and/or symptoms of the infection, the age, weight, and/or health of the patient to be treated, and the judgment of the prescribing physician. An appropriate therapeutically effective amount in any given instance may be ascertained by those skilled in the art or capable of determination by routine experimentation. A therapeutically effective amount is also one in which any toxic or detrimental effects of the antibody are outweighed by the beneficial effects.

A "prophylactically effective amount" is any amount of the antibody that, when administered alone or in combination to a patient, inhibits or delays the onset or reoccurence of the CDI, or at least one of the clinical symptoms of CDI. In some embodiments, the prophylactically effective amount prevents the onset or reoccurence of the *Clostridium difficile* infection entirely. "Inhibiting" the onset means either lessening the likelihood of the infection's onset, or preventing the onset entirely.

An oral antibody formulation is one which allows a prophylactically effective amount of antibody, when administered orally, to reach the gut and inhibit or delay the onset or reoccurrence of the CDI. Oral formulations prevent or reduce the degradation of antibodies in the gut environment by various mechanisms including the use of protease inhibitors, physical and chemical barriers.

Sheep means any species that falls within the *Ovis* genus (e.g. *Ovis ammon, Ovis orientalis aries, Ovis orientalis orientalis, Ovis orientalis vignei, Ovis Canadensis, Ovis dalli, Ovis nivicola*).

An ovine antibody is an antibody that has at least 100%, 99%, 95%, 90%, 80%, 75%, 60%, 50%, 25% or 10% amino acid sequence identity to an antibody that has been raised in a sheep.

For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Optimal alignment of sequences for comparison may be conducted, for example, by the local homology alignment algorithm of Smith and Waterman [Adv. Appl. Math. 2: 484 (1981)], by the algorithm of Needleman & Wunsch [J. Mol. Biol. 48: 443 (1970)] by the search for similarity method of Pearson & Lipman [Proc. Nat'l. Acad. Sci. USA 85: 2444 (1988)], by computer implementations of these algorithms (GAP, BESTFIT, FASTA, and TFASTA—Sequence Analysis Software Package of the Genetics Computer Group, University of Wisconsin Biotechnology Center, 1710 University Avenue, Madison, Wis. 53705), or by visual inspection [see Current Protocols in Molecular Biology, F. M. Ausbel et al, eds, Current Protocols, a joint venture between Greene Publishing Associates, In. And John Wiley & Sons, Inc. (1995 Supplement) Ausbubel].

Examples of algorithms suitable for determining percent sequence similarity are the BLAST and BLAST 2.0 algorithms [see Altschul (1990) J. Mol. Biol. 215: pp. 403-410; and "http://www.ncbi.nlm.nih.gov/" of the National Center for Biotechnology Information].

In one homology comparison, the identity exists over a region of the sequences that is at least 10 or 20 or 30 or 40 or 50 amino acid residues in length. In another homology comparison, the identity exists over a region of the sequences that is at least 60 or 70 or 80 or 90 or 100 amino acid residues in length.

An "antibody" is used in the broadest sense and specifically covers polyclonal antibodies and antibody fragments so long as they exhibit the desired biological activity. In particular, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al, J. Mol. Biol. 196:901-917, 1987, which are incorporated herein by reference). Preferably, each VHC and VLC is composed of three CDRs and four FRs, arranged from amino-terminus to carboxy-terminus in the following order: FR1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region includes three domains, CHI, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a toxin of *C. difficile* (e.g. Toxin B), e.g., a molecule in which one or more immunoglobulin chains is not full length, but which binds to a toxin. Examples of binding portions encompassed within the term antibody include (i) a Fab fragment, a monovalent fragment consisting of the VLC, VHC, CL and CHI domains; (ii) a F(ab')$_2$ fragment, a bivalent fragment comprising two Fab fragments linked by a disulfide bridge at the hinge region; (iii) a Fc fragment consisting of the VHC and CHI domains; (iv) a Fv fragment consisting of the VLC and VHC domains of a single arm of an antibody, (v) a dAb fragment (Ward et al, Nature 341:544-546, 1989), which consists of a VHC domain; and (vi) an isolated complementarity determining region (CDR) having sufficient framework to bind, e.g. an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science IAI-AT1-A113; and Huston et al. (1988) Proc. Natl. Acad. ScL USA 85:5879-5883). Such single chain antibodies are also encompassed within the term antibody. These are obtained using conventional techniques known to those with skill in the art, and the portions are screened for utility in the same manner as are intact antibodies.

There now follows a brief description of the Figures, which illustrate aspects and/or embodiments of the present invention.

FIG. 1 Measurement of antibodies to Toxin A in serum by affinity chromatography. Antibody binding to Toxin A immobilised onto Sepharose gel which was subsequently eluted. The Figure shows the linear relationship between serum load and eluted Toxin A-specific antibody. Experimental details are provided in Example 9.

Figure 2:
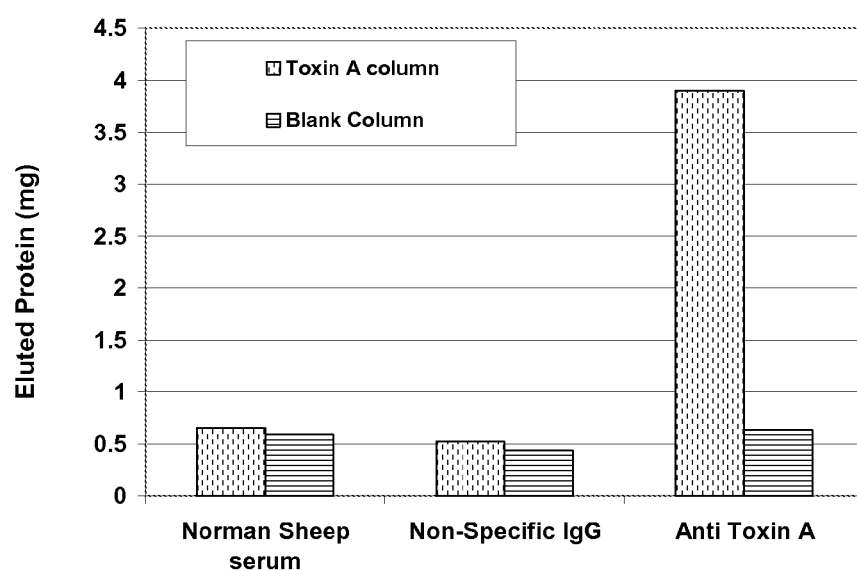

FIG. 2 Measurement of antibodies to Toxin A in serum by affinity chromatography. Antibody binding to Toxin A immobilised onto Sepharose gel which was subsequently eluted. The Figure demonstrates specific antibody in sheep immunised with a toxoid of Toxin A. Antibodies to Toxin A were present in the sheep serum at >3 mg/ml (3 g/liter). Experimental details are provided in Example 9.

Figure 3:
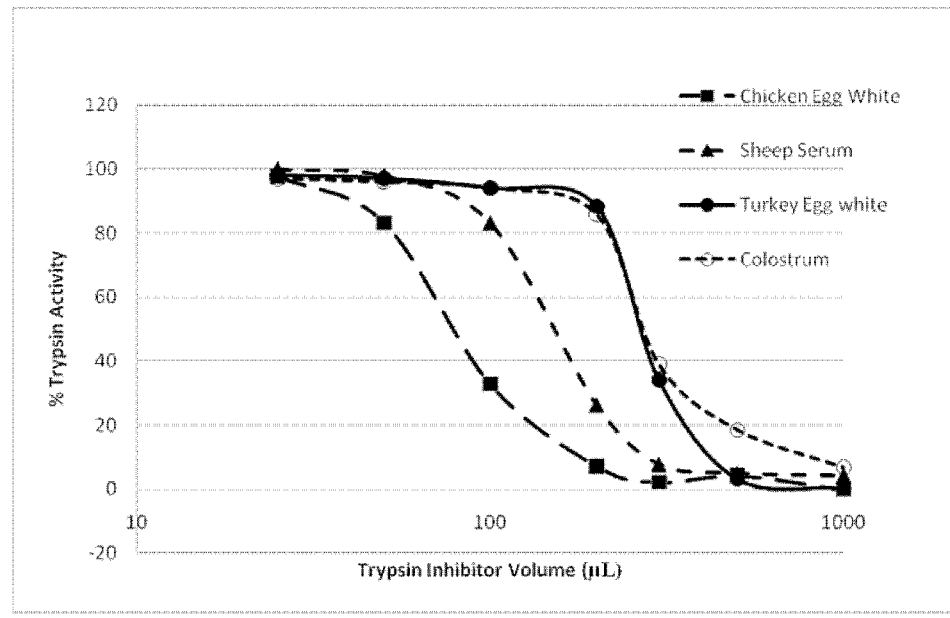

FIG. 3 Inhibition of trypsin activity by egg whites colostrum and normal ovine sheep serum. The data show that trypsin can be inhibited by a variety of naturally occurring inhibitors such as those found in chicken and turkey egg white, colostrum and ovine serum.

Figure 4:
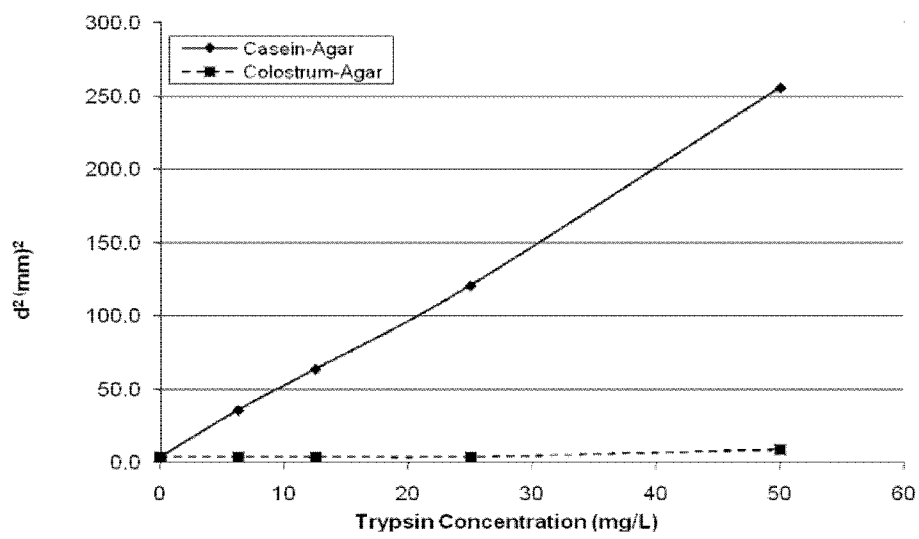

FIG. 4 Trypsin activity in casein and colostrum agar radial protease diffusion plates. Shows the inhibition of trypsin by colostrum using a radial protease diffusion method.

Figure 5:
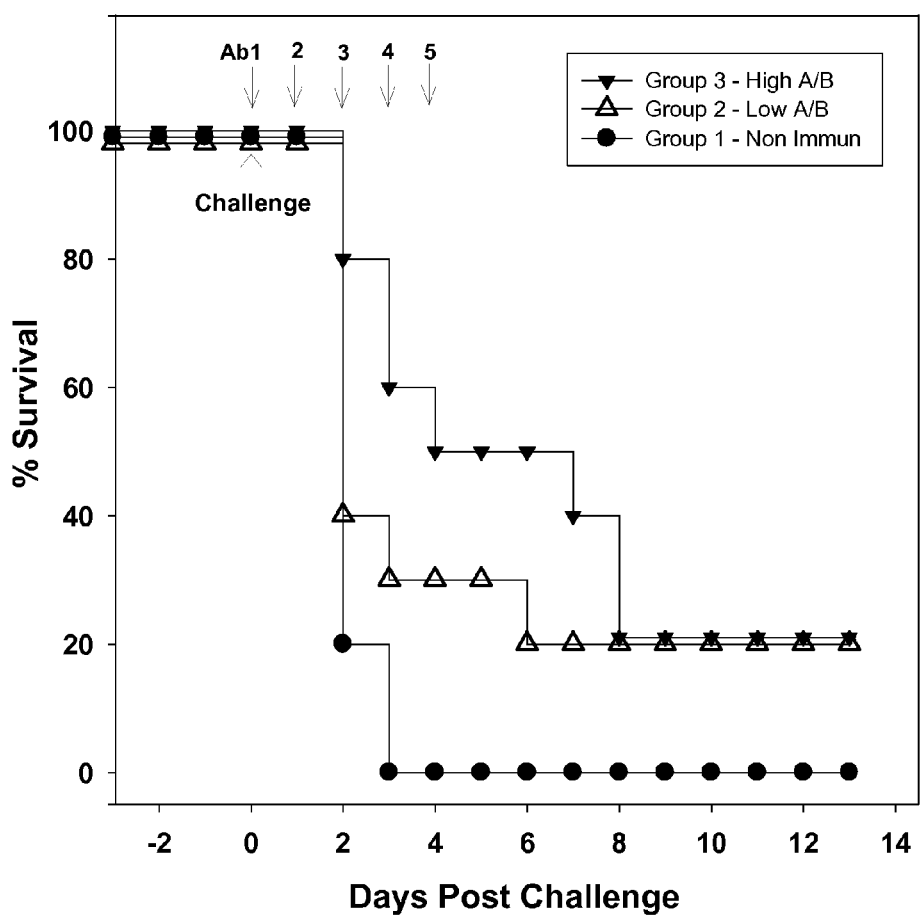

FIG. 5 In vivo experiment 1—Protection of hamsters from CDI by oral delivery of an antibody in the presence of an antacid. These data show that antibodies to *C. difficile* Toxins A and B orally delivered in the presence of an antacid afford protection of hamsters from CDI.

Figure 6:
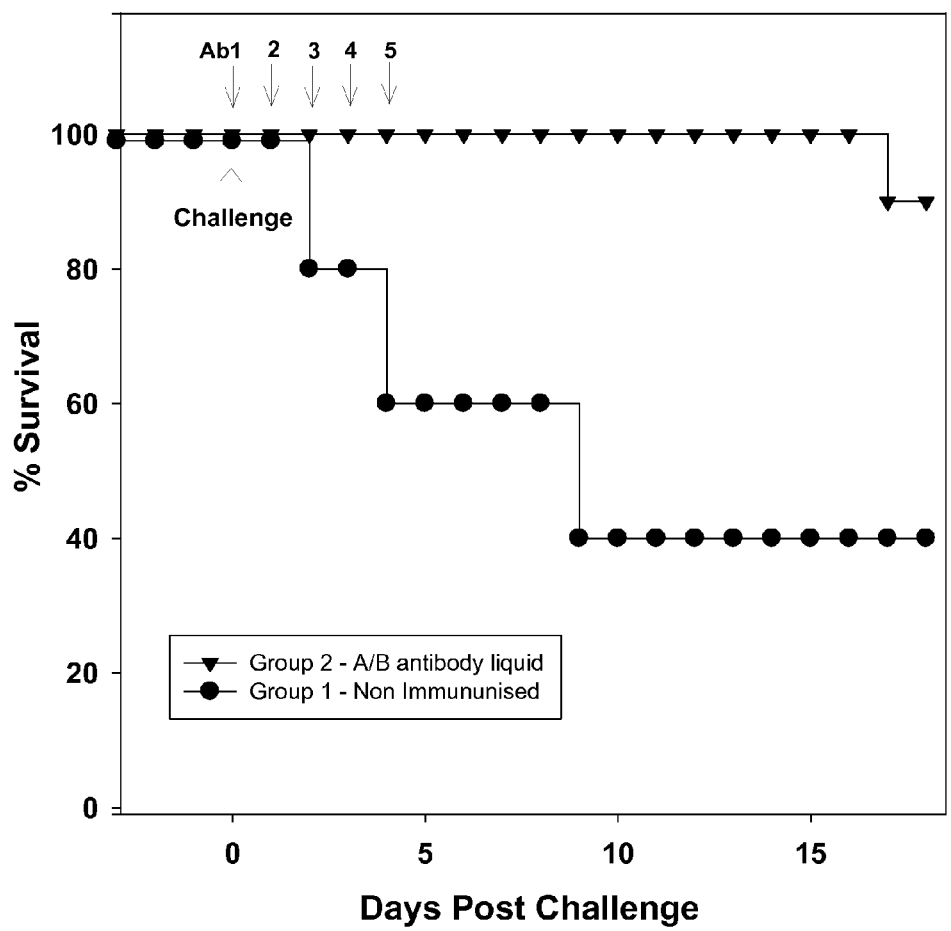

FIG. 6 In vivo experiment 2—Protection of hamsters from CDI by oral delivery of an antibody in the presence of an antacid. These data show that antibodies to *C. difficile* Toxins A and B orally delivered in the presence of an antacid afford protection of hamsters from CDI.

Figure 7:
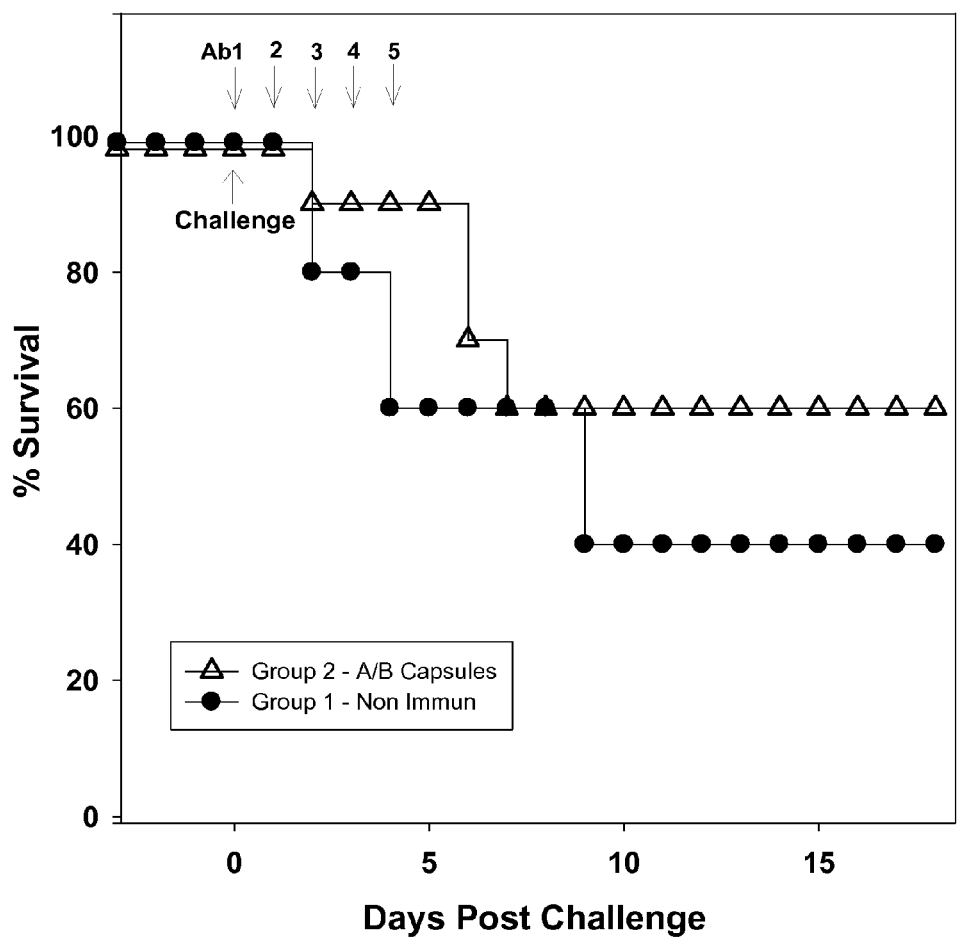

FIG. 7 In vivo experiment 3—Protection of hamsters from CDI by oral delivery of an antibody in an encapsulated form. These data show that antibodies to *C. difficile* Toxins A and B orally delivered in enteric costed capsules afford some protection of hamsters from CDI.

SUMMARY OF EXAMPLES

Example 1 Purification of *C. difficile* Toxins A and B of Toxinotype 0
Example 2 Purification of *C. difficile* Toxins A and B of other Toxinotypes
Example 3 Purification of recombinant *C. difficile* Toxins A and B
Example 4 Purification of *C. difficile* binary toxin
Example 5 Preparation of Toxoids of *C. difficile* Toxins A and B
Example 6 Preparation of antiserum
Example 7 Preparation of antiserum to Toxins A and B of Toxinotype 0
Example 8 Assessment of the neutralising efficacy for antisera to toxins using the in vitro cell assay
Example 9 Quantifying the amount of specific antibody to *C. difficile* toxins in serum using immunoaffinity columns
Example 10 Preparation of antibody inhibitors against trypsin and/or chymotrypsin
Example 11 Preparation of trypsin and/or chymotrypsin inhibitors from egg white (albumin)
Example 12 Demonstration of inhibition of proteolytic activity of trypsin
Example 13 Demonstration of inhibition of proteolytic activity of chymotrypsin
Example 14 Preparation of formulation containing antibody-based inhibitors of trypsin and/or chymotrypsin
Example 15 Preparation of formulation containing drug substance-based inhibitors of trypsin and/or chymotrypsin
Example 16 Preparation of bovine colostrum-ovine antibody formulations
Example 17 Preparation of antibodies modified with polyethylene glycol (PEG)
Example 18 Coating of antibodies with copolymers of methyl acrylate, methyl methacrylate and methacrylic acid (Eudragit)
Example 19 Coating of antibodies with copolymers of alginate/chitosan
Example 20 Coating of antibodies with pectin
Example 21 Assessing the stability of antibody formulations to digestive enzymes using simulated gastric and intestinal conditions
Example 22 Assessment of the in vivo efficacy of ovine antibodies for preventing CDI
Example 23 Assessment of the in vivo efficacy of ovine antiserum for treating CDI
Example 24 Clinical uses of antibody formulations (drug substance)
Example 25 Clinical use of a combination of orally delivered antibody and antibiotics
Example 26 Clinical uses of a combination of systemically and orally delivered antibody formulations

SUMMARY OF SEQ ID NOS

Where an initial Met amino acid residue or a corresponding initial codon is indicated in any of the following SEQ ID NOs, said residue/codon is optional.

1. Protein sequence of *Clostridium difficile* Toxin A-Toxinotype 0
2. Protein sequence of *Clostridium difficile* Toxin B-Toxinotype 0
3. Protein sequence of *Clostridium difficile* Toxin A-Toxinotype III
4. Protein sequence of *Clostridium difficile* Toxin B-Toxinotype III
5. Protein sequence of *Clostridium difficile* Binary toxin fragment A
6. Protein sequence of *Clostridium difficile* Binary toxin fragment B
7. Protein sequence of human trypsin-1 (Swiss Prot Accession P07477)
8. Protein sequence of human trypsin-2 (Swiss Prot Accession P07478)
9. Protein sequence of chymotrypsin-2 (Swiss Prot Accession P17538)

EXAMPLES

Example 1

Purification of *Clostridium difficile* Toxins A and B of Toxinotype 0

A *C. difficile* strain producing Toxinotype 0 Toxins A and B (e.g. VPI 10463) was grown in dialysis sac culture as described (Roberts and Shone (2001) Toxicon 39: 325-333). After growth, the cell slurry was collected from the dialysis sacs and then centrifuged for 10000×g for 30 min and the pH of the resulting supernatant fluid adjusted to pH 7.5 and made 70% saturated with respect to ammonium sulphate. The precipitate containing the toxins was collected by centrifugation then resuspended in 50 mM bistris pH 6.5 buffer and dialysed against the same buffer at 4° C. After dialysis, the solution of crude Toxins A and B was purified by chromatography on Q Sepharose, anion exchange chromatography and the protein peaks containing the toxins eluted with a gradient of NaCl. The peak containing Toxin A was dialysed against 50 mM Hepes pH 7.4 buffer containing 0.5 M NaCl and purified on a Zn chelating column (Zn Sepharose). After loading the toxin and washing the contaminating proteins from the column, the purified Toxin A was eluted with a buffer containing 50 mM Hepes pH 7.4, 20 mM EDTA and 0.1M NaCl. The purified Toxin A was dialysed against 50 mM Hepes pH 7.4 buffer containing 0.15 M NaCl and stored at 4° C. or frozen until use. The peak containing the Toxin B from the initial Q Sepharose column was further purified by chromatography on a column of high resolution Mono Q anion exchange resin. After loading the toxin onto the column in 50 mM bistris pH 6.5 buffer, the purified Toxin B was eluted with a NaCl gradient and the fractions containing the toxin pooled. The purified Toxin B was dialysed against 50 mM Hepes pH 7.4 buffer containing 0.15 M NaCl and stored at 4° C. or frozen until use.

Example 2

Purification of C. difficile Toxins A and B of Other Toxinotypes

Toxins A and B representing any of the known Toxinotypes are purified as described in Example 1. Known C. difficile strains producing Toxins A and B of various toxinotypes are given in Table 1 and by selecting the required strain for purification, Toxins A and B of the required Toxinotype are purified. Alternatively, C. difficile may be toxinotyped as described previously (Rupnik et al. (1998) J. Clinical Microbiol. 36: 2240-2247; Rupnik et al. (2001) Microbiology 147: 439-447) until a C. difficile strain producing toxin of the desired toxinotype is obtained. Each of these references is incorporated in its entirety by reference.

To produce Toxinotype III Toxins A and B, C. difficile strain R20291 (also known as NCTC 13366) was grown in dialysis sac culture as described (Roberts and Shone (2001) Toxicon 39: 325-333, which is incorporated in its entirety by reference) and the toxins purified as described in Example 1.

Example 3

Purification of Recombinant C. difficile Toxins A and B

Amino acid sequences of examples of the C. difficile Toxins A and B are shown Seq IDs 1 to 4. Genes encoding these peptides are available commercially with codon bias for any desired expression host (e.g. E. coli, Pichia pastoris). Peptides are expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed polypeptides are purified by a combination of hydrophobic interaction chromatography, ion exchange chromatography and ceramic hydroxyl apatite chromatography. Alternative chromatographic techniques well known to the art of protein purification, such as size exclusion chromatography and/or affinity chromatography, may be used. For the latter, recombinant fragments may be expressed with affinity purification tags (e.g. Histidine-6, streptag) such as described in the pET vector Expression System Manual, 11th Edition published by Merck KGaA, Darmstadt, Germany.

To produce a recombinant toxin from a C. difficile toxinotype for which the sequence is unknown, DNA is extracted and the toxin sequence(s) derived by standard molecular biology methods. The recombinant toxin is then expressed from a synthetic gene as above.

Example 4

Purification of Recombinant C. difficile Binary Toxin

Amino acid sequences of the C. difficile binary toxin fragments A and B are shown Seq IDs 5 and 6, respectively. Genes encoding these peptides are available commercially with codon bias for any desired expression host (e.g. E. coli, Pichia pastoris). Peptides are expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed peptides are purified by a combination of hydrophobic interaction chromatography, ion exchange chromatography and ceramic hydroxyl apatite chromatography. Alternative chromatographic techniques well known to the art of protein purification, such as size exclusion chromatography and/or affinity chromatography, may be used.

Recombinant fragments are expressed with affinity purification tags (e.g Histidine-6, streptag) such as described in the pET vector Expression System Manual, 11th Edition published by Merck KGaA, Darmstadt, Germany (herein incorporated in its entirety). Details of the purification of the binary toxin components are described in Sundriyal et al. 2010 (Protein Expression & Purification 74: 42-48), which is herein incorporated in its entirety.

The peptides may be expressed with a histidine-6 purification tag to improve solubility using a commercially available expression vector such as pET52b and refolded by on-column refolding techniques as described by the review of Lia et al. and references contained therein (Lia M et al (2004) Protein Expression & Purification 33, 1-10), which is hereby incorporated by reference thereto.

Example 5

Preparation of Toxoids of C. difficile Toxins A and B

Purified C. difficile toxins at a concentration of between 0.2-2 mg/ml are dialysed against a suitable buffer (e.g. 10 mM Hepes buffer pH 7.4 containing 150 mM NaCl) and then formaldehyde added at a final concentration of between 0.05 and 0.5% and incubated for between 1 and 25 days at 35° C. After incubation, the formaldehyde is removed by dialysis. Conditions for the treatment with formaldehyde may vary slightly between peptides and final conditions are fine-tuned accordingly on the basis of outcome of protective efficacy evaluations.

Example 6

Preparation of Antiserum

A number of conventional factors are taken into consideration during the preparation of antiserum in order to achieve the optimal humoral antibody response. These include: breed of animal; choice of adjuvant; number and location of immunisation sites; quantity of immunogen; and number of and interval between doses.

Conventional optimisation of these parameters it is routine to obtain specific antibody levels in excess of 6 g/liter of serum.

For sheep, 2 ml of buffer solution containing between 10 and 500 μg of *C. difficile* antigen is mixed with 2.6 ml of Freund's adjuvant. The complete form of the adjuvant is used for the primary immunisation and incomplete Freund's adjuvant for all subsequent boosts. Mixing of the adjuvant is carried out for several minutes to ensure a stable emulsion. About 4.2 ml of the antigen/adjuvant mixture is used to immunise each sheep by im injection and spread across 6 sites including the neck and all the upper limbs. This is repeated every 28 days. Blood samples are taken 14 days after each immunisation. Once adequate antibody levels are achieved, larger volumes are taken (10 ml/kg body weight) into sterile bags. The bags are rotated slowly to accelerate clotting, centrifuged for 30 min at 4500×g and the serum removed under aseptic conditions and pooled. Any animal showing low titres to the desired *C. difficile* antigen is removed from the flock.

Example 7

Preparation of Antiserum to Toxins A and B of Toxinotype 0

Toxins A and B from a toxinotype 0 strain (e.g. VPI 10463) were prepared as described in Example 1. Alternatively, Toxin A or B may be made by recombinant methods as described by Yang et al. (Yang G, Zhou B, Wang J, He X, Sun X, Nie W, Tzipori S, Feng H (2008) Expression of recombinant *Clostridium difficile* toxin A and B in *Bacillus megaterium*. BMC Microbiol. 8: 192). Purified Toxins may be toxoided as described in Example 5.

For immunisation of sheep with Toxoids A or B, 2 ml of buffer solution containing between 10 and 500 μg of either *C. difficile* Toxoids A or B was mixed with 2.6 ml of Freund's adjuvant. The complete form of the adjuvant was used for the primary immunisation and incomplete Freund's adjuvant used for all subsequent boosts. Mixing of the adjuvant was carried out for several minutes to ensure a stable emulsion. After mixing, approx 4.2 ml of the antigen/adjuvant mixture was used to immunise each sheep by im injection and spread across 6 sites including the neck and all the upper limbs. This was repeated every 28 days and serum samples collected 14 days after each immunisation. Once adequate antibody levels were achieved, larger production sample were taken (10 ml/kg body weight) into sterile bags. The bags were rotated slowly to accelerate clotting, centrifuged for 30 min at 4500×g and the serum removed under aseptic conditions and pooled. Any animal showing low titres to either Toxins A or B was omitted from the flock.

Example 8

Assessment of the Neutralising Efficacy for Antisera to Toxins Using the In Vitro Cell Assay The toxin neutralizing activity of the antisera against *C. difficile* Toxins is measured by cytotoxicity assays using Vero cells. A fixed amount of either purified *C. difficile* Toxin A or Toxin B is mixed with various dilutions of the antibodies, incubated for 1 h at 37° C. and then applied to Vero cells growing on 24-well tissue culture plates. Both Toxin A and B possess cytotoxic activity which results in a characteristic rounding of the Vero cells over a period of 24-72 h. In the presence of neutralising antibodies this activity is inhibited and the neutralising strength of an antibody preparation is assessed by the dilution required to neutralise the effect of a designated quantity of either Toxin A or B.

Data demonstrating the neutralising activity of ovine antibody to *C. difficile* Toxin A are shown in Table 2. In this experiment, various dilutions of ovine antibody were mixed with Toxin A at a final concentration of 50 ng/ml and incubated for 1 h at 37° C. and then applied to Vero cells as above and incubated at 37° and monitored over a period of 24-72 h. The antibody dilutions which protect the cells against the cytotoxic effects of the Toxin A were calculated. Table 2 shows that sheep immunised for a period of 14 weeks had a neutralising titre of 16000 (i.e. a 1/16000 dilution of the serum protected the cells from the cytotoxic effects of Toxin A).

TABLE 2

Neutralisation Titres of Ovine Antibodies Raised Against Formaldehyde-Treated Toxin A

| Number of vaccinations | Immunisation period (weeks) | Antibody Neutralising Titre¶ |
|---|---|---|
| 0 | 0 | <10 |
| 1 | 0 | <10 |
| 2 | 6 | 2000 |
| 3 | 10 | 4000 |
| 4 | 14 | 16000 |

¶Dilution of serum required to neutralise 50 ng/ml of Toxin A in cell neutralisation assays For antiserum produced by Toxin B (Toxoid), a 14 week schedule with one immunisation of 250 μg/dose given to each animal every 4 weeks resulted in antiserum with an antiserum titre of >1/10000 (using a fixed concentration of Toxin B at 0.5 ng/ml).

TABLE 3

Neutralisation Titres of Ovine Antibodies Raised Against Formaldehyde-Treated Toxin B
The data show that higher immunising doses of Toxoid B antigen results in a better ovine toxin-neutralising immune response as measured by Vero cell cytotoxicity assays. These assays are described in Example 8.

| Immunising dose (μg) of *C. difficile* Toxoid B | Neutralisation titre against Toxin B in cell assays* |
|---|---|
| Sheep anti toxoid B (10ug) | 1/1280 |
| Sheep anti toxoid B (50ug) | 1/2560 |
| Sheep anti anti toxoid B (250ug) | 1/10240 |

All animals were given 2 doses of formaldehyde-treated Toxin B
*Dilution of serum required to completely neutralise 0.5 ng/ml of Toxin B in cell neutralisation assays Tables 4, 5 and 6 demonstrate that very high toxin-neutralising tires (>20,000) units per ml of serum can be obtained in sheep by immunisation with toxoids derived from Toxin A and B. These titres are significantly higher than that previously reported in other species.

TABLE 4

Neutralisation titres of ovine antibodies raised using different doses formaldehyde-treated Toxin A
The data show that after an extended immunisation period, very high titres can be obtained with various toxoid doses in sheep. These assays are described in Example 8.

| Immunising dose (μg) of *C. difficile* Toxoid A | Dosing | Neutralisation titre/ml serum against Toxin A (50 ng/ml)¶ |
|---|---|---|
| Sheep anti toxoid A (25 μg) | 5 doses over 22 weeks | 25,600 |

TABLE 4-continued

Neutralisation titres of ovine antibodies raised using different doses formaldehyde-treated Toxin A
The data show that after an extended immunisation period, very high titres can be obtained with various toxoid doses in sheep. These assays are described in Example 8.

| Immunising dose (μg) of *C. difficile* Toxoid A | Dosing | Neutralisation titre/ml serum against Toxin A (50 ng/ml)¶ |
|---|---|---|
| Sheep anti toxoid A (100 μg) | 5 doses over 22 weeks | 25,600 |
| Sheep anti toxoid A (250 μg) | 5 doses over 22 weeks | 25,600 |

¶Dilution of serum required to neutralise 50 ng/ml of Toxin A in cell neutralisation assays

TABLE 5

Neutralisation titres of ovine Antibodies raised against formaldehyde-treated toxin B
The data show that a 250 μg immunising dose of Toxoid B antigen over an extended immunisation period results in very high toxin neutralising titres. These assays are described in Example 8.

| Immunising dose (μg) of *C. difficile* Toxoid B | Dosing | Neutralisation titre/ml serum against Toxin B (0.5 ng/ml)* |
|---|---|---|
| Sheep anti toxoid B (10 μg) | 5 doses over 18 weeks | 1,280 |
| Sheep anti toxoid B (50 μg) | 5 doses over 18 weeks | 5,120 |
| Sheep anti toxoid B (250 μg) | 5 doses over 18 weeks | 20,480 |

*Dilution of serum required to completely neutralise 0.5 ng/ml of Toxin B in cell neutralisation assays

TABLE 6

Neutralisation titres of purified IgG obtained against by immunisation of formaldehyde-treated Toxins A and B
The table show the high toxin-neutralisation titres of purified IgG derived from ovine antiserum by precipitation of other proteins with caprylic acid

| Purified sheep IgG | Neutralisation titre against Toxin A (50 ng/ml) | Neutralisation titre against Toxin B (0.5 ng/ml) |
|---|---|---|
| IgG (50 mg/ml) from Toxoid A immunised sheep | 40,000 | N/A |
| IgG (50 mg/ml) from Toxoid B immunised sheep | N/A | 20,000 |

Example 9

Quantifying the Amount of Specific Antibody to *C. difficile* Toxins in Serum Using Immunoaffinity Columns Column Preparation CNBr-activated Sepharose 4 Fast Flow (0.5 g dry weight) is weighed into a suitable clean container (glass or plastic). About 10 ml of diluted hydrochloric acid (1 mM) is added to swell the gel and, after 20-30 min, the gel is transferred to a 10-mL glass column and washed with a further 20 mL of HCl (1 mM), followed by 20 mL of coupling buffer (sodium bicarbonate, 100 mM, pH 8.3, containing 500 mM sodium chloride). Toxin (Toxin A, Toxin B or a binary toxin fragment solution (1 mL) at a concentration of 1 mg/mL is diluted to 5 mL with coupling buffer and added to the column containing the activated gel and the contents mixed gently until the gel is re-suspended and rotated at room temperature overnight (16-18 hr). The column is then drained and 5 ml of blocking reagent (ethanolamine solution, 1M) added, mixed gently and rotated for 2 hr at room temperature. Next, the column is washed with 20 mL coupling buffer followed by 20 mL of elution buffer (glycine solution 100 mM, pH 2.5). This step is repeated twice. The column is finally washed with 20 mL of assay buffer (sodium phosphate buffer, 10 mM, pH 7.4 containing 500 mM sodium chloride and sodium azide at a final concentration of 1 g/L) and stored in 3-5 mL of assay buffer at 2-8° C. until used.

Column Assessment

The specific binding and non-specific capacity of the column is typically assessed prior to use. The column is removed from the refrigerator and allowed to equilibrate to room temperature and then washed with 25 mL of assay buffer. Increasing volumes of the product (whole antisera, purified IgG, Fab or $F(ab')_2$) are individually loaded onto the column and mixed end-over-end gently for 1 hr at room temperate. The unbound fraction is washed off with 25 mL of assay buffer and the bound fraction then eluted from the column with 20 ml of elution buffer (glycine buffer 100 mM, pH 2.5). The protein content of the eluted fraction is determined spectrophotometrically at 280 nm using an extinction coefficient relevant to the product namely 1.5 for sheep IgG (Curd et al., 1971) or 1.4 for sheep Fab and $F(ab')_2$ (Allen, 1996). A saturation curve is obtained by plotting the amount of eluted protein against the volume loaded.

Non-specific binding (NSB) is assessed using normal sheep serum (NSS) prior to immunisation. Thus it is necessary to differentiate between this and binding due to some specific antibodies in normal serum (since all animals will have been exposed to *C. difficile*). FIG. 1 demonstrates the typical binding capacity curve showing an increase in specific binding as a result of increasing the antiserum loading volume. There is a little change in non-specific binding (NSB) with the increase of loading volume. The 0.5 g (1.5-2.0 ml swelled gel) contain 1 mg of toxin (coupling ratio of 2 mg/g) is sufficient for the volume of specific antisera (0.5-4 mL) loaded. In this regard, 1 ml is the recommended loading volume for easy and convenient calculations.

The coefficient of variation for 10 replicates (between assay CV) is approximately 6%. There is no decline in the column capacity with time (estimated when used 80-100 times). This indicates that there is no leaching of the toxin from the column.

Affinity Column for Product Assessment

The column is used for GMP/GLP assessment of in-process and final product viz whole antisera, purified IgG, Fab and $F(ab')_2$. It is also used to assess and monitor the immune response of the immunised animals and to detect antitoxin antibodies in human samples.

The column is removed from the refrigerator and allowed to equilibrate to room temperature when it is washed with 25 mL of assay buffer. Product (1 mL) is added to the column and mixed end-over-end gently for 1 hr at room temperature following which the unbound fraction is washed off with 25 mL of assay buffer (sodium phosphate buffer, 10 mM, pH 7.4 containing 500 mM sodium chloride and sodium azide at a final concentration of 1 g/L). The bound fraction is then eluted with 20 ml of elution buffer (glycine buffer 100 mM, pH 2.5) and its protein content determined spectrophotometrically at 280 nm using an extinction coefficient relevant to the product. FIG. 2 shows the analysis of serum from sheep immunised with a toxoid of Toxin A.

Example 10

Preparation of Antibody Inhibitors Against Trypsin/Chymotrypsin

Suitable antigens may be prepared, for example, by protocol (a) or (b) below.

(a) Immunisation with Native and/or Toxoided Trypsin and Chymotrypsin

Human trypsin-1, trypsin-2 and chymotrypsin are obtained commercially. These enzymes are dialysed into a suitable buffer such as MES (50 mM, pH 6.0) containing 150 mm NaCl and toxoided by addition of 0.2% formaldehyde followed by incubation for between 1 and 14 days at between 4 and 37° C.

(b) Immunisation with Recombinant Trypsin and Chymotrypsin

Amino acid sequences of the principal human trypsin and chymotrypsin are shown SEQ IDs 7, 8 and 9, respectively. Catalytically inactive antigens are provided, for example, by changing one or more of the underlined residues (e.g. histidine, aspartate, serine) to an amino acid residue such as analine (or a conservative substitution thereof). Genes encoding these modified trypsin and chymotrypsin peptides are commercially available with codon bias for any desired expression host (e.g. *E. coli, Pichia pastoris*). Peptides are expressed from these genes using standard molecular biology methods (e.g. Sambrook et al. 1989, Molecular Cloning a Laboratory Manual, Second Edition, Cold Spring Harbor Laboratory Press, Cold Spring Harbor, N.Y.) and the resulting soluble expressed peptides are purified by a combination of hydrophobic interaction chromatography, ion exchange chromatography and ceramic hydroxyl apatite chromatography. Alternative chromatographic techniques well known to the art of protein purification, such as size exclusion chromatography and/or affinity chromatography, may be used.

Recombinant fragments may also be expressed with affinity purification tags (e.g. Histidine-6, streptag) such as described in the pET vector Expression System Manual, 11th Edition published by Merck KGaA, Darmstadt, Germany.

The peptides may be expressed with a histidine-6 purification tag to improve solubility using a commercially available expression vector such as pET52b and refolded by on-column refolding techniques as described by the review of Lia et al. and references contained therein (Lia M et al (2004) Protein Expression & Purification 33, 1-10), which is hereby incorporated by reference thereto.

The above antigens, either singularly or in various combinations, are used to generate antibodies by the following method. For preparation of antibodies in sheep, 2 ml of buffer solution containing between 10 and 500 µg of trypsin and/or chymotrypsin antigen(s) is mixed with 2.6 ml of Freund's adjuvant. The complete form of the adjuvant is used for the primary immunisation and incomplete Freund's adjuvant for all subsequent boosts. Mixing of the adjuvant is carried out for several minutes to ensure a stable emulsion. About 4.2 ml of the antigen/adjuvant mixture is used to immunise each sheep by im or is injection and spread across 6 sites including the neck and all the upper limbs. This is repeated every 28 days. Blood samples are taken 14 days after each immunisation. Once adequate antibody levels are achieved, larger volumes are taken (10 ml/kg body weight) into sterile bags. The bags are rotated slowly to accelerate clotting, centrifuged for 30 min at 4500×g and the serum removed under aseptic conditions and pooled. Any animal showing low titres to the desired *C. difficile* antigen is removed from the flock.

Example 11

Preparation of Trypsin/Chymotrypsin Inhibitors from Egg White

Egg white contains only traces of lipids and carbohydrates and consists largely of protein. Protein fractions containing the predominant protease inhibitors, ovomucoid and ovostatin can be readily obtained by precipitation or by standard protein purification methods such as ion exchange chromatography and size exclusion. In one such method, the white of eggs are separated from the yolk and suspended in 2 volumes of 1% NaCl in 50 mM Tris-HCl (pH 7.5) containing 1 mM EDTA and homogenized with an ultrasonic disruptor before being centrifuged at 15,000×g for 20 min. The supernatant fluid is then dialyzed against 10 mM Tris-HCl buffer, pH 7.5, and applied to a Q-Sepharose column. The column is eluted with 10 mM Tris-HCl buffer containing NaCl with a linear gradient from 0 M to 0.5 M to obtain various peaks of the protease inhibitors. Crude or purified protein fractions containing protease inhibitor activity against trypsin and chymotrypsin (as assessed in Examples 12 and 13) may be optionally combined to produce an enriched protease inhibitor protein mixture.

In other methods, concentrated mixtures of the egg white protease inhibitors are readily obtained by precipitation of the egg white proteins with various agents such e.g. acetone (Lineweaver & Murray (1947) J. Biol. Chem. 171, 565-581) or by precipitation with up to 70% ammonium sulphate. Alternatively, egg white protease is commercially available.

Example 12

Demonstration of Inhibition of Proteolytic Activity of Trypsin

Trypsin activity is measured using the L-BAPNA assay: This method is based on the spectrophotometric determination of the breakdown products of benzoyl-DL-arginine-p-nitroanilide (DL-BAPNA) by a given concentration of trypsin, in the presence and absence of the inhibitor (Kakade et al., 1974), which is incorporated in its entirety by reference.

Materials

Assay buffer: Tris-buffer (0.05M, pH 8.2) containing 0.02M $CaCl_2$

Substrate solution: Benzoyl-DL-arginine-p-nitroanilide hydrochloride (DL-BAPNA) (10 mg) was dissolved in 0.2 mL of dimethyl sulphoxide (DMS) and diluted to 20 mL with assay buffer. The solution was prepared daily and stored at 37° C. while in use.

Trypsin solution (0.2 mg/mL: Trypsin 40 mg was dissolved into 200 mL of diluted HCl (0.001M). The solution can be stored at 2-8° C. for 2 weeks.

Stopping solution: acetic acid solution (30% v/v) was prepared by mixing a glacial acetic acid (30 mL) with distilled water (70 mL).

Procedure

Various volumes of trypsin inhibitor (e.g. antibodies, or egg white, or egg white derivatives or colostrum) were pipetted into duplicate sets of test tubes and adjusted to 1 mL with assay buffer. Control samples contained equivalent protein concentrations of non-specific protein or antibody. Trypsin solution was added to each tube followed by 1 mL of DL-BAPNA solution. After incubation for 5 minutes at room temperature, the reaction was terminated by adding 0.5 mL of stopping solution and the absorbance of each tube measured spectrophotometrically at 410 nm. Blank samples were prepared by adding the stopping solution prior to the substrate solution.

Test sample containing effective trypsin inhibitors were found to inhibit the cleavage of DL-BAPNA and hence the increase in absorbance at 410 nm compared to the control samples.

Demonstration of Trypsin-Neutralising Activity in Various Inhibitor Preparations (e.g. Egg White and Colostrum)
Reagents Chicken egg white was separated manually from the yolk and diluted at a ratio of 1:1 with assay buffer (Tris-buffer, 0.05M, pH 8.2, containing 0.02M $CaCl_2$). A highly purified Type II trypsin inhibitor from turkey egg white (Sigma UK) and Bovine colostrum (Colostrum UK ltd) reagent were prepared at concentrations of 0.4 g/L and 100 g/L in assay buffer, respectively.

Procedure

Various volumes of trypsin inhibitors (chicken egg white, turkey egg white Type II trypsin inhibitor, normal ovine serum; bovine colostrum) were pipetted into duplicate sets of test tubes and adjusted to 1 mL with Tris-buffer, (0.05M, pH 8.2) containing 0.02M $CaCl_2$. Trypsin solution (0.2 mg/ml) was prepared in 1 mM hydrochloric acid and 1 ml was added to each tube followed by 1 ml of DL-BAPNA solution (0.5 mg/ml). After incubation for 5 min at room temperature, the reaction was terminated by adding 0.5 ml of Acetic acid solution (30% v/v) and the absorbance of each tube measured spectrophotometrically at 410 nm. Blank samples were prepared by adding the stopping solution prior to the substrate solution.

For the tubes containing colostrum, sodium sulphate solution (360 g/l) was added in an equal volume and centrifuged for 45 min at 3500 rpm to precipitate out the casine protein. The supernatant of each tube was collected and the absorbance measured as above.

Result

Inhibition of trypsin activity was demonstrated in all preparations tested including ovine serum, bovine colostrum and chicken and turkey egg whites (FIG. 3). Trypsin inhibition is due to the intrinsic inhibitors present in these preparations.

Demonstration of Inhibition of Trypsin by Colostrum by Radial Protease Diffusion This technique was used to measure the trypsin inhibition activity of colostrum. Diffusion plates were prepared by dissolving 0.5 g of agar (Bio-Rad) in 50 ml of assay buffer (Tris-buffer, 0.05M, pH 8.2; containing 0.02M $CaCl_2$) in a boiling water bath, cooling to 60° C. and adding 50 ml of a casein or colostrum suspension (20 g/l) in assay buffer to give a final concentration of 10 g/L. The warm suspension was poured in 90 cm plastic plates to yield a layer 2.5 mm thick which was allowed to solidify in a humid chamber at room temperature for 2 hours. Wells of 5 mm in diameter were punched out and 20 μL of various porcine trypsin concentrations (6.25, 12.5, 25 and 50 mg/L) were loaded to each well. The plates were incubated at room temperature (22° C.) in a humid chamber for 24 hr. The diameters ($d^2$ $mm^2$) of the transparent circles resulting from trypsin diffusion and digestion of the casein were measured and plotted against the trypsin concentration (FIG. 4).

The results showed that colostrum at a concentration of 10 g/L inhibited the proteolytic activity of the trypsin at the tested concentrations.

Protection of Ovine Immunoglobulin from Digestion by Trypsin by in Presence of Chicken Egg White Ovine IgG was purified by caprylic and formulated at 25 g/L into sodium citrate saline buffer pH 6.0. Porcine trypsin was dissolved in 1 mM hydrochloric acid to a concentration of 2 g/L and added to the ovine IgG at a concentration of 5% w/w of the total protein. An equal volume of chicken egg white diluted in a ratio of 1:1 with Tris-buffer, 0.05M, pH 8.2; containing 0.02M $CaCl_2$, was added and the mixture incubated at 37° C. for 20 h. The digestion was monitored by size exclusion gel filtration (FPLC).

The results showed that chick egg white completely protected the IgG from digestion with trypsin. The control experiment has demonstrated that under these experimental conditions and in the absence of chicken egg white, trypsin completely digested the IgG to Fab and small fragments.

Example 13

Demonstration of Inhibition of Proteolytic Activity of Chymotrypsin

The protease reaction velocity is determined by measuring an increase in absorbance at 256 nm resulting from the hydrolysis of benzoyl-L-tyrosine ethyl ester. One unit hydrolyzes one micromole of benzoyl-L-tyrosine ethyl ester (BTEE) per minute at pH 7.8 and 25° C. under the specified conditions.

Reagents 0.08 M Tris.HCl buffer, pH 7.8 containing 0.1 M calcium chloride 0.00107 M Benzoyl-L-tyrosine ethyl ester (BTEE) in 50% w/w methanol (63 ml absolute methanol added to 50 ml reagent grade water)

Dissolve enzyme at one mg/ml in 0.001 N HCl. Dilute in 0.001 N HCl to 10-30 μg/ml for assay.

Procedure

Adjust the spectrophotometer to 256 nm and 25° C.

Various volumes of chymotrypsin inhibitor (e.g. antibodies, egg white derivatives, or colostrum) were pipetted into duplicate sets of test tubes and adjusted to 1.5 ml with assay buffer (0.08 M Tris.HCl buffer, pH 7.8 with 0.1 M $CaCl_2$). Control samples contained equivalent protein concentrations of non-specific protein or antibody.

Add to the above 1.4 ml of 0.00107 M BTEE

Incubate in spectrophotometer at 25° C. for 4-5 minutes to achieve temperature equilibrium and record blank rate, if any. Add 0.1 ml of appropriately diluted enzyme and record increase in absorbance at 256 nm for 4-5 minutes. Calculate ΔA256/min from the initial linear portion of the curve.

Test sample containing effective chymotrypsin inhibitors were found to inhibit the cleavage of DL-BAPNA and hence the increase in absorbance at 256 nm compared to the control samples Example 14

Preparation of a Formulation Containing Antibody Inhibitors to Trypsin and Chymotrypsin Formulation of antibodies effective at preventing and treating CDI when delivered orally may contain the following components:

Ovine antibodies against *difficile* Toxins A and/or B
optionally, ovine antibodies against *difficile* binary toxin
ovine antibodies that have inhibitory activity against human trypsin(s) and/or ovine antibodies that have inhibitory activity against human chymotrypsin(s)

optionally, an antacid component to assist in the neutralisation of stomach acid optionally, a flavouring such as a sweetener to make the mixture more palatable In detail, a typical formulation contains:

ovine antibodies to Toxin A and/or B at 5-50 mg/ml optionally, ovine antibodies to binary toxin at 5-50 mg/ml antibody inhibitors of trypsin and/or chymotrypsin at 5-50 mg/ml optionally, an antacid component (e.g. magnesium hydroxide or sodium bicarbonate) at, for example, a concentration of 0.05 to 0.5 M optionally, a flavouring agent (e.g. a sweetener) such as vanilla essence

Example 15

Preparation of a Formulation Based on Drug Substance (e.g. Egg-Derived) Inhibitors of Trypsin and/or Chymotrypsin Formulation of antibodies effective at preventing and treating CDI when delivered orally contain the following components:

ovine antibodies against *difficile* Toxins A and/or B optionally, ovine antibodies against *difficile* binary toxin crude or purified protein fractions from hen eggs containing the protease inhibitor activity against trypsin and chymotrypsin as described in Example 11 optionally, an antacid component to assist in the neutralisation of stomach acid optionally, a flavouring such as a sweetener to make the mixture more palatable In detail, a typical formulation contains:

ovine antibodies to Toxin A and/or B at 5-50 mg/ml optionally, ovine antibodies to binary toxin at 5-50 mg/ml hen egg white derived protease inhibitors (as purified as described in Example 11) at a concentration of 5-50 mg/ml optionally, an antacid component (e.g. magnesium hydroxide or sodium bicarbonate) at, for example, a concentration of 0.05 to 0.5 M optionally, a flavouring agent (e.g. a sweetener) such as vanilla essence

Example 16

Preparation of Bovine Colostrum—Ovine Antibody Formulations

Ovine antibody formulations with bovine colostrum may be prepared in several ways:

By mixing liquid bovine colostrum with a solution of ovine IgG.

By mixing lyophilised or dried bovine colostrum with liquid IgG.

By mixing liquid bovine colostrum with lyophilised ovine IgG.

By mixing lyophilised or dried bovine colostrum with lyophilised ovine IgG and reconstituting with water or buffer saline to the desired concentration.

In the above formulations, the colostrum component has a final concentration of between 10% and 90% of its initial concentration. The final concentration of IgG is ideally between 10-50 mg/ml.

Formulation of antibodies effective at preventing and treating CDI when delivered orally contain the following components:

ovine antibodies against *difficile* Toxins A and/or B optionally, ovine antibodies against *difficile* binary toxin a colostrum component has a final concentration of between 10% and 90% of its initial concentration optionally, an antacid component to assist in the neutralisation of stomach acid optionally, a flavouring such as a sweetener to make the mixture more palatable In detail, a typical formulation contains:

ovine antibodies to Toxin A and/or B at 5-50 mg/ml ovine antibodies to binary toxin at 5-50 mg/ml a colostrum component has a final concentration of between 10% and 90% of its initial concentration optionally, an antacid component (e.g. magnesium hydroxide or sodium bicarbonate) at, for example, a concentration of 0.05 to 0.5 M optionally, a flavouring agent (e.g. a sweetener) such as vanilla essence

Example 17

Preparation of Antibodies Modified with Polyethylene Glycol or Dextran

Molecules of polyethylene glycol (PEG) or dextran are attached to the antibody in a variety of ways, which may be used singularly or in combination.

N-hydroxysuccinimide PEG derivatives allow attachment to ovine IgG via amino groups. For these reactions, freshly prepared N-hydroxysuccinimide PEG in aqueous buffer (e.g. HEPES 50 mM, between pH6.5 and 8.0) is mixed with IgG solution (5-100 mg/ml for up to 3 h at 37° C. or 24 h at 4° C.

Carboxyl PEGylation: After being activated by EDEC (N-(3-dimethylaminopropyl)-N'-ethylcarbodiimide, HCl salt) at mild acidic pH, the carboxyl group of antibodies readily react with PEG-hydrazide, while the amino groups present in all reagents remain inactive under these particular conditions.

Via carbohydrate (PEG hydrazide to react with aldehyde groups formed by periodate oxidation of oligosaccharide residues to form a hydrazone.

Using the above coupling methods PEG of various molecular weights (500-40000 Da) is coupled to IgG in a ratio of 2-20 PEG molecules per antibody molecule.

Dextrans offer an alternative to PEG as a derivatising agent and they are available in a range of molecular sizes (500-40000 Da) which can be covalently attached to IgG in a ratio of 2-20 dextran molecules per antibody molecule using sodium periodate creating polyaldehyde derivatives of the dextran. Unlike PEG chemistry, each dextran moiety can attach at more than one site on the antibody. A very similar strategy for modification with dextran can be used as described for PEGylation above and these are described by Hermanson (Hernamson, G T (1996) Bioconjugate Techniques, Academic Press)

The biological activity of pegylated or dextran-derivatised IgG preparations is measured by their capacity to neutralise either Toxin A, B or binary toxin in cell assays as described in Example 8. The stability of the pegylated or dextran-derivatised IgG is be assessed using simulated gastric and intestinal conditions as described in Example 21. These assessments, combined with in vivo efficacy studies, are used to optimise the above pegylation conditions to provide an IgG formulation with the desired stability to the digestive environment.

Retention of biological activity (toxin-neutralising activity) of the antibodies will be a trade off against their protection from the digestive environment. Pegylation or dextan derivatisation conditions preferably result in the highest overall delivery of active IgG to the gut.

Example 18

Coating of Antibodies with Copolymers of Methyl Acrylate, Methyl Methacrylate and Methacrylic Acid (Eudragit)

In one method to formulate ovine antibodies for oral delivery, antibodies are first made into small granules by mixing with corn starch powder. In this method, purified ovine IgG is mixed with corn starch in the ratio of approximately 1 part IgG to 4 parts starch. This mixture is then granulated in granulator (e.g. Yokomizo Granular model FR160×60) at a temperature between 20-37° C., humidity between 60-90% for between 2-15 min in order to produce granules of between 1-4 mm in diameter. In stage two of the process, the IgG granules are sealed by immersing in PEG aqueous solution (3-10%) of PEG (which is chosen from the molecular weight range 3000-10000) and then air drying at 37° C. In the final stage of the process, the sealed IgG granules are coated with a solution of Eudragit (e.g. Eudragit L100-55; Rohm GmbH, Germany). For this, an aqueous solution of Eudragit L100-55 (between 10-20%) is made by slowly adding the polymer to water and adding NaOH to partially neutralise 5-15% of the carboxyl groups. The PEG coated IgG granules are then coated in polymer solution by repeated immersion and air drying at 37° C. to give a final polymer coating of between 5-40% (w/w).

The stability of the coated IgG is assessed using simulated gastric and intestinal conditions as described in Example 21. These assessments, combined with in vivo efficacy studies, can be used to optimise the above coatings conditions to provide an IgG formulation with the desired stability to the digestive environment.

Example 19

Coating of Antibodies with Copolymers of Alginate/Chitosan

Alginate/chitosan microcapsules are prepared by methods similar to that described by Esquisabel et al. (J. Microencapsul, 14:627-638; 1997), which is incorporated in its entirety by reference. In this method 2% (w/v) alginate containing 0.2% (w/v) calcium chloride in water is added to purified ovine IgG (final concentration 0.1-20 mg/ml). After mixing, this aqueous phase is mixed with an oil phase (e.g. soybean oil containing 0.2% Tween 80) in a ratio of 1 part aqueous to 10 parts oil and emulsified for 5-10 min. After adjusting the pH to approx pH 5, the mixture is agitated for 15 min until the gelation reaction is complete. To this suspension, a water/n-hexane (80:20) mixture is added and the antibody microcapsules allowed to partition into the aqueous phase. This aqueous phase is separated and added to a chitosan solution 0.1 to 10% (w/v) in 1% catic acid solution in various proportions and allowed to react for 30 min before being filtered and dried.

The stability of the coated IgG is then assessed using simulated gastric and intestinal conditions as described in Example 21. These assessments, combined with in vivo efficacy studies, are used to optimise the above coatings conditions to provide an IgG formulation with the desired stability to the digestive environment.

Example 20

Coating of Antibodies with Pectin

Pectin beads are formed as described by Munjeri et al. (Drug Delivery 5: 239-241; 1998). Solutions (4% w/v) of amidated low methoxyl pectin in water are prepared by high speed mixing. Amidated pectin-antibody beads are prepared by combining the pectin and antibody in various ratios from 200:1 to 10:1 (pectin to antibody) and adding the solution drop-wise to a solution of calcium chloride (approx 2% w/v). The solution is pumped through tubes of diameter ranging from 1-5 mm and the resulting beads air dried and stored at 4° C.

Example 21

Assessing the Stability of Antibody Formulations to Digestive Enzymes Using Simulated Gastric and Intestinal Conditions Formulations are assessed for gastric stability by exposure to simulated gastric conditions. These are prepared as described in the United Stated Pharmacopeia (United Stated Pharmacopeial Convention Council of Experts (2004) 27, volume 22 p 2728), which is incorporated in its entirety, and consist of 3.2 mg/ml pepsin in 30 mM NaCl at pH 1.2. Antibody formulation is mixed with this solution in the ratio of 1 part pepsin solution to 250 parts antibody solution and incubated for various times (e.g. 0-360 min) at 37° C. At the end of the this time the integrity of the antibody is assessed for Toxin NB neutralising efficacy as described in Example 8. The degradation of the 150 kDa antibody molecule is also assessed on SDS PAGE gels on which the amount of the intact 150 kDa can be qualified relative to untreated control samples.

Formulations are assessed for intestinal stability by exposure to simulated intestinal conditions. These are prepared as described in the United Stated Pharmacopeia (United Stated Pharmacopeial Convention Council of Experts (2004) 27, volume 22 p 2728), which is incorporated in its entirety, and consist of 10 mg/ml pancreatin in 50 mM potassium phosphate buffer at pH 6.8 Antibody formulation is mixed with this solution in the ratio of 1 part pancreatin solution to 50 parts antibody solution and incubated for various times (e.g. 0-360 min) at 37° C. At the end of the this time the integrity of the antibody is be assessed for Toxin NB neutralising efficacy as described in Example 8. The degradation of the 150 kDa antibody molecule is also be assessed on SDS PAGE gels on which the amount of the intact 150 kDa is qualified relative to untreated control samples.

A combination of the above simulated gastric and intestinal conditions is also used to assess the stability of antibody formulations. In this case, after treatment with the pepsin solution the pH of the mixture is raised to 6.8 by adding e.g. 0.1 M sodium bicarbonate solution or 0.1M Tris-HCl before adding the pancreatin solution as described above.

Example 22

Assessment of the In Vivo Efficacy of Ovine Antibodies for Preventing CDI

To demonstrate the efficacy of antibodies to prevent CDI in vivo, Syrian hamsters are given an antibody formulation orally. For assessing the efficacy of a prophylactic formulation, hamsters are given antibody orally (up to 0.5 ml) at various times from 96 hours pre-challenge to 240 hours post challenge with *C. difficile*

During the administration of formulation, CDI is induced in hamsters by giving a broad spectrum antibiotic (e.g. clindamycin) and then 12-72 h later by challenge with *C. difficile* spores by mouth. Animals are then monitored for up to 15 days for symptoms of *C. difficile*-associated disease. Control, untreated animals develop signs of the disease (e.g. diarrhoea, swollen abdomen, lethargy, ruffled fur) while those treated with ovine antibody formulation either appear normal or develop only mild disease symptoms.

Example 23

Assessment of the In Vivo Efficacy of Ovine Antiserum for Treating CDI

To demonstrate the efficacy of antibodies to treat CDI in vivo, Syrian hamsters are given antibody formulation (as described in Example 15 and 16) orally. For assessing the efficacy of a treatment formulation, hamsters will be given antibody orally (up to 0.5 ml) at various times from 6 hours post-challenge to 240 hours post challenge with *C. difficile*.

Prior to the administration of formulation, CDI is induced in hamsters by giving a broad spectrum antibiotic (e.g. clindamycin) and then 12-72 h later by challenge with *C. difficile* spores by mouth. Animals are then monitored for up to 15 days for symptoms of *C. difficile*-associated disease. Control, untreated animals develop signs of the disease (e.g. diarrhoea, swollen abdomen, lethargy, ruffled fur) while those treated with ovine antibody formulation either appear normal or develop only mild disease symptoms.

In Vivo Experiment 1—Oral Delivery of an Antibody in the Presence of an Antacid

Aim:

To assess the efficacy of an orally administered mixture of ovine antibodies to Toxins A and B to protect from CDI induced by challenge with *C. difficile* spores (strain VPI 10463). Two different dose levels were assessed which were given once on day 0 and then 2 times daily over 4 days Methodology Three groups of animals were used:

Group 1 and 2—which were divided 'Test Sub-Group' of 10 animals and a 'Control Sub-Group' of 4 animals (which did not receive a spore challenge).

Group 3—'Test Sub-Group' of 10 animals

Group 1—Test and control groups received PBS containing 0.1M sodium bicarbonate (The sodium bicarbonate was added to 0.1M immediately before dosing)

Group 2—Test and control groups received ovine antibody A+B mixture in a 1:1 ratio containing 0.1M sodium bicarbonate (Sodium bicarbonate was added to 0.1M immediately before dosing). Ovine anti-Toxin A—batch CDA000185 and ovine anti-Toxin B—batch CDB000229 were used in a 1:1 ratio. Final antibody concentration was 45 mg per ml for the mixture. Hamsters received 45 mg antibody per day.

Group 3—Test and control groups received ovine antibody A+B mixture in a 1:1 ratio containing 0.1M sodium bicarbonate (Sodium bicarbonate was added to 0.1M immediately before dosing). Ovine anti-Toxin A—batch CDA000185 and ovine anti-Toxin B—batch CDB000229 were used in a 1:1 ratio and diluted 5-fold with PBS. Final antibody concentration was 9 mg per ml for the mixture. Hamsters received 9 mg antibody per day Clindamycin (0.2 ml of 10 mg/ml solution) and *C. difficile* VPI 10463 spores (250 cfu in a 0.2 ml dose) were given orogastrically.

Dosing Timetable for In Vivo Experiment 1 (all Doses Given Orogastrically)

| Day (from challenge) | AM (9-10 am) | PM (3-4 pm) |
|---|---|---|
| Day −3 | Clindamycin | — |
| Day 0 | Spore challenge | 0.5 ml Antibody (or PBS) |
| Day 1 | 0.5 ml Antibody (or PBS) | 0.5 ml Antibody (or PBS) |
| Day 2 | 0.5 ml Antibody (or PBS) | 0.5 ml Antibody (or PBS) |
| Day 3 | 0.5 ml Antibody (or PBS) | 0.5 ml Antibody (or PBS) |
| Day 4 | 0.5 ml Antibody (or PBS) | 0.5 ml Antibody (or PBS) |

Results & Conclusions

Survival data are shown in FIG. 5. The control Group showed rapid onset of severe CDI with all animals succumbing to severe disease within 3 days post challenge.

The orally administered antibody mixture offered protection from rate of disease onset. On Day 4 post challenge, while a 100% of animal had succumbed to disease in the PBS control (Group 1), 30% and 60% were surviving in the low (Group 3) and high (Group 2) antibody dose groups, respectively.

At the termination of experiment 20% of animal survived in both antibody groups compared to 0% in the PBS control group. Orally administered antibody in the presence of an antacid doses administered offer some protection against the onset of CDI In Vivo Experiment 2—Oral Delivery of a High Antibody Dose in the Presence of an Antacid Aim:

To assess the efficacy of an orally administered mixture of ovine antibodies to Toxins A and B to protect from CDI induced by challenge with *C. difficile* spores (strain VPI 10463). The antibody was given once on day 0 and then 3 times daily over 4 days.

Methodology

Two groups of animals were used:

Group 1—was divided 'Test Sub-Group' of 10 animals and a 'Control Sub-Group' of 4 animals (which did not receive a spore challenge).

Group 2—'Test Group' of 10 animals

Group 1—Test and control sub-groups received no treatment

Group 2—Test group received ovine antibody A+B mixture in a 1:1 ratio containing 0.1M sodium bicarbonate. (Sodium bicarbonate was added to 0.1M immediately before dosing). Ovine anti-Toxin A—batch CDA000264 and ovine anti-Toxin B—batch CDB000229 were used in a 1:1 ratio. Final antibody concentration was 45 mg per ml for the mixture. Hamsters received 68 mg antibody per day Clindamycin (0.2 ml of 10 mg/ml solution) and *C. difficile* VPI 10463 spores (500 cfu in a 0.2 ml dose) were given orogastrically.

Results & Conclusions

The survival data are shown in FIG. 6. The control animals (Group 1) showed a relatively slow onset of severe CDI with 60% of animals succumbing to severe disease within 9 days post challenge. Group 2 animals treated with buffered liquid antibody (68 mg total per day) showed no symptoms of CDI over a 16 day period of the experiment and were completely protected. One animal succumbed to disease on Day 17. Overall, there was significant protection from CDI of animals in Group 2 compared to the control group (Group 1).

The data show that orally administered ovine antibody can both prevent and treat CDI.

Dosing Timetable for In Vivo Experiment 2 (All Doses Given Orogastrically)

| Day (from challenge) | AM (9-10 am) | Midday | PM (3-4 pm) |
|---|---|---|---|
| Day −3 | Clindamycin (Gp1 and 2) | — | — |
| Day 0 | Spore challenge (Gp1 and 2) | — | 0.5 ml Antibody (Gp2) |
| Day 1 | 0.5 ml Antibody (Gp2) | 0.5 ml Antibody (Gp2) | 0.5 ml Antibody (Gp2) |
| Day 2 | 0.5 ml Antibody (Gp2) | 0.5 ml Antibody (Gp2) | 0.5 ml Antibody (Gp2) |
| Day 3 | 0.5 ml Antibody (Gp2) | 0.5 ml Antibody (Gp2) | 0.5 ml Antibody (Gp2) |
| Day 4 | 0.5 ml Antibody (Gp2) | 0.5 ml Antibody (Gp2) | 0.5 ml Antibody (Gp2) |

In Vivo Experiment 3—Oral Delivery of Antibody in the from of Enteric-Coated Capsules Aim:

To assess the efficacy of an orally administered mixture of ovine antibodies to Toxins A and B in an encapsulated form to protect from CDI induced by challenge with *C. difficile* spores (strain VPI 10463).

Methodology

Two groups of animals were used:

Group 1—was divided 'Test Sub-Group' of 10 animals and a 'Control Sub-Group' of 4 animals (which did not receive a spore challenge). Group 2—'Test Group' of 10 animals Group 1—Test and control groups received no treatment Group 2—Test groups received enteric-coate capsules (Encap: Batch 244/15/1). Capsules received 2 enteric coats (Eudragit+PEG400) to maintain their integrity through the stomach and small intestine, These contained approximately 10 µl of a mixture of ovine anti-Toxin A—batch CDA000264 and ovine anti-Toxin B—batch CDB000229 in a 1:1 ratio. Hamsters received approximately 1.5 mg of the antibody mixture per day Results & Conclusions The survival data are shown in FIG. 7. Group 2 animals were given a small dose of antibody in capsule form (approx 1.5 mg per day). Some protection from this antibody dose was observed. On Day 5 post challenge, while 40% of the Group 1 control animals had succumbed to severe disease, 90% were surviving in Group 2. At the end of the experiment 60% of the Group 2 capsule-treated animal survived compared to 40% in the Group 1 controls.

Dosing Timetable for In Vivo Experiment 3 (All Doses Given Orogastrically)

| Day (from challenge) | AM (9-10 am) | Midday | PM (3-4 pm) |
|---|---|---|---|
| Day −3 | Clindamycin (Gp1 and 2) | — | — |
| Day 0 | Spore challenge (Gp1 and 2) | — | 1 × capsule (Gp2) |
| Day 1 | 1 × capsule (Gp2) | 1 × capsule (Gp2) | 1 × capsule (Gp2) |
| Day 2 | 1 × capsule (Gp3) | 1 × capsule (Gp2) | 1 × capsule (Gp2) |
| Day 3 | 1 × capsule (Gp3) | 1 × capsule (Gp2) | 1 × capsule (Gp2) |
| Day 4 | 1 × capsule (Gp3) | 1 × capsule (Gp2) | 1 × capsule (Gp2) |

Example 24

Clinical Uses of Antibody Formulations (Drug Substance)

Prophylactic Treatment of 'At Risk' Patient Groups

As a prophylactic for CDI, patients identified as 'at risk' will the treated with the drug substance. Parameters for defining such groups of patients include:
- hospitalised
- over 65 yr
- receiving broad-spectrum antibiotics
- previous history of CDI or close proximity to symptomatic cases Patients groups which are particularly appropriate for oral antibody therapy include:
- those with mild to moderate disease severity
- those who are asymptomatic but are considered at high risk of relapse (perhaps because of one or more relapse episodes)
- those in close proximity to outbreak cases Patients falling into this category will be administered orally, formulations of the drug substance 10-50 ml up to 6 times daily over a period of up to 2 weeks. None of the patient will develop symptoms of CDI whilst being treated.

Example 25

Clinical Use of a Combination of Orally Delivered Antibody and Antibiotics

The oral administration of antibodies to treat CDI is performed in conjunction with standard antibiotic therapy as detailed in the example below.

A patient with recurrent *Clostridium difficile* infections, Mrs CL, develops diarrhoea while in a residential care home following a course of antibiotics prescribed to treat a urinary tract infection. Some days later she develops watery diarrhoea and is transferred to hospital where Toxin A and Toxin B are detected in a stool sample. The 84 year old patient is given a course of metronidazole and appears to make a full recovery. However a few days later her diarrhoea reoccurs and, again, CDI is diagnosed by the appropriate procedure. A course of vancomycin results in a transient cessation of her diarrhoea but, within days, her CDI recurrent for a third time. Finally, a complete cure is obtained by a combination of a tapering dose of vancomycin followed by a four week course of the orally administered ovine polyclonal antibodies (500 mg bd).

Example 26

Clinical Uses of a Combination of Systemically and Orally Delivered Antibody Formulations Where patients suffer severe CDI, which can result in bowel obstruction, a combination of systemically and orally delivered antibody is employed. An example of such usage is given below.

A patient with a refractory *Clostridium difficile* infection, Mrs MN, a 72 years old pensioner, is admitted to hospital following a mild stroke. She is making an uneventful recovery when she develops a chest infection requiring antibiotics. Ten days later she experiences severe diarrhoea associated with mild abdominal pain. Both Toxin A and Toxin B are detected in a stool samples from which *C. difficile* is cultured and subsequently and shown to be ribotype 027. Immediately her *C. difficile* infection (CDI) is diagnosed, Mrs MN is given a course of metronidazole. However, although her symptoms improve, she continues to pass watery stools. A course of vancomycin also fails to resolve completely her CDI. *C. difficile* toxins are still present in her faeces so she receives three intravenous injections of ovine anti-*C. difficile* toxin antibodies (250 mg on alternate days). In combination, she receives orally (via a three week course) ovine antibodies (500 mg bd) as an outpatient, and makes a full recovery.

SEQ ID NOs

*Clostridium difficile* Toxin A - Toxinotype 0

SEQ ID NO: 1

```
MSLISKEELIKLAYSIRPRENEYKTILTNLDEYNKLTTNNNENKYLQLKKLNESIDVFMNKYKTS
SRNRALSNLKKDILKEVILIKNSNTSPVEKNLHFVWIGGEVSDIALEYIKQWADINAEYNIKLWY
DSEAFLVNTLKKAIVESSTTEALQLLEEEIQNPQFDNMKFYKKRMEFIYDRQKRFINYYKSQIN
KPTVPTIDDIIKSHLVSEYNRDETVLESYRTNSLRKINSNHGIDIRANSLFTEQELLNIYSQELLN
RGNLAAASDIVRLLALKNFGGVYLDVDMLPGIHSDLFKTISRPSSIGLDRWEMIKLEAIMKYKK
YINNYTSENFDKLDQQLKDNFKLIIESKSEKSEIFSKLENLNVSDLEIKIAFALGSVINQALISKQ
GSYLTNLVIEQVKNRYQFLNQHLNPAIESDNNFTDTTKIFHDSLFNSATAENSMFLTKIAPYLQ
VGFMPEARSTISLSGPGAYASAYYDFINLQENTIEKTLKASDLIEFKFPENNLSQLTEQEINSL
WSFDQASAKYQFEKYVRDYTGGSLSEDNGVDFNKNTALDKNYLLNNKIPSNNVEEAGSKNY
VHYIIQLQGDDISYEATCNLFSKNPKNSIIIQRNMNESAKSYFLSDDGESILELNKYRIPERLKN
KEKVKVTFIGHGKDEFNTSEFARLSVDSLSNEISSFLDTIKLDISPKNVEVNLLGCNMFSYDFN
VEETYPGKLLLSIMDKITSTLPDVNKNSITIGANQYEVRINSEGRKELLAHSGKWINKEEAIMSD
LSSKEYIFFDSIDNKLKAKSKNIPGLASISEDIKTLLLDASVSPDTKFILNNLKLNIESSIGDYIYYE
KLEPVKNIIHNSIDDLIDEFNLLENVSDELYELKKLNNLDEKYLISFEDISKNNSTYSVRFINKSN
GESVYVETEKEIFSKYSEHITKEISTIKNSIITDVNGNLLDNIQLDHTSQVNTLNAAFFIQSLIDYS
SNKDVLNDLSTSVKVQLYAQLFSTGLNTIYDSIQLVNLISNAVNDTINVLPTITEGIPIVSTILDGI
NLGAAIKELLDEHDPLLKKELEAKVGVLAINMSLSIAATVASIVGIGAEVTIFLLPIAGISAGIPSL
VNNELILHDKATSVVNYFNHLSESKKYGPLKTEDDKILVPIDDLVISEIDFNNNSIKLGTCNILAM
EGGSGHTVTGNIDHFFSSPSISSHIPSLSIYSAIGIETENLDFSKKIMMLPNAPSRVFWWETGA
VPGLRSLENDGTRLLDSIRDLYPGKFYWRFYAFFDYAITTLKPVYEDTNIKIKLDKDTRNFIMP
TITTNEIRNKLSYSFDGAGGTYSLLLSSYPISTNINLSKDDLWIFNIDNEVREISIENGTIKKGKLI
KDVLSKIDINKNKLIIGNQTIDFSGDIDNKDRYIFLTCELDDKISLIIEINLVAKSYSLLLSGDKNYLI
SNLSNTIEKINTLGLDSKNIAYNYTDESNNKYFGAISKTSQKSIIHYKKDSKNILEFYNDSTLEFN
SKDFIAEDINVFMKDDINTITGKYYVDNNTDKSIDFSISLVSKNQVKVNGLYLNESVYSSYLDFV
KNSDGHHNTSNFMNLFLDNISFWKLFGFENINFVIDKYFTLVGKTNLGYVEFICDNNKNIDIYF
GEWKTSSSKSTIFSGNGRNVVVEPIYNPDTGEDISTSLDFSYEPLYGIDRYINKVLIAPDLYTSL
ININTNYYSNEYYPEIIVLNPNTFHKKVNINLDSSSFEYKWSTEGSDFILVRYLEESNKKILQKIR
IKGILSNTQSFNKMSIDFKDIKKLSLGYIMSNFKSFNSENELDRDHLGFKIIDNKTYYYDEDSKL
VKGLININNSLFYFDPIEFNLVTGWQTINGKKYYFDINTGAALTSYKIINGKHFYFNNDGVMQL
GVFKGPDGFEYFAPANTQNNNIEGQAIVYQSKFLTLNGKKYYFDNNSKAVTGWRIINNEKYY
FNPNNAIAAVGLQVIDNNKYYFNPDTAIISKGWQTVNGSRYYFDTDTAIAFNGYKTIDGKHFYF
DSDCVVKIGVFSTSNGFEYFAPANTYNNNIEGQAIVYQSKFLTLNGKKYYFDNNSKAVTGLQT
IDSKKYYFNTNTAEAATGWQTIDGKKYYFNTNTAEAATGWQTIDGKKYYFNTNTAIASTGYTII
NGKHFYFNTDGIMQIGVFKGPNGFEYFAPANTDANNIEGQAILYQNEFLTLNGKKYYFGSDS
KAVTGWRIINNKKYYFNPNNAIAAIHLCTINNDKYYFSYDGILQNGYITIERNNFYFDANNESK
MVTGVFKGPNGFEYFAPANTHNNNIEGQAIVYQNKFLTLNGKKYYFDNDSKAVTGWQTIDG
KKYYFNLNTAEAATGWQTIDGKKYYFNLNTAEAATGWQTIDGKKYYFNTNTFIASTGYTSING
KHFYFNTDGIMQIGVFKGPNGFEYFAPANTDANNIEGQAILYQNKFLTLNGKKYYFGSDSKAV
TGLRTIDGKKYYFNTNTAVAVTGWQTINGKKYYFNTNTSIASTGYTIISGKHFYFNTDGIMQIG
VFKGPDGFEYFAPANTDANNIEGQAIRYQNRFLYLHDNIYYFGNNSKAATGWVTIDGNRYYF
EPNTAMGANGYKTIDNKNFYFRNGLPQIGVFKGSNGFEYFAPANTDANNIEGQAIRYQNRFL
HLLGKIYYFGNNSKAVTGWQTINGKVYYFMPDTAMAAAGGLFEIDGVIYFFGVDGVKAPGIY
G
```

Protein Sequence of *C. difficile* Toxin B - Toxinotype 0

SEQ ID NO: 2

```
MSLVNRKQLEKMANVRFRTQEDEYVAILDALEEYHNMSENTVVEKYLKLKDINSLTDIYIDTY
KKSGRNKALKKFKEYLVTEVLELKNNNLTPVEKNLHFVWIGGQINDTAINYINQWKDVNSDYN
VNVFYDSNAFLINTLKKTVVESAINDTLESFRENLNDPRFDYNKFFRKRMEIIYDKQKNFINYY
KAQREENPELIIDDIVKTYLSNEYSKEIDELNTYIEESLNKITQNSGNDVRNFEEFKNGESFNLY
EQELVERWNLAAASDILRISALKEIGGMYLDVDMLPGIQPDLFESIEKPSSVTVDFWEMTKLE
AIMKYKEYIPEYTSEHFDMLDEEVQSSFESVLASKSDKSEIFSSLGDMEASPLEVKIAFNSKGII
NQGLISVKDSYCSNLIVKQIENRYKILNNSLNPAISEDNDFNTTTNTFIDSIMAEANADNGRFM
MELGKYLRVGFFPDVKTTINLSGPEAYAAAYQDLLMFKEGSMNIHLIEADLRNFEISKTNISQS
TEQEMASLWSFDDARAKAQFEEYKRNYFEGSLGEDDNLDFSQNIVVDKEYLLEKISSLARSS
ERGYIHYIVQLQGDKISYEAACNLFAKTPYDSVLFQKNIEDSEIAYYYNPGDGEIQEIDKYKIPSI
ISDRPKIKLTFIGHGKDEFNTDIFAGFDVDSLSTEIEAAIDLAKEDISPKSIEINLLGCNMFSYSIN
VEETYPGKLLLKVKDKISELMPSISQDSIIVSANQYEVRINSEGRRELLDHSGEWINKEESIIKDI
SSKEYISFNPKENKITVKSKNLPELSTLLQEIRNNSNSSDIELEEKVMLTECEINVISNIDTQIVE
ERIEEAKNLTSDSINYIKDEFKLIESISDALCDLKQQNELEDSHFISFEDISETDEGFSIRFINKET
GESIFVETEKTIFSEYANHITEEISKIKGTIFDTVNGKLVKKVNLDTTHEVNTLNAAFFIQSLIEYN
SSKESLSNLSVAMKVQVYAQLFSTGLNTITDAAKVVELVSTALDETIDLLPTLSEGLPIIATIIDG
VSLGAAIKELSETSDPLLRQEIEAKIGIMAVNLTTATTAIITSSLGIASGFSILLVPLAGISAGIPSL
VNNELVLRDKATKVVDYFKHVSLVETEGVFTLLDDKIMMPQDDLVISEIDFNNNSIVLGKCEIW
RMEGGSGHTVTDDIDHFFSAPSITYREPHLSIYDVLEVQKEELDLSKDLMVLPNAPNRVFAW
ETGWTPGLRSLENDGTKLLDRIRDNYEGEFYWRYFAFIADALITTLKPRYEDTNIRINLDSNTR
SFIVPIITTEYIREKLSYSFYGSGGTYALSLSQYNMGINIELSESDVWIIDVDNVVRDVTIESDKI
KKGDLIEGILSTLSIEENKIILNSHEINFSGEVNGSNGFVSLTFSILEGINAIIEVDLLSKSYKLLIS
GELKILMLNSNHIQQKIDYIGFNSELQKNIPYSFVDSEGKENGFINGSTKEGLFVSELPDVVLIS
KVYMDDSKPSFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANFIISGTTSIGQFEFICD
```

| SEQ ID NOs |
|---|

ENDNIQPYFIKFNTLETNYTLYVGNRQNMIVEPNYDLDDSGDISSTVINFSQKYLYGIDSCVNK
VVISPNIYTDEINITPVYETNNTYPEVIVLDANYINEKINVNINDLSIRYVWSNDGNDFILMSTSE
ENKVSQVKIRFVNVFKDKTLANKLSFNFSDKQDVPVSEIILSFTPSYYEDGLIGYDLGLVSLYN
EKFYINNFGMMVSGLIYINDSLYYFKPPVNNLITGFVTVGDDKYYFNPINGGAASIGETIIDDKN
YYFNQSGVLQTGVFSTEDGFKYFAPANTLDENLEGEAIDFTGKLIIDENIYYFDDNYRGAVEW
KELDGEMHYFSPETGKAFKGLNQIGDYKYYFNSDGVMQKGFVSINDNKHYFDDSGVMKVG
YTEIDGKHFYFAENGEMQIGVFNTEDGFKYFAHHNEDLGNEEGEEISYSGILNFNNKIYYFDD
SFTAVVGWKDLEDGSKYYFDEDTAEAYIGLSLINDGQYYFNDDGIMQVGFVTINDKVFYFSD
SGIIESGVQNIDDNYFYIDDNGIVQIGVFDTSDGYKYFAPANTVNDNIYGQAVEYSGLVRVGE
DVYYFGETYTIETGWIYDMENESDKYYFNPETKKACKGINLIDDIKYYFDEKGIMRTGLISFEN
NNYYFNENGEMQFGYINIEDKMFYFGEDGVMQIGVFNTPDGFKYFAHQNTLDENFEGESINY
TGWLDLDEKRYYFTDEYIAATGSVIIDGEEYYFDPDTAQLVISE

Protein Sequence of *C. difficile* Toxin A - Toxinotype III
SEQ ID NO: 3
MSLISKEELIKLAYSIRPRENEYKTILTNLDEYNKLTTNNNENKYLQLKKLNESIDVFMNKYKNS
SRNRALSNLKKDILKEVILIKNSNTSPVEKNLHFVWIGGEVSDIALEYIKQWADINAEYNIKLWY
DSEAFLVNTLKKAIVESSTTEALQLLEEEIQNPQFDNMKFYKKRMEFIYDRQKRFINYYKSQIN
KPTVPTIDDIIKSHLVSEYNRDETLLESYRTNSLRKINSNHGIDIRANSLFTEQELLNIYSQELLN
RGNLAAASDIVRLLALKNFGGVYLDVDMLPGIHSDLFKTIPRPSSIGLDRWEMIKLEAIMKYKK
YINNYTSENFDKLDQQLKDNFKLIIESKSEKSEIFSKLENLNVSDLEIKIAFALGSVINQALISKQ
GSYLTNLVIEQVKNRYQFLNQHLNPAIESDNNFTDTTKIFHDSLFNSATAENSMFLTKIAPYLQ
VGFMPEARSTISLSGPGAYASAYYDFINLQENTIEKTLKASDLIEFKFPENNLSQLTEQEINSL
WSFDQASAKYQFEKYVRDYTGGSLSEDNGVDFNKNTALDKNYLLNNKIPSNNVEEAGSKNY
VHYIIQLQGDDISYEATCNLFSKNPKNSIIIQRNMNESAKSYFLSDDGESILELNKYRIPERLKN
KEKVKVTFIGHGKDEFNTSEFARLSVDSLSNEISSFLDTIKLDISPKNVEVNLLGCNMFSYDFN
VEETYPGKLLLSIMDKITSTLPDVNKDSITIGANQYEVRINSEGRKELLAHSGKWINKEEAIMSD
LSSKEYIFFDSIDNKLKAKSKNIPGLASISEDIKTLLLDASVSPDTKFILNNLKLNIESSIGDYIYYE
KLEPVKNIIHNSIDDLIDEFNLLENVSDELYELKKLNNLDEKYLISFEDISKNNSTYSVRFINKSN
GESVYVETEKEIFSKYSEHITKEISTIKNSIITDVNGNLLDNIQLDHTSQVNTLNAAFFIQSLIDYS
SNKDVLNDLSTSVKVQLYAQLFSTGLNTIYDSIQLVNLISNAVNDTINVLPTITEGIPIVSTILDGI
NLGAAIKELLDEHDPLLKKELEAKVGVLAINMSLSIAATVASIVGIGAEVTIFLLPIAGISAGIPSL
VNNELILHDKATSVVNYFNHLSESKEYGPLKTEDDKILVPIDDLVISEIDFNNNSIKLGTCNILAM
EGGSGHTVTGNIDHFFSSPYISSHIPSLSVYSAIGIKTENLDFSKKIMMLPNAPSRVFWWETG
AVPGLRSLENNGTKLLDSIRDLYPGKFYWRFYAFFDYAITTLKPVYEDTNTKIKLDKDTRNFIM
PTITTDEIRNKLSYSFDGAGGTYSLLLSSYPISMNINLSKDDLWIFNIDNEVREISIENGTIKKGN
LIEDVLSKIDINKNKLIIGNQTIDFSGDIDNKDRYIFLTCELDDKISLIIEINLVAKSYSLLLSGDKNY
LISNLSNTIEKINTLGLDSKNIAYNYTDESNNKYFGAISKTSQKSIIHYKKDSKNILEFYNGSTLE
FNSKDFIAEDINVFMKDDINTITGKYYVDNNTDKSIDFSISLVSKNQVKVNGLYLNESVYSSYL
DPVKNSDGHHNTSNFMNLFLNNISFWKLFGFENINFVIDKYFTLVGKTNLGYVEFICDNNKNID
IYFGEWKTSSSKSTIFSGNGRNVVVEPIYNPDTGEDISTSLDFSYEPLYGIDRYINKVLIAPDLY
TSLININTNYYSNEYYPEIIVLNPNTPHKKVNINLDSSSFEYKWSTEGSDFILVRYLEESNKKILQ
KIRIKGILSNTQSFNKMSIDFKDIKKLSLGYIMSNFKSFNSENELDRDHLGFKIIDNKTYYYDED
SKLVKGLININNSLFYFDPIESNLVTGWQTINGKKYYFDINTGAASTSYKIINGKHFYFNNNGV
MQLGVFKGPDGFEYFAPANTQNNNIEGQAIVYQSKFLTLNGKKYYFDNDSKAVTGWRIINNE
KYYFNPNNAIAAVGLQVIDNNKYYFNPDTAIISKGWQTVNGSRYYFDTDTAIAFNGYKTIDGK
HFYFDSDCVVKIGVFSGSNGFEYFAPANTYNNNIEGQAIVYQSKFLTLNGKKYYFDNNSKAV
TGWQTIDSKKYYFNTNTAEAATGWQTIDGKKYYFNTNTAEAATGWQTIDGKKYYFNTNTSIA
STGYTIINGKYFYFNTDGIMQIGVFKVPNGFEYFAPANTHNNNIEGQAILYQNKFLTLNGKKYY
FGSDSKAITGWQTIDGKKYYFNPNNAIAATHLCTINNDKYYFSYDGILQNGYITIERNNFYFDA
NNESKMVTGVFKGPNGFEYFAPANTHNNNIEGQAIVYQNKFLTLNGKKYYFDNDSKAVTGW
QTIDSKKYYFNLNTAVAVTGWQTIDGEKYYFNLNTAEAATGWQTIDGKRYYFNTNTYIASTGY
TIINGKHFYFNIDGIMQIGVFKGPDGFEYFAPANTHNNNIEGQAILYQNKFLTLNGKKYYFGSD
SKAVTGLRTIDGKKYYFNTNTAVAVTGWQTIDGKKYYFNTNTYIASTGYTIISGKHFYFNTDGI
MQIGVFKGPDGFEYFAPANTDANNIEGQAIRYQNRFLYLHDNIYYFGNDSKAATGWATIDGN
RYYFEPNTAMGANGYKTIDNKNFYFRNGLPQIGVFKPNGFEYFAPANTDANNIDGQAIRYQ
NRFLHLLGKIYYFGNNSKAVTGWQTINSKVYYFMPDTAMAAAGGLFEIDGVIYFFGVDGVKA
PGIYG Protein Sequence of *C. difficile* Toxin B - Toxinotype III
SEQ ID NO: 4
MSLVNRKQLEKMANVRFRVQEDEYVAILDALEEYHNMSENTVVEKYLKLKDINSLTDIYIDTY
KKSGRNKALKKFKEYLVTEVLELKNNNLTPVEKNLHFVWIGGQINDTAINYINQWKDVNSDYN
VNVFYDSNAFLINTLKKTIVESAINDTLESFRENLNDPRFDYNKFYRKRMEIIYDKQKNFINYY
KTQREENPDLIIDDIVKIYLSNEYSKDIDELNSYIEESLNKVTENSGNDVRNFEEFKGGESFKLY
EQELVERWNLAAASDILRISALKEVGGVYLDVDMLPGIQPDLFESIEKPSSVTVDFWEMVKLE
AIMKYKEYIPGYTSEHFDMLDEEVQSSFESVLASKSDKSEIFSSLGDMEASPLEVKIAFNSKGI
INQGLISVKDSYCSNLIVKQIENRYKILNNSLNPAISEDNDFNTTTNAFIDSIMAEANADNGRFM
MELGKYLRVGFFPDVKTTINLSGPEAYAAAYQDLLMFKEGSMNIHLIEADLRNFEISKTNISQS
TEQEMASLWSFDDARAKAQFEEYKKNYFEGSLGEDDNLDFSQNTVVDKEYLLEKISSLARS
SERGYIHYIVQLQGDKISYEAACNLFAKTPYDSVLFQKNIEDSEIAYYYNPGDGEIQEIDKYKIP
SIISDRPKIKLTFIGHGKDEFNTDIFAGLDVDSLSTEIETAIDLAKEDISPKSIEINLLGCNMFSYS
VNVEETYPGKLLLRVKDKVSELMPSISQDSIIVSANQYEVRINSEGRRELLDHSGEWINKEESI
IKDISSKEYISFNPKENKIIVKSKNLPELSTLLQEIRNNSNSSDIELEEKVMLAECEINVISNIDTQ
VVEGRIEEAKSLTSDSINYIKNEFKLIESISDALYDLKQQNELEESHFISFEDILETDEGFSIRFID
KETGESIFVETEKAIFSEYANHITEEISKIKGTIFDTVNGKLVKKVNLDATHEVNTLNAAFFIQSLI
EYNSSKESLSNLSVAMKVQVYAQLFSTGLNTITDAAKVVELVSTALDETIDLLPTLSEGLPVIA

| SEQ ID NOs |
|---|
| TIIDGVSLGAAIKELSETSDPLLRQEIEAKIGIMAVNLTAATTAIITSSLGIASGFSILLVPLAGISA<br>GIPSLVNNELILRDKATKVVDYFSHISLAESEGAFTSLDDKIMMPQDDLVISEIDFNNNSITLGK<br>CEIWRMEGGSGHTVTDDIDHFFSAPSITYREPHLSIYDVLEVQKEELDLSKDLMVLPNAPNRV<br>FAWETGWTPGLRSLENDGTKLLDRIRDNYEGEFYWRYFAFIADALITTLKPRYEDTNIRINLD<br>SNTRSFIVPVITTEYIREKLSYSFYGSGGTYALSLSQYNMNINIELNENDTWVIDVDNVVRDVTI<br>ESDKIKKGDLIENILSKLSIEDNKIILDNHEINFSGTLNGGNGFVSLTFSILEGINAVIEVDLLSKS<br>YKVLISGELKTLMANSNSVQQKIDYIGLNSELQKNIPYSFMDDKGKENGFINCSTKEGLFVSEL<br>SDVVLISKVYMDNSKPLFGYCSNDLKDVKVITKDDVIILTGYYLKDDIKISLSFTIQDENTIKLNG<br>VYLDENGVAEILKFMNKKGSTNTSDSLMSFLESMNIKSIFINSLQSNTKLILDTNFIISGTTSIGQ<br>FEFICDKDNNIQPYFIKFNTLETKYTLYVGNRQNMIVEPNYDLDDSGDISSTVINFSQKYLYGID<br>SCVNKVIISPNIYTDEINITPIYEANNTYPEVIVLDTNYISEKININNINDLSIRYVWSNDGSDFILMS<br>TDEENKVSQVKIRFTNVFKGNTISDKISFNFSDKQDVSINKVISTFTPSYYVEGLLNYDLGLISL<br>YNEKFYINNFGMMVSGLVYINDSLYYFKPPIKNLITGFTTIGDDKYYFNPDNGGAASVGETIID<br>GKNYYFSQNGVLQTGVFSTEDGFKYFAPADTLDENLEGEAIDFTGKLTIDENVYYFGDNYRA<br>AIEWQTLDDEVYYFSTDTGRAFKGLNQIGDDKFYFNSDGIMQKGFVNINDKTFYFDDSGVMK<br>SGYTEIDGKYFYFAENGEMQIGVFNTADGFKYFAHHDEDLGNEEGEALSYSGILNFNNKIYYF<br>DDSFTAVVGWKDLEDGSKYYFDEDTAEAYIGISIINDGKYYFNDSGIMQIGFVTINNEVFYFSD<br>SGIVESGMQNIDDNYFYIDENGLVQIGVFDTSDGYKYFAPANTVNDNIYGQAVEYSGLVRVG<br>EDVYYFGETYTIETGWIYDMENESDKYYFDPETKKAYKGINVIDDIKYYFDENGIMRTGLITFE<br>DNHYYFNEDGIMQYGYLNIEDKTFYFSEDGIMQIGVFNTPDGFKYFAHQNTLDENFEGESINY<br>TGWLDLDEKRYYFTDEYIAATGSVIIDGEEYYFDPDTAQLVISE |

Protein Sequence of *C. difficile* Binary toxin fragment A
SEQ ID NO: 5
MKKFRKHKRISNCISILLILYLTLGGLLPNNIYAQDLQSYSEKVCNTTYKAPIESFLKDKEKAKE
WERKEAERIEQKLERSEKEALESYKKDSVEISKYSQTRNYFYDYQIEANSREKEYKELRNAIS
KNKIDKPMYVYYFESPEKFAFNKVIRTENQNEISLEKFNEFKETIQNKLFKQDGFKDISLYEPG
KGDEKPTPLLMHLKLPRNTGMLPYTNTNNVSTLIEQGYSIKIDKIVRIVIDGKHYIKAEASVVNS
LDFKDDVSKGDSWGKANYNDWSNKLTPNELADVNDYMRGGYTAINNYLISNGPVNNPNPEL
DSKITNIENALKREPIPTNLTVYRRSGPQEFGLTLTSPEYDFNKLENIDAFKSKWEGQALSYPN
FISTSIGSVNMSAFAKRKIVLRITIPKGSPGAYLSAIPGYAGEYEVLLNHGSKFKINKIDSYKDGT
ITKLIVDATLIP Protein Sequence of *C. difficile* Binary toxin fragment B
SEQ ID NO: 6
MKIQMRNKKVLSFLTLTAIVSQALVYPVYAQTSTSNHSNKKKEIVNEDILPNNGLMGYYFSDE
HFKDLKLMAPIKDGNLKFEEKKVDKLLDKDKSDVKSIRWTGRIIPSKDGEYTLSTDRDDVLMQ
VNTESTISNTLKVNMKKGKEYKVRIELQDKNLGSIDNLSSPNLYWELDGMKKIIPEENLFLRDY
SNIEKDDPFIPNNNFFDPKLMSDWEDEDLDTNDNIPDSYERNGYTIKDLIAVKWEDSFAEQ
GYKKYVSNYLESNTAGDPYTDYEKASGSFDKAIKTEARDPLVAAYPIVGVGMEKLIISTNEHA
STDQGKTVSRATTNSKTESNTAGVSVNVGYQNGFTANVTTNYSHTTDNSTAVQDSNGESW
NTGLSINKGESAYINANVRYYNTGTAPMYKVTPTTNLVLDGDTLSTIKAQENQIGNNLSPGDT
YPKKGLSPLALNTMDQFSSRLIPINYDQLKKLDAGKQIKLETTQVSGNFGTKNSSGQIVTEGN
SWSDYISQIDSISASIILDTENESYERRVTAKNLQDPEDKTPELTIGEAIEKAFGATKKDGLLYF
NDIPIDESCVELIFDDNTANKIKDSLKTLSDKKIYNVKLERGMNILIKTPTYFTNFDDYNNYPST
WSNVNTTNQDGLQGSANKLNGETKIKIPMSELKPYKRYVFSGYSKDPLTSNSIIVKIKAKEEK
TDYLVPEQGYTKFSYEFETTEKDSSNIEITLIGSSGTTYLDNLSITELNSTPEILDEPEVKIPTDQE
IMDAHKIYFADLNFNPSTGNTYINGMYFAPTQTNKEALDYIQKYRVEATLQYSGFKDIGTKDK
EMRNYLGDPNQPKTNYVNLRSYFTGGENIMTYKKLRIYAITPDDRELLVLSVD HumanTrypsin-1 (Swiss Prot accession P07477)
SEQ ID NO: 7
IVGGYNCEENSVPYQVSLNSGYHFCGGSLINEQWVVSAGHCYKSRIQVRLGEHNIEVLEGN
EQFINAAKIIRHPQYDRKTLNNDIMLIKLSSRAVINARVSTISLPTAPPATGTKCLISGWGNTAS
SGADYPDELQCLDAPVLSQAKCEASYPGKITSNMFCVGFLEGGKDSCQGDSGGPVVCNGQ
LQGVVSWGDGCAQKNKPGVYTKVYNYVKWIKNTIAANS Human Trypsin-2 (Swiss Prot accession P07478)
SEQ ID NO: 8
IVGGYICEENSVPYQVSLNSGYHFCGGSLISEQWVVSAGHCYKSRIQVRLGEHNIEVLEGNE
QFINAAKIIRHPKYNSRTLDNDILLIKLSSPAVINSRVSAISLPTAPPAAGTESLISGWGNTLSSG
ADYPDELQCLDAPVLSQAECEASYPGKITNNMFCVGFLEGGKDSCQGDSGGPWSNGELQ
GIVSWGYGCAQKNRPGVYTKVYNYVDWIKDTIAANS Chymotrypsin-B (Swiss Prot accession P17538)
SEQ ID NO: 9
GCGVPAIHPVLSGLSRIVNGEDAVPGSWPWQVSLQDKTGFHFCGGSLISEDWVVTAAHCGV
RTSDVVVAGEFDQGSDEENIQVLKIAKVFKNPKFSILTVNNDITLLKLATPARFSQTVSAVCLP
SADDDFPAGTLCATTGWGKTKYNANKTPDKLQQAALPLLSNAECKKSWGRRITDVMICAGA
SGVSSCMGDSGGPLVCQKDGAWTLVGIVSWGSDTCSTSSPGVYARVTKLIPWVQKILAAN

The invention claimed is:

1. A method for treatment of *C. difficile* infection, comprising orally administering an antibody composition, the antibody composition comprising ovine antibodies that bind to a *C. difficile* toxin,
wherein the antibodies bind to *C. difficile* Toxin A and to *C. difficile* Toxin B.

2. The method of claim 1, wherein the antibodies are polyclonal antibodies.

3. The method of claim 1, wherein the antibodies bind to *C. difficile* toxins Toxin A, Toxin B, and Binary Toxin.

4. The method of claim 1, wherein the *C. difficile* Toxin A is selected from the group consisting of: Toxinotype 0, Toxinotype III and Toxinotype V.

5. The method of claim 1, wherein the *C. difficile* Toxin B is selected from the group consisting of: Toxinotype 0, Toxinotype III, Toxinotype V, and Toxinotype VIII.

6. The method of claim 1, wherein the antibody composition comprises:
the ovine antibodies that bind to a *C. difficile* toxin, and
at least one means for protecting said antibody composition from trypsin and/or chymotrypsin and/or stomach acid.

7. The method of claim 6, wherein the at least one means for protecting said antibody composition from trypsin and/or chymotrypsin and/or stomach acid is selected from the group consisting of:
(a) a polypeptide which binds specifically to and suppresses or inactivates the proteolytic activity of trypsin and/or chymotrypsin;
(b) an antibody that binds to trypsin and/or chymotrypsin and suppresses or inactivates the protease activity of said trypsin and/or chymotrypsin;
(c) a delivery vehicle selected from a liposome, a microsome, a nanosome, a pellet, a granular matrix, a bead, a microsphere, a nanoparticle formulation, or an aqueous solution;
(d) an antacid molecule;
(e) a PEGylation moiety covalent attached to one of more of the antibodies.

8. The method of claim 7, wherein the antibody composition includes the antacid molecule and:
(a) the polypeptide which binds specifically to and suppresses or inactivates the proteolytic activity of trypsin and/or chymotrypsin; or
(b) the antibody that binds to trypsin and/or chymotrypsin and inactivates the protease activity of said trypsin and/or chymotrypsin.

9. The method according to claim 1, further comprising administering at least one trypsin and/or chymotrypsin inhibitor and/or antacid prior to, simultaneously with, or subsequent to the administering the antibody composition.

10. The method according to claim 1, further comprising non-orally administering a second ovine antibody composition wherein said second ovine antibody composition comprises ovine antibodies that bind to a *C. difficile* toxin.

11. The method according to claim 1, wherein a subject to be treated is a subject selected from the group consisting of: hospitalized subjects; subjects over 65 years old; subjects receiving broad-range spectrum antibiotics; subjects having previous CDI infection; subjects having close proximity to symptomatic CDI patients; subjects having mild to moderate disease severity; subjects presenting as asymptomatic but considered at high risk of relapse; and subjects having close proximity to CDI outbreak areas or patients.

12. The method of claim 1, wherein the antibody composition comprises:
the ovine antibodies that bind to a *C. difficile* toxin, and
an excipient,
wherein the excipient provides for colonic delivery of the antibodies from oral administration.

13. The method of claim 12, wherein the excipient is selected from the group consisting of:
(a) a polypeptide which binds specifically to and suppresses or inactivates the proteolytic activity of trypsin and/or chymotrypsin;
(b) an antibody that binds to trypsin and/or chymotrypsin and suppresses or inactivates the protease activity of trypsin and/or chymotrypsin;
(c) a delivery vehicle selected from a liposome, a microsome, and a nanosome; and
(d) an antacid molecule.

14. A method for preventing at least one clinical symptom of *C. difficile* infection, comprising orally administering an antibody composition, the antibody composition comprising ovine antibodies that bind to a *C. difficile* toxin,
wherein the antibodies bind to *C. difficile* Toxin A and to *C. difficile* Toxin B.

15. The method according to claim 14, further comprising administering at least one trypsin and/or chymotrypsin inhibitor and/or antacid prior to, simultaneously with, or subsequent to the administering of the antibody composition.

16. The method according to claim 14, further comprising non-orally administering a second ovine antibody composition wherein said second ovine antibody composition comprises ovine antibodies that bind to a *C. difficile* toxin.

* * * * *

UNITED STATES PATENT AND TRADEMARK OFFICE
CERTIFICATE OF CORRECTION

| | | |
|---|---|---|
| PATENT NO. | : 8,921,529 B2 | Page 1 of 2 |
| APPLICATION NO. | : 13/513555 | |
| DATED | : December 30, 2014 | |
| INVENTOR(S) | : Clifford Shone et al. | |

It is certified that error appears in the above-identified patent and that said Letters Patent is hereby corrected as shown below:

On the Title Page:

Assignee Item (73):

Please delete "Health Protection Agency, Salisbury (GB)" and insert --The Secretary of State for Health, London (GB); Micropharm Limited, Newcastle Emlyn (GB)--

References Cited Item (56):

Page 1.

Col. 2, Line 43, please delete "Nguiyen" and insert --Nguyen--

Page 2.

Col. 1, Line 25, please delete "}"
Col. 1, Line 36, please delete "hiswtiding" and insert --histidine--

Col. 2, Line 73, please delete "filed" and insert --mailed--

Page 3.

Col. 1, Line 2, please delete "filed" and insert --mailed--
Col. 1, Line 3, please delete "filed" and insert --mailed--

Col. 2, Line 1, please delete "filed" and insert --mailed--
Col. 2, Line 2, please delete "filed" and insert --mailed--

Signed and Sealed this
Seventh Day of June, 2016

Michelle K. Lee
*Director of the United States Patent and Trademark Office*

CERTIFICATE OF CORRECTION (continued)
U.S. Pat. No. 8,921,529 B2

In the Claims:

Col. 105, Line 38, please delete ";" and insert --; and--
Col. 105, Line 39, please delete "covalent attached to one of more" and insert --covalently attached to one or more--